(12) United States Patent
Lee

(10) Patent No.: US 9,920,306 B2
(45) Date of Patent: *Mar. 20, 2018

(54) MUTANT β-GLUCURONIDASE ENZYMES WITH ENHANCED ENZYMATIC ACTIVITY

(71) Applicant: INTEGRATED MICRO-CHROMATOGRAPHY SYSTEMS, LLC, Irmo, SC (US)

(72) Inventor: Lim Andrew Lee, Columbia, SC (US)

(73) Assignee: INTEGRATED MICRO-CHROMATOGRAPHY SYSTEMS, LLC, Irmo, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/867,710

(22) Filed: Sep. 28, 2015

(65) Prior Publication Data

US 2016/0090582 A1   Mar. 31, 2016

Related U.S. Application Data

(60) Provisional application No. 62/056,800, filed on Sep. 29, 2014.

(51) Int. Cl.
C12N 9/24 (2006.01)

(52) U.S. Cl.
CPC .... C12N 9/2402 (2013.01); C12Y 302/01031 (2013.01)

(58) Field of Classification Search
None
See application file for complete search history.

(56) References Cited

U.S. PATENT DOCUMENTS

| | | |
|---|---|---|
| 6,391,547 B1 | 5/2002 | Jefferson et al. |
| 6,641,996 B1 | 11/2003 | Jefferson et al. |
| 6,664,097 B2 | 12/2003 | Russell et al. |
| 7,087,420 B1 | 8/2006 | Jefferson et al. |
| 7,141,719 B2 | 11/2006 | Jefferson et al. |
| 7,148,407 B2 | 12/2006 | Wenzl |
| 7,176,006 B2 | 2/2007 | Jefferson et al. |
| 8,491,891 B2 | 7/2013 | Roffler et al. |
| 2003/0003562 A1 | 1/2003 | Russell et al. |
| 2003/0157684 A1 | 8/2003 | Jefferson et al. |
| 2004/0091922 A1 | 5/2004 | Russell et al. |

(Continued)

FOREIGN PATENT DOCUMENTS

| WO | 00/55333 A1 | 9/2000 |
|---|---|---|
| WO | 2015/016124 A1 | 2/2015 |

OTHER PUBLICATIONS

PIR Accession No. A25047, published Jun. 30, 1988.*

(Continued)

*Primary Examiner* — Richard C Ekstrom
(74) *Attorney, Agent, or Firm* — Nelson Mullins Riley & Scarborough LLP; Jill Gorny Sloper, Esq.

(57) ABSTRACT

Mutated β-glucuronidase enzymes with enhanced enzymatic activity and thermostability as compared to wild type enzyme are provided. The enzymes of the invention advantageously allow for accurate analysis of bodily samples for the presence of drugs in 30 minutes or less, as compared to the several hours needed using prior enzyme preparations. Methods of using the mutated enzymes for hydrolysis of glucuronide substrates, including opiates and benzodiazepines, are also provided.

35 Claims, 14 Drawing Sheets

(56) References Cited

U.S. PATENT DOCUMENTS

| | | | |
|---|---|---|---|
| 2005/0153448 A1 | 7/2005 | Wenzl | |
| 2005/0227306 A1* | 10/2005 | Fox | C12Q 1/37 435/23 |
| 2007/0037246 A1* | 2/2007 | Butt | C07K 14/00 435/69.1 |
| 2007/0081986 A1 | 4/2007 | Tomatsu et al. | |
| 2009/0041741 A1 | 2/2009 | Sly et al. | |
| 2010/0129367 A1 | 5/2010 | Roffler et al. | |
| 2013/0011381 A1 | 1/2013 | Sly et al. | |
| 2016/0237415 A1 | 8/2016 | Lee | |

OTHER PUBLICATIONS

PIR Accession No. A72300, published Jun. 11, 1999.*
Hernandez et al., "Control of protein immobilization: Coupling immobilization and site-directed mutagenesis to improve biocatalyst or biosensor performance", Enzyme and Microbial Technology, vol. 48, pp. 107-122, 2011.*
Geneseq Accession No. AAW93827, published Jun. 15, 2007.*
Aich S. et al., "Expression and Purification of *Escherichia coli* beta-Glucuronidase," Protein Expression and Purification, vol. 22 (1), pp. 75-81 (2001).
Callanan, M.J. et al., "Modification of Lactobacillus beta-glucuronidase activity by random mutagenesis," Gene, vol. 389, pp. 122-127 (2007).
Chen, C. et al., "ECSTASY, an adjustable membrane-tethered/soluble protein expression system for the directed evolution of mammalian proteins," Protein Engineering, Design & Selection, vol. 25(7), pp. 367-375 (2012).
Flores, H. et al., "Increasing the thermal stability of an oligomeric protein, beta-glucuronidase," J. Mol. Biol., vol. 315, Issue 3, pp. 325-337 (2002).
Geddie, M. et al., "Rapid Evolution of beta-Glucuronidase Specificity by Saturation Mutagenesis of an Active Site Loop," The Journal of Biological Chemistry, vol. 279(25) pp. 26462-26468 (2004).
Kim H.S. et al., "Cloning and expression of beta-glucuronidase from Lactobacillus brevis in *E. coli* and application in the bioconversion of baicalin and wogonoside," J Microbiol Biotechnol., vol. 19(12), pp. 1650-1655 (2009).
Matsumura, I., et al., "In vitro evolution of beta-glucuronidase into a beta-galactosidase proceeds through non-specific intermediates," J. Mol. Biol., vol. 305(2), pp. 331-339 (2001).
Matsumura, I. et al., "Directed evolution of the surface chemistry of the reporter enzyme beta-glucuronidase," Nat. Biotechnol., vol. 17(7), pp. 696-701 (1999).
Morris, A. et al., "Opioid Hydrolysis by a Novel Recombinant Beta-Glucuronidase for Urinalysis," Ameritox Medication Monitoring Solutions, Poster Presentation, 2014, Society of Forensic Toxicologists Annual Meeting, held in Grand Rapids, Michigan, Oct. 19-24, 2014, 1 page.
Morris, A.A. et al., "Rapid Enzymatic Hydrolysis Using a Novel Recombinant beta-Glucuronidase in Benzodiazepine Urinalysis," Journal of Analytical Toxicology, vol. 38, pp. 610-614 (2014).
Morris, A.A. et al., "Rapid Enzyme Hydrolysis Using A Novel Recombinant beta-Glucuronidase in Benzodiazepine Urinalysis," Ameritox Medication Monitoring Solutions, Poster Presentation, 2014, American Association of Clinical Chemistry Annual Meeting in Chicago, Illinois, Jul. 30, 2014, 1 page.
Morris, A.A. et al., Buprenorphine Hydrolysis Using a Novel Recombinant Beta-glucuronidase for Urine Drug Testing, Ameritox Medication Monitoring Solutions, Poster Presentation, 2014, Society of Forensic Toxicologists Annual Meeting, held in Grand Rapids, Michigan, Oct. 19-24, 2014, 1 page.
Russell W.M., et al., "Identification and cloning of gusA, Encoding a New Beta-Glucuronidase from Lactobacillus Gasseri ADH," Applied and Environmental Microbiology, vol. 67(3), pp. 1253-1261 (2001).
Xiong, A.S. et al., "Directed evolution of a beta-galactosidase from Pyrococcus woesei resulting in increased thermostable beta-glucuronidase activity," Appl Microbiol Biotechnoly, vol. 77(3), pp. 569-578 (2007).
Xiong, A., et al. "Concurrent mutations in six amino acids in beta-glucuronidase improve its thermostability," Protein Engineering, Design & Selection, vol. 20(7) pp. 319-325 (2007).
U.S. Appl. No. 15/076,134, filed Mar. 21, 2016.
U.S. Appl. No. 15/076,183, filed Mar. 21, 2016.
U.S. Appl. No. 15/076,134, filed Jul. 27, 2016.
U.S. Appl. No. 15/076,134, filed Apr. 3, 2017.
U.S. Appl. No. 15/076,134, filed Dec. 2, 2016.
U.S. Appl. No. 15/076,183, filed Mar. 24, 2017.
GenBank Accession No. WP 15255760.1, published May 28, 2013.
Genseq Accession No. AAW93825, published Jun. 15, 2007.

* cited by examiner

```
WT      1   mlrpvetptreikkldglwafsldrencgidqrwwesalq
K1S     1   mlrpvetptreikkldglwafsldrencgidqrwwesalq
K1T     1   mlrpvetptreikkldglwafsldrencgidqrwwesalq
K3      1   mlrpvetptreikkldglwafsldrencgidqrwwesalq
K3Δ1    1   mlrpvetptreikkldglwafsldrencgidqrwwesalq
K3Δ2    1   mlrpvetptreikkldglwafsldrencgidqrwwesalq
K3Δ2S   1   mlrpvetptreikkldglwafsldrencgidqrwwesalq WT      41  esraiavpgsfndqfadadirnyagnvwyqrevfipkgwagqrivlrfdavthygkvwvn
K1S     41  esraiavpgsfndqfadadirnyagnvwyqrevfipkgwagqrivlrfdavthygkvwvn
K1T     41  esraiavpgsfndqfadadirnyagnvwyqrevfipkgwagqrivlrfdavthygkvwvn
K3      41  esraiavpgsfndqfadadirnyagnvwyqrevfipkgwagqrivlrfdavthygkvwvn
K3Δ1    41  esraiavpgsfndqfadadirnyagnvwyqrevfipkgwagqrivlrfdavthygkvwvn
K3Δ2    41  esraiavpgsfndqfadadirnyagnvwyqrevfipkgwagqrivlrfdavthygkvwvn
K3Δ2S   41  esraiavpgsfndqfadadirnyagnvwyqrevfipkgwagqrivlrfdavthygkvwvn WT      101 nqevmehqggytpfeadvtpyviagksvritvcvnnelnwqtippgmvitdengkkkqsy
K1S     101 nqevmehqggytpfeadvtpyviagksvritvcvnnelnwqtippgmvitdengkkkqsy
K1T     101 nqevmehqggytpfeadvtpyviagksvritvcvnnelnwqtippgmvitdengkkkqsy
K3      101 nqevmehqggytpfeadvtpyviagksvritvcvnnelnwqtippgmvitdengkkkqsy
K3Δ1    101 nqevmehqggytpfeadvtpyviagksvritvcvnnelnwqtippgmvitdengkkkqsy
K3Δ2    101 nqevmehqggytpfeadvtpyviagksvritvcvnnelnwqtippgmvitdengkkkqsy
K3Δ2S   101 nqevmehqggytpfeadvtpyviagksvritvcvnnelnwqtippgmvitdengkkkqsy WT      161 fhdffnyagihrsvmlyttpntwvdditvvthvaqdcnhasvdwqvvangdvsvelrdad
K1S     161 fhdffnyagihrsvmlyttpntwvdditvvthvaqdcnhasvdwqvvangdvsvelrdad
K1T     161 fhdffnyagihrsvmlyttpntwvdditvvthvaqdcnhasvdwqvvangdvsvelrdad
K3      161 fhdffnyagihrsvmlyttpntwvdditvvthvaqdcnhasvdwqvvangdvsvelrdad
K3Δ1    161 fhdffnyagihrsvmlyttpntwvdditvvthvaqdcnhasvdwqvvangdvsvelrdad
K3Δ2    161 fhdffnyagihrsvmlyttpntwvdditvvthvaqdcnhasvdwqvvangdvsvelrdad
K3Δ2S   161 fhdffnyagihrsvmlyttpntwvdditvvthvaqdcnhasvdwqvvangdvsvelrdad WT      221 qqvvatgqgtsgtlqvvnphlwqpgegylyelcvtaksqtecdiyplrvgirsvavkgeq
K1S     221 qqvvatgqgtsgtlqvvnphlwqpgegylyelcvtaksqtecdiyplrvgirsvavkgeq
K1T     221 qqvvatgqgtsgtlqvvnphlwqpgegylyelcvtaksqtecdiyplrvgirsvavkgeq
K3      221 qqvvatgqgtsgtlqvvnphlwqpgegylyelcvtaksqtecdiyplrvgirsvavkgeq
K3Δ1    221 qqvvatgqgtsgtlqvvnphlwqpgegylyelcvtaksqtecdiyplrvgirsvavkgeq
K3Δ2    221 qqvvatgqgtsgtlqvvnphlwqpgegylyelcvtaksqtecdiyplrvgirsvavkgeq
K3Δ2S   221 qqvvatgqgtsgtlqvvnphlwqpgegylyelcvtaksqtecdiyplrvgirsvavkgeq
```

FIGURE 1A

```
WT     281  flinhkpfyftgfgrhedadlrgkgfdnvlmvhdhalmdwigansyrtshypyaeemldw
K1S    281  flinhkpfyftgfgrhedadlrgkgfdnvlmvhdhalmdwigansyrtshypyaeemldw
K1T    281  flinhkpfyftgfgrhedadlrgkgfdnvlmvhdhalmdwigansyrtshypyaeemldw
K3     281  flinhkpfyftgfgrhedadlrgkgfdnvlmvhdhalmdwigansyrtshypyaeemldw
K3Δ1   281  flinhkpfyftgfgrhedadlrgkgfdnvlmvhdhalmdwigansyrtshypyaeemldw
K3Δ2   281  flinhkpfyftgfgrhedadlrgkgfdnvlmvhdhalmdwigansyrtshypyaeemldw
K3Δ2S  281  flinhkpfyftgfgrhedadlrgkgfdnvlmvhdhalmdwigansyrtshypyaeemldw WT     341  adehgivvidetaavgfnlslgigfeagnkpkelyseeavngetqqahlqaikeliardk
K1S    341  adehgivvidetaavgfnlslgigfeagnkpkelyseeavngetqqahlqaikeliardk
K1T    341  adehgivvidetaavgfnlslgigfeagnkpkelyseeavngetqqahlqaikeliardk
K3     341  adehgivvidetaavgfnlslgigfeagnkpkelyseeavngetqqahlqaikeliardk
K3Δ1   341  adehgivvidetaavgfnlslgig------pkelyseeavngetqqahlqaikeliardk
K3Δ2   341  adehgivvidetaavgfnlslgig------------eeavngetqqahlqaikeliardk
K3Δ2S  341  adehgivvidetaavgfnlslgig------------pqffngetqqahlqaikeliardk WT     401  nhpsvvmwsianepdtrpqgareyfaplaeatrkldptrpitcvnvmfcdahtdtisdlf
K1S    401  nhpsvvmwsianepdtrpqgareyfaplaeatrkldptrpitcvnvmfcdahtdtisdlf
K1T    401  nhpsvvmwsianepdtrpqgareyfaplaeatrkldptrpitcvnvmfcdahtdtisdlf
K3     401  nhpsvvmwsianepdtrpqgareyfaplaeatrkldptrpitcvnvmfcdahtdtisdlf
K3Δ1   395  nhpsvvmwsianepdtrpqgareyfaplaeatrkldptrpitcvnvmfcdahtdtisdlf
K3Δ2   389  nhpsvvmwsianepdtrpqgareyfaplaeatrkldptrpitcvnvmfcdahtdtisdlf
K3Δ2S  389  nhpsvvmwsianepdtrpqgareyfaplaeatrkldptrpitcvnvmfcdahtdtisdlf WT     461  dvlclnryygwyvqsgdletaekvlekellawqeklhqpiiiteygvdtlaglhsmytdm
K1S    461  dvlclnryygwyvqsgdletaekvlekellawqeklhqpiiiteygvdtlaglhsmytdm
K1T    461  dvlclnryygwyvqsgdletaekvlekellawqeklhqpiiiteygvdtlaglhsmytdm
K3     461  dvlclnryygwyvqsgdletaekvlekellawqeklhqpiiiteygvdtlaglhsmytdm
K3Δ1   455  dvlclnryygwyvqsgdletaekvlekellawqeklhqpiiiteygvdtlaglhsmytdm
K3Δ2   449  dvlclnryygwyvqsgdletaekvlekellawqeklhqpiiiteygvdtlaglhsmytdm
K3Δ2S  449  dvlclnryygwyvqsgdletaekvlekellawqeklhqpiiiteygvdtlaglhsmytdm WT     521  wseeyqcawldmyhrvfdrvsavvgeqvwnfadfatsqgilrvggnkkgiftrdrkpksa
K1S    521  wseeyqcawldmyhrvfdrvsavvgeqvwnfadfatsqsilrvggnkkgiftrdrkpksa
K1T    521  wseeyqcawldmyhrvfdrvsavvgeqvwnfadfatsqtilrvggnkkgiftrdrkpksa
K3     521  wseeyqcawldmyhrvfdrvsavvgeqvwnfadfatsqsilrvggnkkgiftrdrkpksa
K3Δ1   515  wseeyqcawldmyhrvfdrvsavvgeqvwnfadfatsqsilrvggnkkgiftrdrkpksa
K3Δ2   509  wseeyqcawldmyhrvfdrvsavvgeqvwnfadfatsqsilrvggnkkgiftrdrkpksa
K3Δ2S  509  wseeyqcawldmyhrvfdrvsavvgeqvwnfadfatsqsilrvggnkkgiftrdrkpksa WT     581  afllqkrwtgmnfgekpqqggkq---
K1S    581  afllqkrwtgmnfgekpqqggkq---
K1T    581  afllqkrwtgmnfgekpqqggkq---
K3     581  afllqkrwtgmnfgekpqqggkqglc
K3Δ1   575  afllqkrwtgmnfgekpqqggkqglc
K3Δ2   569  afllqkrwtgmnfgekpqqggkqglc
K3Δ2S  569  afllqkrwtgmnfgekpqqggkqglc
```

FIGURE 1B

```
K3      332    pyaeemldwadehgivvidetaavqfnlsigigfeagnkpkelyeeavngetqqahiqa
Ab             pyaeeimdqadqqgvmviespgvqid----------------edenfsnisllhhmev
Hu             pyaeevmqmcdrygivvidecpgvqla----------------lpqffnnvslhhimqv
L. br          pyseemmrlcdregivvidevpavqlmlsftfdvsalek-ddfeddtweklrtaeahrqa
S. rlh         pyseelmrladregivvidetpavqvhlnfmattglge--gservstwekirtfehiqdv K3      392    ikeliardknhpsvvmwsianedt
Ab             mselvqrdknrpsvfmwsvaneqrs
Hu             meelvvrdknhpavvmwsvanegas
L. br          itemidrdknhasvvmwsisneaan
S. rlh         lrelvsrdknhpsvvmwsianeaat
```

FIGURE 2

```
K3    452  htdtisdlfavlclnrygwyvqsgdletaekvlekeliaqqekihq-pliteygvdtl
Ab         yndkaipyvdiicfnrygwysdtghteviqlqgsdmdgwrskynk-pliteygadtv
Hu         aadkgapyvdviclnsyyswyhdyghleliqlqatqfenwykkyqk-plqseygaeti
L. br      ktdrclaladvialnrygwymgngdlkaaetatreellayqakfpdkpimyteygadtia
S. rlh     etdkvaelidvialnryngwyfdggdleaakvhlrqefhawnkrcpgkpimiteygadtv K3    512  glhsmytdmwseeyqcawldmyhrvfd-rvsa--wvgeqvwnfadfatsqsilrvggnkk
Ab         glhrdpssvfteeyqvdfmseyhklfdsrigky-lvgemvwnfadfmtkqgvtrvvgnkk
Hu         gfhqdpplmfteeyqksileqyhiglqqkrrky-wvgeliwnfadfmtegsptrvlgnkk
L. br      glhsyndepfseefgedyyrmcsrvfd-evtn--fvgeqiwnfadfqtkfgiqrgqgnkk
S. rlh     gfhdidpvmfteeyqveyyqanhvvfd-efen--fvgeqawnfadfatsqgvmrvqgnkk K3    569  giftrdrkpksaaflqkrwtgmnfgekpqqggkqglc
Ab         qvltrqrqpkaaaflrnryhklmnstrhh
Hu         giftrqrqpksaafllrerywkianetryphsvaksqclenspft
L. br      glftrarepkmvvryltqrwrnipdfnykk
S. rlh     gvftrdrkpklaahvfrerwtnipdfgykn
```

FIGURE 3

Abalone BGUS Loop Region Insertions

```
Wt-Ab    pyaeeimdqadqqgvmvidespgvgid-----------------edenfsnisllhhmev
Ab1      pyaeeimdqadqqgvmvidespgvgfnlslgigfeagnkpkelyedenfsnisllhhmev
Ab2      pyaeeimdqadqqgvmvidespgvgidlgigfeagnkpkely--edenfsnisllhhmev
```

FIGURE 9A

Human BGUS Loop Region Insertions

```
Wt-Hu    pyaeevmqmcdrygivvidecpgvgla-----------------lpqffnnvslhhhmqv
Hu1      pyaeevmqmcdrygivvidecpgvgfnlslgigfeagnkpkelyseeafnnvslhhhmqv
Hu2      pyaeevmqmcdrygivvidecpgvgfnlslgigfeagnkpkelyedenfnnvslhhhmqv
```

FIGURE 9B

SEQUENCE LISTING

<160> NUMBER OF SEQ ID NOS: 104

<210> SEQ ID NO 1
<211> LENGTH: 1812
<212> TYPE: DNA
<213> ORGANISM: Escherichia coli

<400> SEQUENCE: 1

| | | | | | |
|---|---|---|---|---|---|
| atgttacgtc | ctgtagaaac | cccaacccgt | gaaatcaaaa | aactcgacgg | cctgtgggca | 60 |
| ttcagtctgg | atcgcgaaaa | ctgtggaatt | gatcagcgtt | ggtgggaaag | cgcgttacaa | 120 |
| gaaagccggg | caattgctgt | gccaggcagt | tttaacgatc | agttcgccga | tgcagatatt | 180 |
| cgtaattatg | cgggcaacgt | ctggtatcag | cgcgaagtct | ttataccgaa | aggttgggca | 240 |
| ggccagcgta | tcgtgctgcg | tttcgatgcg | gtcactcatt | acggcaaagt | gtgggtcaat | 300 |
| aatcaggaag | tgatggagca | tcagggcggc | tatacgccat | tgaagccga | tgtcacgccg | 360 |
| tatgttattg | ccgggaaaag | tgtacgtatc | accgtttgtg | tgaacaacga | actgaactgg | 420 |
| cagactatcc | cgccgggaat | ggtgattacc | gacgaaaacg | gcaagaaaaa | gcagtcttac | 480 |
| ttccatgatt | tctttaacta | tgccgggatc | catcgcagcg | taatgctcta | caccacgccg | 540 |
| aacacctggg | tggacgatat | caccgtggtg | acgcatgtcg | cgcaagactg | taaccacgcg | 600 |
| tctgttgact | ggcaggtggt | ggccaatggt | gatgtcagcg | ttgaactgcg | tgatgcggat | 660 |
| caacaggtgg | ttgcaactgg | acaaggcact | agcgggactt | tgcaagtggt | gaatccgcac | 720 |
| ctctggcaac | cgggtgaagg | ttatctctat | gaactgtgcg | tcacagccaa | agccagaca | 780 |
| gagtgtgata | tctacccgct | tcgcgtcggc | atccggtcag | tggcagtgaa | gggcgaacag | 840 |
| ttcctgatta | ccacaaaacc | gttctacttt | actggctttg | gtcgtcatga | agatgcggac | 900 |
| ttgcgtggca | aaggattcga | taacgtgctg | atggtgcacg | accacgcatt | aatggactgg | 960 |
| attggggcca | actcctaccg | tacctcgcat | taccctacg | ctgaagagat | gctcgactgg | 1020 |
| gcagatgaac | atggcatcgt | ggtgattgat | gaaactgctg | ctgtcggctt | taacctctct | 1080 |
| ttaggcattg | gtttcgaagc | gggcaacaag | ccgaaagaac | tgtacagcga | agaggcagtc | 1140 |
| aacggggaaa | ctcagcaagc | gcacttacag | gcgattaaag | agctgatagc | gcgtgacaaa | 1200 |
| aaccacccaa | gcgtggtgat | gtggagtatt | gccaacgaac | cggataccg | tccgcaaggt | 1260 |
| gcacgggaat | atttcgcgcc | actggcggaa | gcaacgcgta | aactcgaccc | gacgcgtccg | 1320 |
| atcacctgcg | tcaatgtaat | gttctgcgac | gctcacaccg | ataccatcag | cgatctcttt | 1380 |
| gatgtgctgt | gcctgaaccg | ttattacgga | tggtatgtcc | aaagcggcga | tttggaaacg | 1440 |
| gcagagaagg | tactgaaaaa | agaacttctg | gcctggcagg | agaaactgca | tcagccgatt | 1500 |
| atcatcaccg | aatacggcgt | ggatacgtta | gccgggctgc | actcaatgta | caccgacatg | 1560 |
| tggagtgaag | agtatcagtg | tgcatggctg | gatatgtatc | accgcgtctt | tgatcgcgtc | 1620 |
| agcgccgtcg | tcggtgaaca | ggtatggaat | ttcgccgatt | ttgcgacctc | gcaaggcata | 1680 |
| ttgcgcgttg | gcggtaacaa | gaaagggatc | ttcactcgcg | accgcaaacc | gaagtcggcg | 1740 |
| gcttttctgc | tgcaaaaacg | ctggactggc | atgaacttcg | gtgaaaaacc | gcagcaggga | 1800 |
| ggcaaacaat | ga | | | | | 1812 |

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gagagacata tgttacgtcc tgtagaaacc cc                                32

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagagaaagc tttcattgtt tgcctccctg ct                                32

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgctgtcgg ctttaacctc                                              20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gacctcgcaa agcatattgc g                                            21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgcaatatgc tttgcgaggt c                                            21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctagttattg ctcagcggt                                               19

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 8
gcgacctcgc aaaccatatt gcgc                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgcaatatg gtttgcgagg tcgc                                          24

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caaacaaggc ctatgctaga aaggagaagc ttg                                33

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagcttctc ctttctagca taggccttgt ttg                                33

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctttaggca ttggtccgaa agaactgtac                                    30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtacagttct ttcggaccaa tgcctaaaga                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 14
tctttaggca ttggtgaaga ggcagtcaac                                30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttgactgcc tcttcaccaa tgcctaaaga                                30

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccgcagttct tcaacgggga aactcag                                   27

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaagaactgc ggaccaatgc ctaaagag                                  28

<210> SEQ ID NO 18
<211> LENGTH: 603
<212> TYPE: PRT
<213> ORGANISM: Escherichia coli

<400> SEQUENCE: 18

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
                20                  25                  30

Arg Trp Trp Glu Ser Ala Leu Gln Glu Ser Arg Ala Ile Ala Val Pro
            35                  40                  45

Gly Ser Phe Asn Asp Gln Phe Ala Asp Ala Asp Ile Arg Asn Tyr Ala
        50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr

-continued

```
            145                 150                 155                 160
        Phe His Asp Phe Phe Asn Tyr Ala Gly Ile His Arg Ser Val Met Leu
                        165                 170                 175
        Tyr Thr Thr Pro Asn Thr Trp Val Asp Asp Ile Thr Val Val Thr His
                        180                 185                 190
        Val Ala Gln Asp Cys Asn His Ala Ser Val Asp Trp Gln Val Val Ala
                        195                 200                 205
        Asn Gly Asp Val Ser Val Glu Leu Arg Asp Ala Asp Gln Gln Val Val
                        210                 215                 220
        Ala Thr Gly Gln Gly Thr Ser Gly Thr Leu Gln Val Val Asn Pro His
        225                 230                 235                 240
        Leu Trp Gln Pro Gly Glu Gly Tyr Leu Tyr Glu Leu Cys Val Thr Ala
                        245                 250                 255
        Lys Ser Gln Thr Glu Cys Asp Ile Tyr Pro Leu Arg Val Gly Ile Arg
                        260                 265                 270
        Ser Val Ala Val Lys Gly Glu Gln Phe Leu Ile Asn His Lys Pro Phe
                        275                 280                 285
        Tyr Phe Thr Gly Phe Gly Arg His Glu Asp Ala Asp Leu Arg Gly Lys
                        290                 295                 300
        Gly Phe Asp Asn Val Leu Met Val His Asp His Ala Leu Met Asp Trp
        305                 310                 315                 320
        Ile Gly Ala Asn Ser Tyr Arg Thr Ser His Tyr Pro Tyr Ala Glu Glu
                        325                 330                 335
        Met Leu Asp Trp Ala Asp Glu His Gly Ile Val Val Ile Asp Glu Thr
                        340                 345                 350
        Ala Ala Val Gly Phe Asn Leu Ser Leu Gly Ile Gly Phe Glu Ala Gly
                        355                 360                 365
        Asn Lys Pro Lys Glu Leu Tyr Ser Glu Glu Ala Val Asn Gly Glu Thr
                        370                 375                 380
        Gln Gln Ala His Leu Gln Ala Ile Lys Glu Leu Ile Ala Arg Asp Lys
        385                 390                 395                 400
        Asn His Pro Ser Val Val Met Trp Ser Ile Ala Asn Glu Pro Asp Thr
                        405                 410                 415
        Arg Pro Gln Gly Ala Arg Glu Tyr Phe Ala Pro Leu Ala Glu Ala Thr
                        420                 425                 430
        Arg Lys Leu Asp Pro Thr Arg Pro Ile Thr Cys Val Asn Val Met Phe
                        435                 440                 445
        Cys Asp Ala His Thr Asp Thr Ile Ser Asp Leu Phe Asp Val Leu Cys
        450                 455                 460
        Leu Asn Arg Tyr Tyr Gly Trp Tyr Val Gln Ser Gly Asp Leu Glu Thr
        465                 470                 475                 480
        Ala Glu Lys Val Leu Glu Lys Glu Leu Leu Ala Trp Gln Glu Lys Leu
                        485                 490                 495
        His Gln Pro Ile Ile Ile Thr Glu Tyr Gly Val Asp Thr Leu Ala Gly
                        500                 505                 510
        Leu His Ser Met Tyr Thr Asp Met Trp Ser Glu Glu Tyr Gln Cys Ala
                        515                 520                 525
        Trp Leu Asp Met Tyr His Arg Val Phe Asp Arg Val Ser Ala Val Val
                        530                 535                 540
        Gly Glu Gln Val Trp Asn Phe Ala Asp Phe Ala Thr Ser Gln Gly Ile
        545                 550                 555                 560
        Leu Arg Val Gly Gly Asn Lys Lys Gly Ile Phe Thr Arg Asp Arg Lys
                        565                 570                 575
```

```
Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
            595                 600
```

<210> SEQ ID NO 19
<211> LENGTH: 603
<212> TYPE: PRT
<213> ORGANISM: Escherichia coli

<400> SEQUENCE: 19

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
```

```
                     340                 345                 350
Ala Ala Val Gly Phe Asn Leu Ser Leu Gly Ile Gly Phe Glu Ala Gly
            355                 360                 365

Asn Lys Pro Lys Glu Leu Tyr Ser Glu Glu Ala Val Asn Gly Glu Thr
        370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
        530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600

<210> SEQ ID NO 20
<211> LENGTH: 603
<212> TYPE: PRT
<213> ORGANISM: Escherichia coli

<400> SEQUENCE: 20

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110
```

```
Pro Phe Glu Ala Asp Val Thr Pro Tyr Val Ile Ala Gly Lys Ser Val
            115                 120                 125
Arg Ile Thr Val Cys Val Asn Asn Glu Leu Asn Trp Gln Thr Ile Pro
        130                 135                 140
Pro Gly Met Val Ile Thr Asp Glu Asn Gly Lys Lys Lys Gln Ser Tyr
145                 150                 155                 160
Phe His Asp Phe Phe Asn Tyr Ala Gly Ile His Arg Ser Val Met Leu
                165                 170                 175
Tyr Thr Thr Pro Asn Thr Trp Val Asp Asp Ile Thr Val Val Thr His
            180                 185                 190
Val Ala Gln Asp Cys Asn His Ala Ser Val Asp Trp Gln Val Val Ala
        195                 200                 205
Asn Gly Asp Val Ser Val Glu Leu Arg Asp Ala Asp Gln Gln Val Val
210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
Lys Ser Gln Thr Glu Cys Asp Ile Tyr Pro Leu Arg Val Gly Ile Arg
            260                 265                 270
Ser Val Ala Val Lys Gly Glu Gln Phe Leu Ile Asn His Lys Pro Phe
        275                 280                 285
Tyr Phe Thr Gly Phe Gly Arg His Glu Asp Ala Asp Leu Arg Gly Lys
    290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
            340                 345                 350
Ala Ala Val Gly Phe Asn Leu Ser Leu Gly Ile Gly Phe Glu Ala Gly
        355                 360                 365
Asn Lys Pro Lys Glu Leu Tyr Ser Glu Ala Val Asn Gly Glu Thr
370                 375                 380
Gln Gln Ala His Leu Gln Ala Ile Lys Glu Leu Ile Ala Arg Asp Lys
385                 390                 395                 400
Asn His Pro Ser Val Val Met Trp Ser Ile Ala Asn Glu Pro Asp Thr
                405                 410                 415
Arg Pro Gln Gly Ala Arg Glu Tyr Phe Ala Pro Leu Ala Glu Ala Thr
            420                 425                 430
Arg Lys Leu Asp Pro Thr Arg Pro Ile Thr Cys Val Asn Val Met Phe
        435                 440                 445
Cys Asp Ala His Thr Asp Thr Ile Ser Asp Leu Phe Asp Val Leu Cys
450                 455                 460
Leu Asn Arg Tyr Tyr Gly Trp Tyr Val Gln Ser Gly Asp Leu Glu Thr
465                 470                 475                 480
Ala Glu Lys Val Leu Glu Lys Glu Leu Leu Ala Trp Gln Glu Lys Leu
                485                 490                 495
His Gln Pro Ile Ile Ile Thr Glu Tyr Gly Val Asp Thr Leu Ala Gly
            500                 505                 510
Leu His Ser Met Tyr Thr Asp Met Trp Ser Glu Glu Tyr Gln Cys Ala
        515                 520                 525
Trp Leu Asp Met Tyr His Arg Val Phe Asp Arg Val Ser Ala Val Val
```

```
                530             535             540
Gly Glu Gln Val Trp Asn Phe Ala Asp Phe Ala Thr Ser Gln Thr Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
                580                 585                 590

Phe Gly Glu Lys Pro Gln Gln Gly Gly Lys Gln
            595                 600

<210> SEQ ID NO 21
<211> LENGTH: 606
<212> TYPE: PRT
<213> ORGANISM: Escherichia coli

<400> SEQUENCE: 21

Met Leu Arg Pro Val Glu Thr Pro Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300
```

```
Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Lys Gln Gly Leu Cys
        595                 600                 605

<210> SEQ ID NO 22
<211> LENGTH: 600
<212> TYPE: PRT
<213> ORGANISM: Escherichia coli

<400> SEQUENCE: 22

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80
```

```
Gly Gln Arg Ile Val Leu Arg Phe Asp Ala Val Thr His Tyr Gly Lys
                85                  90                  95
Val Trp Val Asn Asn Gln Glu Val Met Glu His Gln Gly Gly Tyr Thr
                100                 105                 110
Pro Phe Glu Ala Asp Val Thr Pro Tyr Val Ile Ala Gly Lys Ser Val
                115                 120                 125
Arg Ile Thr Val Cys Val Asn Asn Glu Leu Asn Trp Gln Thr Ile Pro
        130                 135                 140
Pro Gly Met Val Ile Thr Asp Glu Asn Gly Lys Lys Gln Ser Tyr
145                 150                 155                 160
Phe His Asp Phe Phe Asn Tyr Ala Gly Ile His Arg Ser Val Met Leu
                165                 170                 175
Tyr Thr Thr Pro Asn Thr Trp Val Asp Asp Ile Thr Val Val Thr His
                180                 185                 190
Val Ala Gln Asp Cys Asn His Ala Ser Val Asp Trp Gln Val Val Ala
                195                 200                 205
Asn Gly Asp Val Ser Val Glu Leu Arg Asp Ala Asp Gln Val Val
                210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
Lys Ser Gln Thr Glu Cys Asp Ile Tyr Pro Leu Arg Val Gly Ile Arg
                260                 265                 270
Ser Val Ala Val Lys Gly Glu Gln Phe Leu Ile Asn His Lys Pro Phe
                275                 280                 285
Tyr Phe Thr Gly Phe Gly Arg His Glu Asp Ala Asp Leu Arg Gly Lys
                290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
                340                 345                 350
Ala Ala Val Gly Phe Asn Leu Ser Leu Gly Ile Gly Pro Lys Glu Leu
                355                 360                 365
Tyr Ser Glu Glu Ala Val Asn Gly Glu Thr Gln Gln Ala His Leu Gln
                370                 375                 380
Ala Ile Lys Glu Leu Ile Ala Arg Asp Lys Asn His Pro Ser Val Val
385                 390                 395                 400
Met Trp Ser Ile Ala Asn Glu Pro Asp Thr Arg Pro Gln Gly Ala Arg
                405                 410                 415
Glu Tyr Phe Ala Pro Leu Ala Glu Ala Thr Arg Lys Leu Asp Pro Thr
                420                 425                 430
Arg Pro Ile Thr Cys Val Asn Val Met Phe Cys Asp Ala His Thr Asp
                435                 440                 445
Thr Ile Ser Asp Leu Phe Asp Val Leu Cys Leu Asn Arg Tyr Tyr Gly
                450                 455                 460
Trp Tyr Val Gln Ser Gly Asp Leu Glu Thr Ala Glu Lys Val Leu Glu
465                 470                 475                 480
Lys Glu Leu Leu Ala Trp Gln Glu Lys Leu His Gln Pro Ile Ile Ile
                485                 490                 495
```

```
Thr Glu Tyr Gly Val Asp Thr Leu Ala Gly Leu His Ser Met Tyr Thr
                500                 505                 510

Asp Met Trp Ser Glu Glu Tyr Gln Cys Ala Trp Leu Asp Met Tyr His
            515                 520                 525

Arg Val Phe Asp Arg Val Ser Ala Val Val Gly Glu Gln Val Trp Asn
        530                 535                 540

Phe Ala Asp Phe Ala Thr Ser Gln Ser Ile Leu Arg Val Gly Gly Asn
545                 550                 555                 560

Lys Lys Gly Ile Phe Thr Arg Asp Arg Lys Pro Lys Ser Ala Ala Phe
                565                 570                 575

Leu Leu Gln Lys Arg Trp Thr Gly Met Asn Phe Gly Glu Lys Pro Gln
            580                 585                 590

Gln Gly Gly Lys Gln Gly Leu Cys
        595                 600

<210> SEQ ID NO 23
<211> LENGTH: 594
<212> TYPE: PRT
<213> ORGANISM: Escherichia coli

<400> SEQUENCE: 23

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270
```

```
Ser Val Ala Val Lys Gly Glu Gln Phe Leu Ile Asn His Lys Pro Phe
            275                 280                 285
Tyr Phe Thr Gly Phe Gly Arg His Glu Asp Ala Asp Leu Arg Gly Lys
        290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Ile Asp Glu Thr
            340                 345                 350
Ala Ala Val Gly Phe Asn Leu Ser Leu Gly Ile Gly Glu Ala Val
                355                 360                 365
Asn Gly Glu Thr Gln Gln Ala His Leu Gln Ala Ile Lys Glu Leu Ile
    370                 375                 380
Ala Arg Asp Lys Asn His Pro Ser Val Val Met Trp Ser Ile Ala Asn
385                 390                 395                 400
Glu Pro Asp Thr Arg Pro Gln Gly Ala Arg Glu Tyr Phe Ala Pro Leu
                405                 410                 415
Ala Glu Ala Thr Arg Lys Leu Asp Pro Thr Arg Pro Ile Thr Cys Val
            420                 425                 430
Asn Val Met Phe Cys Asp Ala His Thr Asp Thr Ile Ser Asp Leu Phe
        435                 440                 445
Asp Val Leu Cys Leu Asn Arg Tyr Tyr Gly Trp Tyr Val Gln Ser Gly
    450                 455                 460
Asp Leu Glu Thr Ala Glu Lys Val Leu Glu Lys Glu Leu Leu Ala Trp
465                 470                 475                 480
Gln Glu Lys Leu His Gln Pro Ile Ile Ile Thr Glu Tyr Gly Val Asp
                485                 490                 495
Thr Leu Ala Gly Leu His Ser Met Tyr Thr Asp Met Trp Ser Glu Glu
            500                 505                 510
Tyr Gln Cys Ala Trp Leu Asp Met Tyr His Arg Val Phe Asp Arg Val
        515                 520                 525
Ser Ala Val Val Gly Glu Gln Val Trp Asn Phe Ala Asp Phe Ala Thr
    530                 535                 540
Ser Gln Ser Ile Leu Arg Val Gly Gly Asn Lys Lys Gly Ile Phe Thr
545                 550                 555                 560
Arg Asp Arg Lys Pro Lys Ser Ala Ala Phe Leu Leu Gln Lys Arg Trp
                565                 570                 575
Thr Gly Met Asn Phe Gly Glu Lys Pro Gln Gln Gly Leu Lys Gln Gly
            580                 585                 590
Leu Cys

<210> SEQ ID NO 24
<211> LENGTH: 594
<212> TYPE: PRT
<213> ORGANISM: Escherichia coli

<400> SEQUENCE: 24

Met Leu Arg Pro Val Glu Thr Pro Thr Arg Glu Ile Lys Lys Leu Asp
1               5                   10                  15
Gly Leu Trp Ala Phe Ser Leu Asp Arg Glu Asn Cys Gly Ile Asp Gln
            20                  25                  30
Arg Trp Trp Glu Ser Ala Leu Gln Glu Ser Arg Ala Ile Ala Val Pro
        35                  40                  45
```

```
Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
                100                 105                 110

Pro Phe Glu Ala Asp Val Thr Pro Tyr Val Ile Ala Gly Lys Ser Val
            115                 120                 125

Arg Ile Thr Val Cys Val Asn Asn Glu Leu Asn Trp Gln Thr Ile Pro
130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
                180                 185                 190

Val Ala Gln Asp Cys Asn His Ala Ser Val Asp Trp Gln Val Val Ala
            195                 200                 205

Asn Gly Asp Val Ser Val Glu Leu Arg Asp Ala Asp Gln Gln Val Val
210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
                260                 265                 270

Ser Val Ala Val Lys Gly Glu Gln Phe Leu Ile Asn His Lys Pro Phe
            275                 280                 285

Tyr Phe Thr Gly Phe Gly Arg His Glu Asp Ala Asp Leu Arg Gly Lys
                290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Pro Gln Phe Phe
            355                 360                 365

Asn Gly Glu Thr Gln Gln Ala His Leu Gln Ala Ile Lys Glu Leu Ile
370                 375                 380

Ala Arg Asp Lys Asn His Pro Ser Val Met Trp Ser Ile Ala Asn
385                 390                 395                 400

Glu Pro Asp Thr Arg Pro Gln Gly Ala Arg Glu Tyr Phe Ala Pro Leu
                405                 410                 415

Ala Glu Ala Thr Arg Lys Leu Asp Pro Thr Arg Pro Ile Thr Cys Val
            420                 425                 430

Asn Val Met Phe Cys Asp Ala His Thr Asp Thr Ile Ser Asp Leu Phe
            435                 440                 445

Asp Val Leu Cys Leu Asn Arg Tyr Tyr Gly Trp Tyr Val Gln Ser Gly
    450                 455                 460
```

```
Asp Leu Glu Thr Ala Glu Lys Val Leu Glu Lys Leu Leu Ala Trp
465                 470                 475                 480

Gln Glu Lys Leu His Gln Pro Ile Ile Ile Thr Glu Tyr Gly Val Asp
                485                 490                 495

Thr Leu Ala Gly Leu His Ser Met Tyr Thr Asp Met Trp Ser Glu Glu
            500                 505                 510

Tyr Gln Cys Ala Trp Leu Asp Met Tyr His Arg Val Phe Asp Arg Val
        515                 520                 525

Ser Ala Val Val Gly Glu Gln Val Trp Asn Phe Ala Asp Phe Ala Thr
    530                 535                 540

Ser Gln Ser Ile Leu Arg Val Gly Gly Asn Lys Lys Gly Ile Phe Thr
545                 550                 555                 560

Arg Asp Arg Lys Pro Lys Ser Ala Ala Phe Leu Leu Gln Lys Arg Trp
                565                 570                 575

Thr Gly Met Asn Phe Gly Glu Lys Pro Gln Gln Gly Lys Gln Gly
                580                 585                 590

Leu Cys
```

<210> SEQ ID NO 25
<211> LENGTH: 85
<212> TYPE: PRT
<213> ORGANISM: Escherichia coli

<400> SEQUENCE: 25

```
Pro Tyr Ala Glu Glu Met Leu Asp Trp Ala Asp Glu His Gly Ile Val
1               5                   10                  15

Val Ile Asp Glu Thr Ala Ala Val Gly Phe Asn Leu Ser Leu Gly Ile
                20                  25                  30

Gly Phe Glu Ala Gly Asn Lys Pro Lys Glu Leu Tyr Ser Glu Ala
            35                  40                  45

Val Asn Gly Glu Thr Gln Gln Ala His Leu Gln Ala Ile Lys Glu Leu
    50                  55                  60

Ile Ala Arg Asp Lys Asn His Pro Ser Val Val Met Trp Ser Ile Ala
65                  70                  75                  80

Asn Glu Pro Asp Thr
                85
```

<210> SEQ ID NO 26
<211> LENGTH: 68
<212> TYPE: PRT
<213> ORGANISM: Haliotis rufescens

<400> SEQUENCE: 26

```
Pro Tyr Ala Glu Glu Ile Met Asp Gln Ala Asp Gln Gln Gly Val Met
1               5                   10                  15

Val Ile Asp Glu Ser Pro Gly Val Gly Ile Asp Glu Asp Glu Asn Phe
                20                  25                  30

Ser Asn Ile Ser Leu Leu His His Met Glu Val Met Ser Glu Leu Val
            35                  40                  45

Gln Arg Asp Lys Asn Arg Pro Ser Val Phe Met Trp Ser Val Ala Asn
    50                  55                  60

Glu Pro Arg Ser
65
```

<210> SEQ ID NO 27
<211> LENGTH: 68
<212> TYPE: PRT

<213> ORGANISM: Homo sapiens

<400> SEQUENCE: 27

Pro Tyr Ala Glu Glu Val Met Gln Met Cys Asp Arg Tyr Gly Ile Val
1               5                   10                  15

Val Ile Asp Glu Cys Pro Gly Val Gly Leu Ala Leu Pro Gln Phe Phe
                20                  25                  30

Asn Asn Val Ser Leu His His His Met Gln Val Met Glu Glu Leu Val
            35                  40                  45

Val Arg Asp Lys Asn His Pro Ala Val Val Met Trp Ser Val Ala Asn
    50                  55                  60

Glu Pro Ala Ser
65

<210> SEQ ID NO 28
<211> LENGTH: 84
<212> TYPE: PRT
<213> ORGANISM: Lactobacillus brevis

<400> SEQUENCE: 28

Pro Tyr Ser Glu Glu Met Met Arg Leu Cys Asp Arg Glu Gly Ile Val
1               5                   10                  15

Val Ile Asp Glu Val Pro Ala Val Gly Leu Met Leu Ser Phe Thr Phe
                20                  25                  30

Asp Val Ser Ala Leu Glu Lys Asp Asp Phe Glu Asp Thr Trp Glu
            35                  40                  45

Lys Leu Arg Thr Ala Glu Ala His Arg Gln Ala Ile Thr Glu Met Ile
    50                  55                  60

Asp Arg Asp Lys Asn His Ala Ser Val Val Met Trp Ser Ile Ser Asn
65                  70                  75                  80

Glu Ala Ala Asn

<210> SEQ ID NO 29
<211> LENGTH: 83
<212> TYPE: PRT
<213> ORGANISM: Staphylococcus sp.

<400> SEQUENCE: 29

Pro Tyr Ser Glu Glu Leu Met Arg Leu Ala Asp Arg Glu Gly Leu Val
1               5                   10                  15

Val Ile Asp Glu Thr Pro Ala Val Gly Val His Leu Asn Phe Met Ala
                20                  25                  30

Thr Thr Gly Leu Gly Glu Gly Ser Glu Arg Val Ser Thr Trp Glu Lys
            35                  40                  45

Ile Arg Thr Phe Glu His His Gln Asp Val Leu Arg Glu Leu Val Ser
    50                  55                  60

Arg Asp Lys Asn His Pro Ser Val Val Met Trp Ser Ile Ala Asn Glu
65                  70                  75                  80

Ala Ala Thr

<210> SEQ ID NO 30
<211> LENGTH: 155
<212> TYPE: PRT
<213> ORGANISM: Escherichia coli

<400> SEQUENCE: 30

His Thr Asp Thr Ile Ser Asp Leu Phe Asp Val Leu Cys Leu Asn Arg
1               5                   10                  15

```
Tyr Tyr Gly Trp Tyr Val Gln Ser Gly Asp Leu Glu Thr Ala Glu Lys
            20                  25                  30

Val Leu Glu Lys Glu Leu Leu Ala Trp Gln Glu Lys Leu His Gln Pro
        35                  40                  45

Ile Ile Ile Thr Glu Tyr Gly Val Asp Thr Leu Ala Gly Leu His Ser
    50                  55                  60

Met Tyr Thr Asp Met Trp Ser Glu Glu Tyr Gln Cys Ala Trp Leu Asp
65                  70                  75                  80

Met Tyr His Arg Val Phe Asp Arg Val Ser Ala Val Val Gly Glu Gln
                85                  90                  95

Val Trp Asn Phe Ala Asp Phe Ala Thr Ser Gln Ser Ile Leu Arg Val
        100                 105                 110

Gly Gly Asn Lys Lys Gly Ile Phe Thr Arg Asp Arg Lys Pro Lys Ser
            115                 120                 125

Ala Ala Phe Leu Leu Gln Lys Arg Trp Thr Gly Met Asn Phe Gly Glu
        130                 135                 140

Lys Pro Gln Gln Gly Gly Lys Gln Gly Leu Cys
145                 150                 155

<210> SEQ ID NO 31
<211> LENGTH: 149
<212> TYPE: PRT
<213> ORGANISM: Haliotis rufescens

<400> SEQUENCE: 31

Tyr Asn Asp Lys Ala Ile Pro Tyr Val Asp Ile Ile Cys Phe Asn Arg
1               5                   10                  15

Tyr Tyr Gly Trp Tyr Ser Asp Thr Gly His Thr Glu Val Ile Gln Leu
            20                  25                  30

Gln Leu Gly Ser Asp Met Asp Gly Trp Arg Ser Lys Tyr Asn Lys Pro
        35                  40                  45

Leu Ile Ile Thr Glu Tyr Gly Ala Asp Thr Val Ala Gly Leu His Arg
    50                  55                  60

Asp Pro Ser Ser Val Phe Thr Glu Glu Tyr Gln Val Asp Phe Met Ser
65                  70                  75                  80

Glu Tyr His Lys Leu Phe Asp Ser Arg Ile Gly Lys Tyr Leu Val Gly
                85                  90                  95

Glu Met Val Trp Asn Phe Ala Asp Phe Met Thr Lys Gln Gly Val Thr
        100                 105                 110

Arg Val Val Gly Asn Lys Lys Gly Val Leu Thr Arg Gln Arg Gln Pro
            115                 120                 125

Lys Ala Ala Ala Phe Leu Leu Arg Asn Arg Tyr His Lys Leu Met Asn
        130                 135                 140

Ser Thr Arg His His
145

<210> SEQ ID NO 32
<211> LENGTH: 164
<212> TYPE: PRT
<213> ORGANISM: Homo sapiens

<400> SEQUENCE: 32

Ala Ala Asp Lys Gly Ala Pro Tyr Val Asp Val Ile Cys Leu Asn Ser
1               5                   10                  15

Tyr Tyr Ser Trp Tyr His Asp Tyr Gly His Leu Glu Leu Ile Gln Leu
            20                  25                  30
```

```
Gln Leu Ala Thr Gln Phe Glu Asn Trp Tyr Lys Lys Tyr Gln Lys Pro
        35                  40                  45

Ile Ile Gln Ser Glu Tyr Gly Ala Glu Thr Ile Ala Gly Phe His Gln
 50                  55                  60

Asp Pro Pro Leu Met Phe Thr Glu Glu Tyr Gln Lys Ser Leu Leu Glu
 65                  70                  75                  80

Gln Tyr His Leu Gly Leu Asp Gln Lys Arg Arg Lys Tyr Val Val Gly
                 85                  90                  95

Glu Leu Ile Trp Asn Phe Ala Asp Phe Met Thr Glu Gln Ser Pro Thr
                100                 105                 110

Arg Val Leu Gly Asn Lys Lys Gly Ile Phe Thr Arg Gln Arg Gln Pro
                115                 120                 125

Lys Ser Ala Ala Phe Leu Leu Arg Glu Arg Tyr Trp Lys Ile Ala Asn
130                 135                 140

Glu Thr Arg Tyr Pro His Ser Val Ala Lys Ser Gln Cys Leu Glu Asn
145                 150                 155                 160

Ser Pro Phe Thr

<210> SEQ ID NO 33
<211> LENGTH: 148
<212> TYPE: PRT
<213> ORGANISM: Lactobacillus brevis

<400> SEQUENCE: 33

Lys Thr Asp Arg Cys Leu Ala Leu Ala Asp Val Ile Ala Leu Asn Arg
 1               5                  10                  15

Tyr Tyr Gly Trp Tyr Met Gly Asn Gly Asp Leu Lys Ala Ala Glu Thr
                 20                  25                  30

Ala Thr Arg Glu Glu Leu Leu Ala Tyr Gln Ala Lys Phe Pro Asp Lys
            35                  40                  45

Pro Ile Met Tyr Thr Glu Tyr Gly Ala Asp Thr Ile Ala Gly Leu His
 50                  55                  60

Ser Tyr Asn Asp Glu Pro Phe Ser Glu Glu Phe Gln Glu Asp Tyr Tyr
 65                  70                  75                  80

Arg Met Cys Ser Arg Val Phe Asp Glu Val Thr Asn Phe Val Gly Glu
                 85                  90                  95

Gln Leu Trp Asn Phe Ala Asp Phe Gln Thr Lys Phe Gly Ile Gln Arg
                100                 105                 110

Gly Gln Gly Asn Lys Lys Gly Ile Phe Thr Arg Ala Arg Glu Pro Lys
                115                 120                 125

Met Val Val Arg Tyr Leu Thr Gln Arg Trp Arg Asn Ile Pro Asp Phe
130                 135                 140

Asn Tyr Lys Lys
145

<210> SEQ ID NO 34
<211> LENGTH: 148
<212> TYPE: PRT
<213> ORGANISM: Staphylococcus sp.

<400> SEQUENCE: 34

Glu Thr Asp Lys Val Ala Glu Leu Ile Asp Val Ile Ala Leu Asn Arg
 1               5                  10                  15

Tyr Asn Gly Trp Tyr Phe Asp Gly Gly Asp Leu Glu Ala Ala Lys Val
                 20                  25                  30
```

His Leu Arg Gln Glu Phe His Ala Trp Asn Lys Arg Cys Pro Gly Lys
          35                  40                  45

Pro Ile Met Ile Thr Glu Tyr Gly Ala Asp Thr Val Ala Gly Phe His
 50                  55                  60

Asp Ile Asp Pro Val Met Phe Thr Glu Glu Tyr Gln Val Glu Tyr Tyr
 65                  70                  75                  80

Gln Ala Asn His Val Val Phe Asp Glu Phe Glu Asn Phe Val Gly Glu
                  85                  90                  95

Gln Ala Trp Asn Phe Ala Asp Phe Ala Thr Ser Gln Gly Val Met Arg
             100                 105                 110

Val Gln Gly Asn Lys Lys Gly Val Phe Thr Arg Asp Arg Lys Pro Lys
         115                 120                 125

Leu Ala Ala His Val Phe Arg Glu Arg Trp Thr Asn Ile Pro Asp Phe
130                 135                 140

Gly Tyr Lys Asn
145

<210> SEQ ID NO 35
<211> LENGTH: 60
<212> TYPE: PRT
<213> ORGANISM: Haliotis rufescens

<400> SEQUENCE: 35

Pro Tyr Ala Glu Glu Ile Met Asp Gln Ala Asp Gln Gln Gly Val Met
 1               5                  10                  15

Val Ile Asp Glu Ser Pro Gly Val Gly Phe Asn Leu Ser Leu Gly Ile
             20                  25                  30

Gly Phe Glu Ala Gly Asn Lys Pro Lys Glu Leu Tyr Glu Asp Glu Asn
         35                  40                  45

Phe Ser Asn Ile Ser Leu Leu His His Met Glu Val
 50                  55                  60

<210> SEQ ID NO 36
<211> LENGTH: 58
<212> TYPE: PRT
<213> ORGANISM: Haliotis rufescens

<400> SEQUENCE: 36

Pro Tyr Ala Glu Glu Ile Met Asp Gln Ala Asp Gln Gln Gly Val Met
 1               5                  10                  15

Val Ile Asp Glu Ser Pro Gly Val Gly Ile Asp Leu Gly Ile Gly Phe
             20                  25                  30

Glu Ala Gly Asn Lys Pro Lys Glu Leu Tyr Glu Asp Glu Asn Phe Ser
         35                  40                  45

Asn Ile Ser Leu Leu His His Met Glu Val
 50                  55

<210> SEQ ID NO 37
<211> LENGTH: 60
<212> TYPE: PRT
<213> ORGANISM: Homo sapiens

<400> SEQUENCE: 37

Pro Tyr Ala Glu Glu Val Met Gln Met Cys Asp Arg Tyr Gly Ile Val
 1               5                  10                  15

Val Ile Asp Glu Cys Pro Gly Val Gly Phe Asn Leu Ser Leu Gly Ile
             20                  25                  30

Gly Phe Glu Ala Gly Asn Lys Pro Lys Glu Leu Tyr Ser Glu Glu Ala

```
                35                  40                  45

Phe Asn Asn Val Ser Leu His His Met Gln Val
 50                  55                  60

<210> SEQ ID NO 38
<211> LENGTH: 60
<212> TYPE: PRT
<213> ORGANISM: Homo sapiens

<400> SEQUENCE: 38

Pro Tyr Ala Glu Glu Val Met Gln Met Cys Asp Arg Tyr Gly Ile Val
 1               5                  10                  15

Val Ile Asp Glu Cys Pro Gly Val Gly Phe Asn Leu Ser Leu Gly Ile
                20                  25                  30

Gly Phe Glu Ala Gly Asn Lys Pro Lys Glu Leu Tyr Glu Asp Glu Asn
                35                  40                  45

Phe Asn Asn Val Ser Leu His His Met Gln Val
 50                  55                  60

<210> SEQ ID NO 39
<211> LENGTH: 651
<212> TYPE: PRT
<213> ORGANISM: Homo sapiens

<400> SEQUENCE: 39

Met Ala Arg Gly Ser Ala Val Ala Trp Ala Ala Leu Gly Pro Leu Leu
 1               5                  10                  15

Trp Gly Cys Ala Leu Gly Leu Gln Gly Gly Met Leu Tyr Pro Gln Glu
                20                  25                  30

Ser Pro Ser Arg Glu Cys Lys Glu Leu Asp Gly Leu Trp Ser Phe Arg
                35                  40                  45

Ala Asp Phe Ser Asp Asn Arg Arg Arg Gly Phe Glu Glu Gln Trp Tyr
 50                  55                  60

Arg Arg Pro Leu Trp Glu Ser Gly Pro Thr Val Asp Met Pro Val Pro
 65                  70                  75                  80

Ser Ser Phe Asn Asp Ile Ser Gln Asp Trp Arg Leu Arg His Phe Val
                85                  90                  95

Gly Trp Val Trp Tyr Glu Arg Glu Val Ile Leu Pro Glu Arg Trp Thr
                100                 105                 110

Gln Asp Leu Arg Thr Arg Val Val Leu Arg Ile Gly Ser Ala His Ser
                115                 120                 125

Tyr Ala Ile Val Trp Val Asn Gly Val Asp Thr Leu Glu His Glu Gly
                130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
                180                 185                 190

Ser Lys Tyr Pro Lys Gly Tyr Phe Val Gln Asn Thr Tyr Phe Asp Phe
                195                 200                 205

Phe Asn Tyr Ala Gly Leu Gln Arg Ser Val Leu Leu Tyr Thr Thr Pro
                210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
```

245                 250                 255
Lys Leu Glu Val Arg Leu Leu Asp Ala Glu Asn Lys Val Val Ala Asn
                260                 265                 270
Gly Thr Gly Thr Gln Gly Gln Leu Lys Val Pro Gly Val Ser Leu Trp
            275                 280                 285
Trp Pro Tyr Leu Met His Glu Arg Pro Ala Tyr Leu Tyr Ser Leu Glu
        290                 295                 300
Val Gln Leu Thr Ala Gln Thr Ser Leu Gly Pro Val Ser Asp Phe Tyr
305                 310                 315                 320
Thr Leu Pro Val Gly Ile Arg Thr Val Ala Val Thr Lys Ser Gln Phe
                325                 330                 335
Leu Ile Asn Gly Lys Pro Phe Tyr Phe His Gly Val Asn Lys His Glu
                340                 345                 350
Asp Ala Asp Ile Arg Gly Lys Gly Phe Asp Trp Pro Leu Leu Val Lys
            355                 360                 365
Asp Phe Asn Leu Leu Arg Trp Leu Gly Ala Asn Ala Phe Arg Thr Ser
        370                 375                 380
His Tyr Pro Tyr Ala Glu Glu Val Met Gln Met Cys Asp Arg Tyr Gly
385                 390                 395                 400
Ile Val Val Ile Asp Glu Cys Pro Gly Val Gly Leu Ala Leu Pro Gln
                405                 410                 415
Phe Phe Asn Asn Val Ser Leu His His His Met Gln Val Met Glu Glu
                420                 425                 430
Val Val Arg Arg Asp Lys Asn His Pro Ala Val Val Met Trp Ser Val
            435                 440                 445
Ala Asn Glu Pro Ala Ser His Leu Glu Ser Ala Gly Tyr Tyr Leu Lys
        450                 455                 460
Met Val Ile Ala His Thr Lys Ser Leu Asp Pro Ser Arg Pro Val Thr
465                 470                 475                 480
Phe Val Ser Asn Ser Asn Tyr Ala Ala Asp Lys Gly Ala Pro Tyr Val
                485                 490                 495
Asp Val Ile Cys Leu Asn Ser Tyr Tyr Ser Trp Tyr His Asp Tyr Gly
            500                 505                 510
His Leu Glu Leu Ile Gln Leu Gln Leu Ala Thr Gln Phe Glu Asn Trp
        515                 520                 525
Tyr Lys Lys Tyr Gln Lys Pro Ile Ile Gln Ser Glu Tyr Gly Ala Glu
        530                 535                 540
Thr Ile Ala Gly Phe His Gln Asp Pro Pro Leu Met Phe Thr Glu Glu
545                 550                 555                 560
Tyr Gln Lys Ser Leu Leu Glu Gln Tyr His Leu Gly Leu Asp Gln Lys
                565                 570                 575
Arg Arg Lys Tyr Val Val Gly Glu Leu Ile Trp Asn Phe Ala Asp Phe
            580                 585                 590
Met Thr Glu Gln Ser Pro Thr Arg Val Leu Gly Asn Lys Lys Gly Ile
        595                 600                 605
Phe Thr Arg Gln Arg Gln Pro Lys Ser Ala Ala Phe Leu Leu Arg Glu
    610                 615                 620
Arg Tyr Trp Lys Ile Ala Asn Glu Thr Arg Tyr Pro His Ser Val Ala
625                 630                 635                 640
Lys Ser Gln Cys Leu Glu Asn Ser Leu Phe Thr
                645                 650

<210> SEQ ID NO 40

<211> LENGTH: 648
<212> TYPE: PRT
<213> ORGANISM: Mus sp.

<400> SEQUENCE: 40

```
Met Ser Leu Lys Trp Ser Ala Cys Trp Val Ala Leu Gly Gln Leu Leu
1               5                   10                  15

Cys Ser Cys Ala Leu Ala Leu Lys Gly Gly Met Leu Phe Pro Lys Glu
            20                  25                  30

Ser Pro Ser Arg Glu Leu Lys Ala Leu Asp Gly Leu Trp His Phe Arg
        35                  40                  45

Ala Asp Leu Ser Asn Asn Arg Leu Gln Gly Phe Glu Gln Gln Trp Tyr
    50                  55                  60

Arg Gln Pro Leu Arg Glu Ser Gly Pro Val Leu Asp Met Pro Val Pro
65                  70                  75                  80

Ser Ser Phe Asn Asp Ile Thr Gln Glu Ala Ala Leu Arg Asp Phe Ile
                85                  90                  95

Gly Trp Val Trp Tyr Glu Arg Glu Ala Ile Leu Pro Arg Arg Trp Thr
            100                 105                 110

Gln Asp Thr Asp Met Arg Val Val Leu Arg Ile Asn Ser Ala His Tyr
        115                 120                 125

Tyr Ala Val Val Trp Val Asn Gly Ile His Val Val Glu His Glu Gly
    130                 135                 140

Gly His Leu Pro Phe Glu Ala Asp Ile Ser Lys Leu Val Gln Ser Gly
145                 150                 155                 160

Pro Leu Thr Thr Cys Arg Ile Thr Ile Ala Ile Asn Asn Thr Leu Thr
                165                 170                 175

Pro His Thr Leu Pro Pro Gly Thr Ile Val Tyr Lys Thr Asp Thr Ser
            180                 185                 190

Met Tyr Pro Lys Gly Tyr Phe Val Gln Asp Thr Ser Phe Asp Phe Phe
        195                 200                 205

Asn Tyr Ala Gly Leu His Arg Ser Val Val Leu Tyr Thr Thr Pro Thr
    210                 215                 220

Thr Tyr Ile Asp Asp Ile Thr Val Ile Thr Asn Val Glu Gln Asp Ile
225                 230                 235                 240

Gly Leu Val Thr Tyr Trp Ile Ser Val Gln Gly Ser Glu His Phe Gln
                245                 250                 255

Leu Glu Val Gln Leu Leu Asp Glu Gly Gly Lys Val Val Ala His Gly
            260                 265                 270

Thr Gly Asn Gln Gly Gln Leu Gln Val Pro Ser Ala Asn Leu Trp Trp
        275                 280                 285

Pro Tyr Leu Met His Glu His Pro Ala Tyr Met Tyr Ser Leu Glu Val
    290                 295                 300

Lys Val Thr Thr Thr Glu Ser Val Thr Asp Tyr Tyr Thr Leu Pro Ile
305                 310                 315                 320

Gly Ile Arg Thr Val Ala Val Thr Lys Ser Lys Phe Leu Ile Asn Gly
                325                 330                 335

Lys Pro Phe Tyr Phe Gln Gly Val Asn Lys His Glu Asp Ser Asp Ile
            340                 345                 350

Arg Gly Lys Gly Phe Asp Trp Pro Leu Leu Val Lys Asp Phe Asn Leu
        355                 360                 365

Leu Arg Trp Leu Gly Ala Asn Ser Phe Arg Thr Ser His Tyr Pro Tyr
    370                 375                 380

Ser Glu Glu Val Leu Gln Leu Cys Asp Arg Tyr Gly Ile Val Val Ile
```

-continued

```
                385                 390                 395                 400
Asp Glu Cys Pro Gly Val Gly Ile Val Leu Pro Gln Ser Phe Gly Asn
                405                 410                 415

Glu Ser Leu Arg His His Leu Glu Val Met Glu Glu Leu Val Arg Arg
            420                 425                 430

Asp Lys Asn His Pro Ala Val Met Trp Ser Val Ala Asn Glu Pro
            435                 440                 445

Ser Ser Ala Leu Lys Pro Ala Ala Tyr Tyr Phe Lys Thr Leu Ile Thr
    450                 455                 460

His Thr Lys Ala Leu Asp Leu Thr Arg Pro Val Thr Phe Val Ser Asn
465                 470                 475                 480

Ala Lys Tyr Asp Ala Asp Leu Gly Ala Pro Tyr Val Asp Val Ile Cys
            485                 490                 495

Val Asn Ser Tyr Phe Ser Trp Tyr His Asp Tyr Gly His Leu Glu Val
            500                 505                 510

Ile Gln Pro Gln Leu Asn Ser Gln Phe Glu Asn Trp Tyr Lys Thr His
        515                 520                 525

Gln Lys Pro Ile Ile Gln Ser Glu Tyr Gly Ala Asp Ala Ile Pro Gly
    530                 535                 540

Ile His Glu Asp Pro Pro Arg Met Phe Ser Glu Tyr Gln Lys Ala
545                 550                 555                 560

Val Leu Glu Asn Tyr His Ser Val Leu Asp Gln Lys Arg Lys Glu Tyr
            565                 570                 575

Val Val Gly Glu Leu Ile Trp Asn Phe Ala Asp Phe Met Thr Asn Gln
        580                 585                 590

Ser Pro Leu Arg Val Ile Gly Asn Lys Lys Gly Ile Phe Thr Arg Gln
    595                 600                 605

Arg Gln Pro Lys Thr Ser Ala Phe Ile Leu Arg Glu Arg Tyr Trp Arg
        610                 615                 620

Ile Ala Asn Glu Thr Gly Gly His Gly Ser Gly Pro Arg Thr Gln Cys
625                 630                 635                 640

Phe Gly Ser Arg Pro Phe Thr Phe
                645

<210> SEQ ID NO 41
<211> LENGTH: 603
<212> TYPE: PRT
<213> ORGANISM: Lactobacillus brevis

<400> SEQUENCE: 41

Met Leu Tyr Pro Met Glu Thr Ala Ser Arg Val Val Leu Asp Leu Ser
1               5                   10                  15

Gly Val Trp Arg Phe Met Ile Asp Lys Glu Gln Ile Pro Val Asp Val
            20                  25                  30

Thr Arg Pro Leu Pro Ala Thr Leu Ser Met Ala Val Pro Ala Ser Phe
        35                  40                  45

Asn Asp Gln Thr Ala Ser Lys Glu Ile Arg Glu His Val Gly Tyr Val
    50                  55                  60

Trp Tyr Glu Arg Cys Phe Glu Leu Pro Gln Leu Leu Arg Gln Glu Arg
65              70                  75                  80

Leu Val Leu Arg Phe Gly Ser Ala Thr His Glu Ala Trp Val Tyr Leu
            85                  90                  95

Asn Gly His Leu Ile Thr His His Lys Gly Gly Phe Thr Pro Phe Glu
            100                 105                 110
```

```
Val Glu Ile Asn Asp Asp Leu Val Thr Gly Glu Asn Arg Leu Thr Val
            115                 120                 125

Lys Leu Ser Asn Met Leu Asp Tyr Thr Thr Leu Pro Val Gly His Tyr
130                 135                 140

Lys Glu Thr Gln Asn Glu Thr Gly Gln Arg Val Arg Gln Leu Asp Glu
145                 150                 155                 160

Asn Phe Asp Phe Phe Asn Tyr Ala Gly Leu Gln Arg Pro Val Lys Ile
                165                 170                 175

Tyr Ser Thr Pro His Ser Tyr Ile Arg Asp Ile Thr Leu Thr Pro Lys
                180                 185                 190

Val Asn Leu Thr Asn His Ser Ala Val Val Asn Gly Glu Ile Glu Thr
                195                 200                 205

Val Gly Asp Val Glu Gln Val Val Thr Ile Leu Asp Glu Asp Asn
210                 215                 220

Gln Val Val Gly Thr Thr Ser Gly Lys Thr Leu Ala Ile Glu Leu Asn
225                 230                 235                 240

Ser Val His Leu Trp Gln Pro Gly Lys Ala Tyr Leu Tyr Arg Ala Lys
                245                 250                 255

Val Glu Leu Tyr Gln Ala Gly Gln Val Ile Asp Thr Tyr Ile Glu Thr
                260                 265                 270

Phe Gly Ile Arg Gln Ile Ala Val Lys Ala Gly Lys Phe Leu Ile Asn
                275                 280                 285

Gly Gln Pro Phe Tyr Phe Lys Gly Phe Gly Lys His Glu Asp Ala Tyr
                290                 295                 300

Ile His Gly Arg Gly Leu Ser Glu Pro Gln Asn Val Leu Asp Leu Ser
305                 310                 315                 320

Leu Met Lys Gln Met Gly Ala Asn Ser Phe Arg Thr Ser His Tyr Pro
                325                 330                 335

Tyr Ser Glu Glu Met Met Arg Leu Cys Asp Arg Glu Gly Ile Val Val
                340                 345                 350

Ile Asp Glu Val Pro Ala Val Gly Leu Met Leu Ser Phe Thr Phe Asp
                355                 360                 365

Val Ser Ala Leu Glu Lys Asp Asp Phe Glu Asp Asp Thr Trp Glu Lys
370                 375                 380

Leu Arg Thr Ala Glu Ala His Arg Gln Ala Ile Thr Glu Met Ile Asp
385                 390                 395                 400

Arg Asp Lys Asn His Ala Ser Val Val Met Trp Ser Ile Ser Asn Glu
                405                 410                 415

Ala Ala Asn Phe Ser Lys Gly Ala Tyr Glu Tyr Phe Lys Pro Leu Phe
                420                 425                 430

Asp Leu Ala Arg Lys Leu Asp Pro Gln Gln Arg Pro Cys Thr Ser Thr
                435                 440                 445

Ser Ile Met Met Thr Thr Leu Lys Thr Asp Arg Cys Leu Ala Leu Ala
                450                 455                 460

Asp Val Ile Ala Leu Asn Arg Tyr Tyr Gly Trp Tyr Met Gly Asn Gly
465                 470                 475                 480

Asp Leu Lys Ala Ala Glu Thr Ala Thr Arg Glu Glu Leu Leu Ala Tyr
                485                 490                 495

Gln Ala Lys Phe Pro Asp Lys Pro Ile Met Tyr Thr Glu Tyr Gly Ala
                500                 505                 510

Asp Thr Ile Ala Gly Leu His Ser Asn Tyr Asp Glu Pro Phe Ser Glu
                515                 520                 525

Glu Phe Gln Glu Asp Tyr Tyr Arg Met Cys Ser Arg Val Phe Asp Glu
```

```
                530             535             540
Val Thr Asn Phe Val Gly Glu Gln Leu Trp Asn Phe Ala Asp Phe Gln
545                 550             555                 560

Thr Lys Phe Gly Ile Gln Arg Gly Gln Gly Asn Lys Lys Gly Ile Phe
                565             570             575

Thr Arg Ala Arg Glu Pro Lys Met Val Val Arg Tyr Leu Thr Gln Arg
            580             585             590

Trp Arg Asn Ile Pro Asp Phe Asn Tyr Lys Lys
        595             600

<210> SEQ ID NO 42
<211> LENGTH: 602
<212> TYPE: PRT
<213> ORGANISM: Staphylococcus sp.

<400> SEQUENCE: 42

Met Leu Tyr Pro Ile Asn Thr Glu Thr Arg Gly Val Phe Asp Leu Asn
1               5                   10                  15

Gly Val Trp Asn Phe Lys Leu Asp Tyr Gly Lys Gly Leu Glu Glu Lys
            20                  25                  30

Trp Tyr Glu Ser Lys Leu Thr Asp Thr Ile Ser Met Ala Val Pro Ser
        35                  40                  45

Ser Tyr Asn Asp Ile Gly Val Thr Lys Glu Ile Arg Asn His Ile Gly
    50                  55                  60

Tyr Val Trp Tyr Glu Arg Glu Phe Thr Val Pro Ala Tyr Leu Lys Asp
65                  70                  75                  80

Gln Arg Ile Val Leu Arg Phe Gly Ser Ala Thr His Lys Ala Ile Val
                85                  90                  95

Tyr Val Asn Gly Glu Leu Val Val Glu His Lys Gly Gly Phe Leu Pro
            100                 105                 110

Phe Glu Ala Glu Ile Asn Asn Ser Leu Arg Asp Gly Met Asn Arg Val
        115                 120                 125

Thr Val Ala Val Asp Asn Ile Leu Asp Asp Ser Thr Leu Pro Val Gly
    130                 135                 140

Leu Tyr Ser Glu Arg His Glu Glu Gly Leu Gly Lys Val Ile Arg Asn
145                 150                 155                 160

Lys Pro Asn Phe Asp Phe Phe Asn Tyr Ala Gly Leu His Arg Pro Val
                165                 170                 175

Lys Ile Tyr Thr Thr Pro Phe Thr Tyr Val Glu Asp Ile Ser Val Val
            180                 185                 190

Thr Asp Phe Asn Gly Pro Thr Gly Thr Val Thr Tyr Thr Val Asp Phe
        195                 200                 205

Gln Gly Lys Ala Glu Thr Val Lys Val Ser Val Asp Glu Glu Gly
    210                 215                 220

Lys Val Val Ala Ser Thr Glu Gly Leu Ser Gly Asn Val Glu Ile Pro
225                 230                 235                 240

Asn Val Ile Leu Trp Glu Pro Leu Asn Thr Tyr Leu Tyr Gln Ile Lys
                245                 250                 255

Val Glu Leu Val Asn Asp Gly Leu Thr Ile Asp Val Tyr Glu Glu Pro
            260                 265                 270

Phe Gly Val Arg Thr Val Glu Val Asn Asp Gly Lys Phe Leu Ile Asn
        275                 280                 285

Asn Lys Pro Phe Tyr Phe Lys Gly Phe Gly Lys His Glu Asp Thr Pro
    290                 295                 300
```

```
Ile Asn Gly Arg Gly Phe Asn Glu Ala Ser Asn Val Met Asp Phe Asn
305                 310                 315                 320

Ile Leu Lys Trp Ile Gly Ala Asn Ser Phe Arg Thr Ala His Tyr Pro
            325                 330                 335

Tyr Ser Glu Glu Leu Met Arg Leu Ala Asp Arg Glu Gly Leu Val Val
        340                 345                 350

Ile Asp Glu Thr Pro Ala Val Gly Val His Leu Asn Phe Met Ala Thr
    355                 360                 365

Thr Gly Leu Gly Glu Gly Ser Glu Arg Val Ser Thr Trp Glu Lys Ile
370                 375                 380

Arg Thr Phe Glu His His Gln Asp Val Leu Arg Glu Leu Val Ser Arg
385                 390                 395                 400

Asp Lys Asn His Pro Ser Val Val Met Trp Ser Ile Ala Asn Glu Ala
                405                 410                 415

Ala Thr Glu Glu Glu Gly Ala Tyr Glu Tyr Phe Lys Pro Leu Val Glu
            420                 425                 430

Leu Thr Lys Glu Leu Asp Pro Gln Lys Arg Pro Val Thr Ile Val Leu
        435                 440                 445

Phe Val Met Ala Thr Pro Glu Thr Asp Lys Val Ala Glu Leu Ile Asp
    450                 455                 460

Val Ile Ala Leu Asn Arg Tyr Asn Gly Trp Tyr Phe Asp Gly Gly Asp
465                 470                 475                 480

Leu Glu Ala Ala Lys Val His Leu Arg Gln Glu Phe His Ala Trp Asn
                485                 490                 495

Lys Arg Cys Pro Gly Lys Pro Ile Met Ile Thr Glu Tyr Gly Ala Asp
            500                 505                 510

Thr Val Ala Gly Phe His Asp Ile Asp Pro Val Met Phe Thr Glu Glu
        515                 520                 525

Tyr Gln Val Glu Tyr Tyr Gln Ala Asn His Val Val Phe Asp Glu Phe
    530                 535                 540

Glu Asn Phe Val Gly Glu Gln Ala Trp Asn Phe Ala Asp Phe Ala Thr
545                 550                 555                 560

Ser Gln Gly Val Met Arg Val Gln Gly Asn Lys Lys Gly Val Phe Thr
                565                 570                 575

Arg Asp Arg Lys Pro Lys Leu Ala Ala His Val Phe Arg Glu Arg Trp
            580                 585                 590

Thr Asn Ile Pro Asp Phe Gly Tyr Lys Asn
        595                 600

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcaaaatcgg cgaaattc                                                       18

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 44
gacctcgcaa gcaatattgc gcgttg                                          26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gacctcgcaa tgtatattgc gcgttg                                          26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gacctcgcaa gatatattgc gcgttg                                          26

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gacctcgcaa gaaatattgc gcgttg                                          26

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gacctcgcaa ttcatattgc gcgttg                                          26

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gacctcgcaa catatattgc gcgttg                                          26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

```
gacctcgcaa atcatattgc gcgttg                                          26
```

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

```
gacctcgcaa aaaatattgc gcgttg                                          26
```

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
gacctcgcaa ctgatattgc gcgttg                                          26
```

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
gacctcgcaa atgatattgc gcgttg                                          26
```

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
gacctcgcaa aacatattgc gcgttg                                          26
```

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

```
gacctcgcaa ccgatattgc gcgttg                                          26
```

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

-continued gacctcgcaa cagatattgc gcgttg    26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gacctcgcaa cgtatattgc gcgttg    26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
gacctcgcaa gtgatattgc gcgttg    26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
gacctcgcaa tggatattgc gcgttg    26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
gacctcgcaa tacatattgc gcgttg    26

<210> SEQ ID NO 61
<211> LENGTH: 603
<212> TYPE: PRT
<213> ORGANISM: Escherichia coli

<400> SEQUENCE: 61

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

```
Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
            290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510
```

```
Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln His Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
                580                 585                 590

Phe Gly Glu Lys Pro Gln Gln Gly Gly Lys Gln
            595                 600

<210> SEQ ID NO 62
<211> LENGTH: 606
<212> TYPE: PRT
<213> ORGANISM: Escherichia coli

<400> SEQUENCE: 62

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285
```

```
Tyr Phe Thr Gly Phe Gly Arg His Glu Asp Ala Asp Leu Arg Gly Lys
        290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln His Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Gly Leu Cys
        595                 600                 605

<210> SEQ ID NO 63
<211> LENGTH: 608
<212> TYPE: PRT
<213> ORGANISM: Escherichia coli

<400> SEQUENCE: 63

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
```

```
            50                  55                  60
Gly Asn Val Trp Tyr Gln Arg Glu Val Phe Ile Pro Lys Gly Trp Ala
 65                  70                  75                  80

Gly Gln Arg Ile Val Leu Arg Phe Asp Ala Val Thr His Tyr Gly Lys
                     85                  90                  95

Val Trp Val Asn Asn Gln Glu Val Met Glu His Gln Gly Gly Tyr Thr
                    100                 105                 110

Pro Phe Glu Ala Asp Val Thr Pro Tyr Val Ile Ala Gly Lys Ser Val
                115                 120                 125

Arg Ile Thr Val Cys Val Asn Asn Glu Leu Asn Trp Gln Thr Ile Pro
            130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                    165                 170                 175

Tyr Thr Thr Pro Asn Thr Trp Val Asp Asp Ile Thr Val Val Thr His
                180                 185                 190

Val Ala Gln Asp Cys Asn His Ala Ser Val Asp Trp Gln Val Val Ala
                195                 200                 205

Asn Gly Asp Val Ser Val Glu Leu Arg Asp Ala Asp Gln Gln Val Val
210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                    245                 250                 255

Lys Ser Gln Thr Glu Cys Asp Ile Tyr Pro Leu Arg Val Gly Ile Arg
                260                 265                 270

Ser Val Ala Val Lys Gly Glu Gln Phe Leu Ile Asn His Lys Pro Phe
                275                 280                 285

Tyr Phe Thr Gly Phe Gly Arg His Glu Asp Ala Asp Leu Arg Gly Lys
                290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                    325                 330                 335

Met Leu Asp Trp Ala Asp Glu His Gly Ile Val Val Ile Asp Glu Thr
                340                 345                 350

Ala Ala Val Gly Phe Asn Leu Ser Leu Gly Ile Gly Phe Glu Ala Gly
                355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                    405                 410                 415

Arg Pro Gln Gly Ala Arg Glu Tyr Phe Ala Pro Leu Ala Glu Ala Thr
                420                 425                 430

Arg Lys Leu Asp Pro Thr Arg Pro Ile Thr Cys Val Asn Val Met Phe
                435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480
```

```
Ala Glu Lys Val Leu Glu Lys Glu Leu Leu Ala Trp Gln Glu Lys Leu
            485                 490                 495

His Gln Pro Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
            530                 535                 540

Gly Glu Gln Val Trp Asn Phe Ala Asp Phe Ala Thr Ser Gln His Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Gly Leu Cys Gly Arg
            595                 600                 605
```

<210> SEQ ID NO 64
<211> LENGTH: 603
<212> TYPE: PRT
<213> ORGANISM: Escherichia coli

<400> SEQUENCE: 64

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
            115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
            195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
```

```
                245                 250                 255
Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
            275                 280                 285

Tyr Phe Thr Gly Phe Gly Arg His Glu Asp Ala Asp Leu Arg Gly Lys
            290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Ala Val Asn Gly Glu Thr
            370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
            530                 535                 540

Gly Glu Gln Val Trp Asn Phe Ala Asp Phe Ala Thr Ser Gln Asn Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
            595                 600

<210> SEQ ID NO 65
<211> LENGTH: 606
<212> TYPE: PRT
<213> ORGANISM: Escherichia coli

<400> SEQUENCE: 65

Met Leu Arg Pro Val Glu Thr Pro Thr Arg Glu Ile Lys Lys Leu Asp
1               5                   10                  15
```

-continued

```
Gly Leu Trp Ala Phe Ser Leu Asp Arg Glu Asn Cys Gly Ile Asp Gln
             20                  25                  30
Arg Trp Trp Glu Ser Ala Leu Gln Glu Ser Arg Ala Ile Ala Val Pro
         35                  40                  45
Gly Ser Phe Asn Asp Gln Phe Ala Asp Ala Asp Ile Arg Asn Tyr Ala
     50                  55                  60
Gly Asn Val Trp Tyr Gln Arg Glu Val Phe Ile Pro Lys Gly Trp Ala
 65                  70                  75                  80
Gly Gln Arg Ile Val Leu Arg Phe Asp Ala Val Thr His Tyr Gly Lys
                 85                  90                  95
Val Trp Val Asn Asn Gln Glu Val Met Glu His Gln Gly Gly Tyr Thr
            100                 105                 110
Pro Phe Glu Ala Asp Val Thr Pro Tyr Val Ile Ala Gly Lys Ser Val
        115                 120                 125
Arg Ile Thr Val Cys Val Asn Asn Glu Leu Asn Trp Gln Thr Ile Pro
    130                 135                 140
Pro Gly Met Val Ile Thr Asp Glu Asn Gly Lys Lys Lys Gln Ser Tyr
145                 150                 155                 160
Phe His Asp Phe Phe Asn Tyr Ala Gly Ile His Arg Ser Val Met Leu
                165                 170                 175
Tyr Thr Thr Pro Asn Thr Trp Val Asp Asp Ile Thr Val Val Thr His
            180                 185                 190
Val Ala Gln Asp Cys Asn His Ala Ser Val Asp Trp Gln Val Val Ala
        195                 200                 205
Asn Gly Asp Val Ser Val Glu Leu Arg Asp Ala Asp Gln Gln Val Val
    210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
Lys Ser Gln Thr Glu Cys Asp Ile Tyr Pro Leu Arg Val Gly Ile Arg
            260                 265                 270
Ser Val Ala Val Lys Gly Glu Gln Phe Leu Ile Asn His Lys Pro Phe
        275                 280                 285
Tyr Phe Thr Gly Phe Gly Arg His Glu Asp Ala Asp Leu Arg Gly Lys
    290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
            340                 345                 350
Ala Ala Val Gly Phe Asn Leu Ser Leu Gly Ile Gly Phe Glu Ala Gly
        355                 360                 365
Asn Lys Pro Lys Glu Leu Tyr Ser Glu Ala Val Asn Gly Glu Thr
    370                 375                 380
Gln Gln Ala His Leu Gln Ala Ile Lys Glu Leu Ile Ala Arg Asp Lys
385                 390                 395                 400
Asn His Pro Ser Val Met Trp Ser Ile Ala Asn Glu Pro Asp Thr
                405                 410                 415
Arg Pro Gln Gly Ala Arg Glu Tyr Phe Ala Pro Leu Ala Glu Ala Thr
            420                 425                 430
Arg Lys Leu Asp Pro Thr Arg Pro Ile Thr Cys Val Asn Val Met Phe
```

```
              435                 440                 445
Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
                500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
        530                 535                 540

Gly Glu Gln Val Trp Asn Phe Ala Asp Phe Ala Thr Ser Gln Asn Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Gly Leu Cys
        595                 600                 605
```

<210> SEQ ID NO 66
<211> LENGTH: 608
<212> TYPE: PRT
<213> ORGANISM: Escherichia coli

<400> SEQUENCE: 66

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
                20                  25                  30

Arg Trp Trp Glu Ser Ala Leu Gln Glu Ser Arg Ala Ile Ala Val Pro
            35                  40                  45

Gly Ser Phe Asn Asp Gln Phe Ala Asp Ala Asp Ile Arg Asn Tyr Ala
        50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
                100                 105                 110

Pro Phe Glu Ala Asp Val Thr Pro Tyr Val Ile Ala Gly Lys Ser Val
            115                 120                 125

Arg Ile Thr Val Cys Val Asn Asn Glu Leu Asn Trp Gln Thr Ile Pro
        130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205
```

```
Asn Gly Asp Val Ser Val Glu Leu Arg Asp Ala Asp Gln Gln Val Val
210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
Lys Ser Gln Thr Glu Cys Asp Ile Tyr Pro Leu Arg Val Gly Ile Arg
            260                 265                 270
Ser Val Ala Val Lys Gly Glu Gln Phe Leu Ile Asn His Lys Pro Phe
        275                 280                 285
Tyr Phe Thr Gly Phe Gly Arg His Glu Asp Ala Asp Leu Arg Gly Lys
    290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
            340                 345                 350
Ala Ala Val Gly Phe Asn Leu Ser Leu Gly Ile Gly Phe Glu Ala Gly
        355                 360                 365
Asn Lys Pro Lys Glu Leu Tyr Ser Glu Glu Ala Val Asn Gly Glu Thr
    370                 375                 380
Gln Gln Ala His Leu Gln Ala Ile Lys Glu Leu Ile Ala Arg Asp Lys
385                 390                 395                 400
Asn His Pro Ser Val Val Met Trp Ser Ile Ala Asn Glu Pro Asp Thr
                405                 410                 415
Arg Pro Gln Gly Ala Arg Glu Tyr Phe Ala Pro Leu Ala Glu Ala Thr
            420                 425                 430
Arg Lys Leu Asp Pro Thr Arg Pro Ile Thr Cys Val Asn Val Met Phe
        435                 440                 445
Cys Asp Ala His Thr Asp Thr Ile Ser Asp Leu Phe Asp Val Leu Cys
    450                 455                 460
Leu Asn Arg Tyr Tyr Gly Trp Tyr Val Gln Ser Gly Asp Leu Glu Thr
465                 470                 475                 480
Ala Glu Lys Val Leu Glu Lys Glu Leu Leu Ala Trp Gln Glu Lys Leu
                485                 490                 495
His Gln Pro Ile Ile Ile Thr Glu Tyr Gly Val Asp Thr Leu Ala Gly
            500                 505                 510
Leu His Ser Met Tyr Thr Asp Met Trp Ser Glu Glu Tyr Gln Cys Ala
        515                 520                 525
Trp Leu Asp Met Tyr His Arg Val Phe Asp Arg Val Ser Ala Val Val
    530                 535                 540
Gly Glu Gln Val Trp Asn Phe Ala Asp Phe Ala Thr Ser Gln Asn Ile
545                 550                 555                 560
Leu Arg Val Gly Gly Asn Lys Lys Gly Ile Phe Thr Arg Asp Arg Lys
                565                 570                 575
Pro Lys Ser Ala Ala Phe Leu Leu Gln Lys Arg Trp Thr Gly Met Asn
            580                 585                 590
Phe Gly Glu Lys Pro Gln Gln Gly Gly Lys Gln Gly Leu Cys Gly Arg
        595                 600                 605

<210> SEQ ID NO 67
<211> LENGTH: 608
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (607)..(608)
<223> OTHER INFORMATION: Any amino acid

<400> SEQUENCE: 67

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365
```

-continued

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Ser Ser Cys Xaa Xaa
        595                 600                 605

<210> SEQ ID NO 68
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (607)..(608)
<223> OTHER INFORMATION: Any amino acid

<400> SEQUENCE: 68

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

```
Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
                180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
        210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
                260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
        290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Ile Asp Glu Thr
                340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
        450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
                500                 505                 510

Leu His Ser Met Tyr Thr Asp Met Trp Ser Glu Glu Tyr Gln Cys Ala
```

```
              515                 520                 525
Trp Leu Asp Met Tyr His Arg Val Phe Asp Arg Val Ser Ala Val Val
        530                 535                 540
Gly Glu Gln Val Trp Asn Phe Ala Asp Phe Ala Thr Ser Gln Ser Ile
545                 550                 555                 560
Leu Arg Val Gly Gly Asn Lys Lys Gly Ile Phe Thr Arg Asp Arg Lys
                565                 570                 575
Pro Lys Ser Ala Ala Phe Leu Leu Gln Lys Arg Trp Thr Gly Met Asn
            580                 585                 590
Phe Gly Glu Lys Pro Gln Gln Gly Gly Lys Gln Glu Glu Cys Xaa Xaa
        595                 600                 605

<210> SEQ ID NO 69
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (607)..(608)
<223> OTHER INFORMATION: Any amino acid

<400> SEQUENCE: 69

Met Leu Arg Pro Val Glu Thr Pro Thr Arg Glu Ile Lys Lys Leu Asp
1               5                   10                  15
Gly Leu Trp Ala Phe Ser Leu Asp Arg Glu Asn Cys Gly Ile Asp Gln
            20                  25                  30
Arg Trp Trp Glu Ser Ala Leu Gln Glu Ser Arg Ala Ile Ala Val Pro
        35                  40                  45
Gly Ser Phe Asn Asp Gln Phe Ala Asp Ala Asp Ile Arg Asn Tyr Ala
    50                  55                  60
Gly Asn Val Trp Tyr Gln Arg Glu Val Phe Ile Pro Lys Gly Trp Ala
65                  70                  75                  80
Gly Gln Arg Ile Val Leu Arg Phe Asp Ala Val Thr His Tyr Gly Lys
                85                  90                  95
Val Trp Val Asn Asn Gln Glu Val Met Glu His Gln Gly Gly Tyr Thr
            100                 105                 110
Pro Phe Glu Ala Asp Val Thr Pro Tyr Val Ile Ala Gly Lys Ser Val
        115                 120                 125
Arg Ile Thr Val Cys Val Asn Asn Glu Leu Asn Trp Gln Thr Ile Pro
    130                 135                 140
Pro Gly Met Val Ile Thr Asp Glu Asn Gly Lys Lys Lys Gln Ser Tyr
145                 150                 155                 160
Phe His Asp Phe Phe Asn Tyr Ala Gly Ile His Arg Ser Val Met Leu
                165                 170                 175
Tyr Thr Thr Pro Asn Thr Trp Val Asp Asp Ile Thr Val Val Thr His
            180                 185                 190
Val Ala Gln Asp Cys Asn His Ala Ser Val Asp Trp Gln Val Val Ala
        195                 200                 205
Asn Gly Asp Val Ser Val Glu Leu Arg Asp Ala Asp Gln Gln Val Val
    210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
```

```
Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Lys Lys Cys Xaa Xaa
        595                 600                 605

<210> SEQ ID NO 70
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (607)..(608)
<223> OTHER INFORMATION: Any amino acid
```

<400> SEQUENCE: 70

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr

```
            405                 410                 415
Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
            485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
            565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Ala Ala Cys Xaa Xaa
            595                 600                 605
```

<210> SEQ ID NO 71
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (607)..(608)
<223> OTHER INFORMATION: Any amino acid

<400> SEQUENCE: 71

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140
```

```
Pro Gly Met Val Ile Thr Asp Glu Asn Gly Lys Lys Gln Ser Tyr
145                 150                 155                 160

Phe His Asp Phe Phe Asn Tyr Ala Gly Ile His Arg Ser Val Met Leu
            165                 170                 175

Tyr Thr Thr Pro Asn Thr Trp Val Asp Asp Ile Thr Val Thr His
                180                 185                 190

Val Ala Gln Asp Cys Asn His Ala Ser Val Asp Trp Gln Val Val Ala
            195                 200                 205

Asn Gly Asp Val Ser Val Glu Leu Arg Asp Ala Asp Gln Gln Val Val
        210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Ser Ile
545                 550                 555                 560
```

```
Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Trp Trp Cys Xaa Xaa
        595                 600                 605
```

<210> SEQ ID NO 72
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (607)..(608)
<223> OTHER INFORMATION: Any amino acid

<400> SEQUENCE: 72

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
```

```
            290                 295                 300
Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Pro Cys Xaa Xaa
        595                 600                 605
```

<210> SEQ ID NO 73
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (608)..(609)
<223> OTHER INFORMATION: Any amino acid

<400> SEQUENCE: 73

```
Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30
```

```
Arg Trp Trp Glu Ser Ala Leu Gln Glu Ser Arg Ala Ile Ala Val Pro
        35                  40                  45
Gly Ser Phe Asn Asp Gln Phe Ala Asp Ala Asp Ile Arg Asn Tyr Ala
    50                  55                  60
Gly Asn Val Trp Tyr Gln Arg Glu Val Phe Ile Pro Lys Gly Trp Ala
65                  70                  75                  80
Gly Gln Arg Ile Val Leu Arg Phe Asp Ala Val Thr His Tyr Gly Lys
                85                  90                  95
Val Trp Val Asn Asn Gln Glu Val Met Glu His Gln Gly Gly Tyr Thr
                100                 105                 110
Pro Phe Glu Ala Asp Val Thr Pro Tyr Val Ile Ala Gly Lys Ser Val
            115                 120                 125
Arg Ile Thr Val Cys Val Asn Asn Glu Leu Asn Trp Gln Thr Ile Pro
        130                 135                 140
Pro Gly Met Val Ile Thr Asp Glu Asn Gly Lys Lys Lys Gln Ser Tyr
145                 150                 155                 160
Phe His Asp Phe Phe Asn Tyr Ala Gly Ile His Arg Ser Val Met Leu
                165                 170                 175
Tyr Thr Thr Pro Asn Thr Trp Val Asp Asp Ile Thr Val Val Thr His
                180                 185                 190
Val Ala Gln Asp Cys Asn His Ala Ser Val Asp Trp Gln Val Val Ala
        195                 200                 205
Asn Gly Asp Val Ser Val Glu Leu Arg Asp Ala Asp Gln Gln Val Val
        210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
Lys Ser Gln Thr Glu Cys Asp Ile Tyr Pro Leu Arg Val Gly Ile Arg
                260                 265                 270
Ser Val Ala Val Lys Gly Glu Gln Phe Leu Ile Asn His Lys Pro Phe
        275                 280                 285
Tyr Phe Thr Gly Phe Gly Arg His Glu Asp Ala Asp Leu Arg Gly Lys
        290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
                340                 345                 350
Ala Ala Val Gly Phe Asn Leu Ser Leu Gly Ile Gly Phe Glu Ala Gly
        355                 360                 365
Asn Lys Pro Lys Glu Leu Tyr Ser Glu Glu Ala Val Asn Gly Glu Thr
        370                 375                 380
Gln Gln Ala His Leu Gln Ala Ile Lys Glu Leu Ile Ala Arg Asp Lys
385                 390                 395                 400
Asn His Pro Ser Val Val Met Trp Ser Ile Ala Asn Glu Pro Asp Thr
                405                 410                 415
Arg Pro Gln Gly Ala Arg Glu Tyr Phe Ala Pro Leu Ala Glu Ala Thr
                420                 425                 430
Arg Lys Leu Asp Pro Thr Arg Pro Ile Thr Cys Val Asn Val Met Phe
            435                 440                 445
```

```
Cys Asp Ala His Thr Asp Thr Ile Ser Asp Leu Phe Asp Val Leu Cys
    450                 455                 460
Leu Asn Arg Tyr Tyr Gly Trp Tyr Val Gln Ser Gly Asp Leu Glu Thr
465                 470                 475                 480
Ala Glu Lys Val Leu Glu Lys Glu Leu Leu Ala Trp Gln Glu Lys Leu
                485                 490                 495
His Gln Pro Ile Ile Ile Thr Glu Tyr Gly Val Asp Thr Leu Ala Gly
            500                 505                 510
Leu His Ser Met Tyr Thr Asp Met Trp Ser Glu Tyr Gln Cys Ala
        515                 520                 525
Trp Leu Asp Met Tyr His Arg Val Phe Asp Arg Val Ser Ala Val Val
    530                 535                 540
Gly Glu Gln Val Trp Asn Phe Ala Asp Phe Ala Thr Ser Gln Ser Ile
545                 550                 555                 560
Leu Arg Val Gly Gly Asn Lys Lys Gly Ile Phe Thr Arg Asp Arg Lys
                565                 570                 575
Pro Lys Ser Ala Ala Phe Leu Leu Gln Lys Arg Trp Thr Gly Met Asn
            580                 585                 590
Phe Gly Glu Lys Pro Gln Gln Gly Lys Gln Gly Leu Gly Cys Xaa
        595                 600                 605
Xaa
```

<210> SEQ ID NO 74
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (609)..(610)
<223> OTHER INFORMATION: Any amino acid

<400> SEQUENCE: 74

```
Met Leu Arg Pro Val Glu Thr Pro Thr Arg Glu Ile Lys Lys Leu Asp
1               5                   10                  15
Gly Leu Trp Ala Phe Ser Leu Asp Arg Glu Asn Cys Gly Ile Asp Gln
                20                  25                  30
Arg Trp Trp Glu Ser Ala Leu Gln Glu Ser Arg Ala Ile Ala Val Pro
            35                  40                  45
Gly Ser Phe Asn Asp Gln Phe Ala Asp Ala Asp Ile Arg Asn Tyr Ala
        50                  55                  60
Gly Asn Val Trp Tyr Gln Arg Glu Val Phe Ile Pro Lys Gly Trp Ala
65                  70                  75                  80
Gly Gln Arg Ile Val Leu Arg Phe Asp Ala Val Thr His Tyr Gly Lys
                85                  90                  95
Val Trp Val Asn Asn Gln Glu Val Met Glu His Gln Gly Gly Tyr Thr
            100                 105                 110
Pro Phe Glu Ala Asp Val Thr Pro Tyr Val Ile Ala Gly Lys Ser Val
        115                 120                 125
Arg Ile Thr Val Cys Val Asn Asn Glu Leu Asn Trp Gln Thr Ile Pro
    130                 135                 140
Pro Gly Met Val Ile Thr Asp Glu Asn Gly Lys Lys Lys Gln Ser Tyr
145                 150                 155                 160
Phe His Asp Phe Phe Asn Tyr Ala Gly Ile His Arg Ser Val Met Leu
                165                 170                 175
```

```
Tyr Thr Thr Pro Asn Thr Trp Val Asp Asp Ile Thr Val Thr His
            180                 185                 190
Val Ala Gln Asp Cys Asn His Ala Ser Val Asp Trp Gln Val Val Ala
            195                 200                 205
Asn Gly Asp Val Ser Val Glu Leu Arg Asp Ala Asp Gln Gln Val Val
210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
            245                 250                 255
Lys Ser Gln Thr Glu Cys Asp Ile Tyr Pro Leu Arg Val Gly Ile Arg
            260                 265                 270
Ser Val Ala Val Lys Gly Glu Gln Phe Leu Ile Asn His Lys Pro Phe
            275                 280                 285
Tyr Phe Thr Gly Phe Gly Arg His Glu Asp Ala Asp Leu Arg Gly Lys
            290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
            325                 330                 335
Met Leu Asp Trp Ala Asp Glu His Gly Ile Val Val Ile Asp Glu Thr
            340                 345                 350
Ala Ala Val Gly Phe Asn Leu Ser Leu Gly Ile Gly Phe Glu Ala Gly
            355                 360                 365
Asn Lys Pro Lys Glu Leu Tyr Ser Glu Glu Ala Val Asn Gly Glu Thr
            370                 375                 380
Gln Gln Ala His Leu Gln Ala Ile Lys Glu Leu Ile Ala Arg Asp Lys
385                 390                 395                 400
Asn His Pro Ser Val Val Met Trp Ser Ile Ala Asn Glu Pro Asp Thr
            405                 410                 415
Arg Pro Gln Gly Ala Arg Glu Tyr Phe Ala Pro Leu Ala Glu Ala Thr
            420                 425                 430
Arg Lys Leu Asp Pro Thr Arg Pro Ile Thr Cys Val Asn Val Met Phe
            435                 440                 445
Cys Asp Ala His Thr Asp Thr Ile Ser Asp Leu Phe Asp Val Leu Cys
450                 455                 460
Leu Asn Arg Tyr Tyr Gly Trp Tyr Val Gln Ser Gly Asp Leu Glu Thr
465                 470                 475                 480
Ala Glu Lys Val Leu Glu Lys Glu Leu Leu Ala Trp Gln Glu Lys Leu
            485                 490                 495
His Gln Pro Ile Ile Ile Thr Glu Tyr Gly Val Asp Thr Leu Ala Gly
            500                 505                 510
Leu His Ser Met Tyr Thr Asp Met Trp Ser Glu Glu Tyr Gln Cys Ala
            515                 520                 525
Trp Leu Asp Met Tyr His Arg Val Phe Asp Arg Val Ser Ala Val Val
            530                 535                 540
Gly Glu Gln Val Trp Asn Phe Ala Asp Phe Ala Thr Ser Gln Ser Ile
545                 550                 555                 560
Leu Arg Val Gly Gly Asn Lys Lys Gly Ile Phe Thr Arg Asp Arg Lys
            565                 570                 575
Pro Lys Ser Ala Ala Phe Leu Leu Gln Lys Arg Trp Thr Gly Met Asn
            580                 585                 590
```

Phe Gly Glu Lys Pro Gln Gln Gly Gly Lys Gln Gly Leu Gly Gly Cys
             595                 600                 605

Xaa Xaa
    610

<210> SEQ ID NO 75
<211> LENGTH: 611
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (610)..(611)
<223> OTHER INFORMATION: Any amino acid

<400> SEQUENCE: 75

Met Leu Arg Pro Val Glu Thr Pro Thr Arg Glu Ile Lys Lys Leu Asp
1               5                  10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp

```
            305                 310                 315                 320
Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
                355                 360                 365

Asn Lys Pro Lys Glu Leu Tyr Ser Glu Ala Val Asn Gly Glu Thr
            370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
                435                 440                 445

Cys Asp Ala His Thr Asp Thr Ile Ser Asp Leu Phe Asp Val Leu Cys
            450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
            530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Gly Leu Gly Gly Gly
                595                 600                 605

Cys Xaa Xaa
    610

<210> SEQ ID NO 76
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (611)..(612)
<223> OTHER INFORMATION: Any amino acid

<400> SEQUENCE: 76

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
                20                  25                  30
```

```
Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
                100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
        130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
                180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
        210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
                260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
        290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Ile Asp Glu Thr
                340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
        370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
        405                 410                 415

Arg Pro Gln Gly Ala Arg Glu Tyr Phe Ala Pro Leu Ala Glu Ala Thr
        420                 425                 430

Arg Lys Leu Asp Pro Thr Arg Pro Ile Thr Cys Val Asn Val Met Phe
        435                 440                 445
```

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Lys Gln Gly Leu Gly Gly Gly
        595                 600                 605

Gly Cys Xaa Xaa
    610

<210> SEQ ID NO 77
<211> LENGTH: 613
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (612)..(613)
<223> OTHER INFORMATION: Any amino acid

<400> SEQUENCE: 77

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu

-continued

```
            165                 170                 175
Tyr Thr Thr Pro Asn Thr Trp Val Asp Asp Ile Thr Val Thr His
                180                 185                 190
Val Ala Gln Asp Cys Asn His Ala Ser Val Asp Trp Gln Val Ala
                195                 200                 205
Asn Gly Asp Val Ser Val Glu Leu Arg Asp Ala Asp Gln Gln Val Val
210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
Lys Ser Gln Thr Glu Cys Asp Ile Tyr Pro Leu Arg Val Gly Ile Arg
                260                 265                 270
Ser Val Ala Val Lys Gly Glu Gln Phe Leu Ile Asn His Lys Pro Phe
                275                 280                 285
Tyr Phe Thr Gly Phe Gly Arg His Glu Asp Ala Asp Leu Arg Gly Lys
                290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
                340                 345                 350
Ala Ala Val Gly Phe Asn Leu Ser Leu Gly Ile Gly Phe Glu Ala Gly
                355                 360                 365
Asn Lys Pro Lys Glu Leu Tyr Ser Glu Glu Ala Val Asn Gly Glu Thr
                370                 375                 380
Gln Gln Ala His Leu Gln Ala Ile Lys Glu Leu Ile Ala Arg Asp Lys
385                 390                 395                 400
Asn His Pro Ser Val Val Met Trp Ser Ile Ala Asn Glu Pro Asp Thr
                405                 410                 415
Arg Pro Gln Gly Ala Arg Glu Tyr Phe Ala Pro Leu Ala Glu Ala Thr
                420                 425                 430
Arg Lys Leu Asp Pro Thr Arg Pro Ile Thr Cys Val Asn Val Met Phe
                435                 440                 445
Cys Asp Ala His Thr Asp Thr Ile Ser Asp Leu Phe Asp Val Leu Cys
450                 455                 460
Leu Asn Arg Tyr Tyr Gly Trp Tyr Val Gln Ser Gly Asp Leu Glu Thr
                470                 475                 480
Ala Glu Lys Val Leu Glu Lys Glu Leu Leu Ala Trp Gln Glu Lys Leu
                485                 490                 495
His Gln Pro Ile Ile Ile Thr Glu Tyr Gly Val Asp Thr Leu Ala Gly
                500                 505                 510
Leu His Ser Met Tyr Thr Asp Met Trp Ser Glu Glu Tyr Gln Cys Ala
                515                 520                 525
Trp Leu Asp Met Tyr His Arg Val Phe Asp Arg Val Ser Ala Val Val
                530                 535                 540
Gly Glu Gln Val Trp Asn Phe Ala Asp Phe Ala Thr Ser Gln Ser Ile
545                 550                 555                 560
Leu Arg Val Gly Gly Asn Lys Lys Gly Ile Phe Thr Arg Asp Arg Lys
                565                 570                 575
Pro Lys Ser Ala Ala Phe Leu Leu Gln Lys Arg Trp Thr Gly Met Asn
                580                 585                 590
```

-continued

Phe Gly Glu Lys Pro Gln Gln Gly Gly Lys Gln Gly Leu Gly Gly Gly
            595                 600                 605

Gly Gly Cys Xaa Xaa
    610

<210> SEQ ID NO 78
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (613)..(614)
<223> OTHER INFORMATION: Any amino acid

<400> SEQUENCE: 78

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
            325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
            405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
            485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
            565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Lys Gln Gly Leu Gly Gly Gly
            595                 600                 605

Gly Gly Gly Cys Xaa Xaa
610

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
agcagctgcg gccggtagaa aggag                                          25

<210> SEQ ID NO 80
<211> LENGTH: 25
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 80
gaagaatgcg gccggtagaa aggag                                           25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
aaaaaatgcg gccggtagaa aggag                                           25

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gcggcgtgcg gccggtagaa aggag                                           25

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tggtggtgcg gccggtagaa aggag                                           25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccgccgtgcg gccggtagaa aggag                                           25

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ttgtttgcct ccctgctg                                                   18

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 86
ggctgcggcc ggtagaaagg ag                                          22

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggcggctgcg gccggtagaa aggag                                       25

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggcggcggct gcggccggta gaaaggag                                    28

<210> SEQ ID NO 89
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ggcggcggcg gctgcggccg gtagaaagga g                                31

<210> SEQ ID NO 90
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ggcggcggcg gcggctgcgg ccggtagaaa ggag                             34

<210> SEQ ID NO 91
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggcggcggcg gcggcggctg cggccggtag aaaggag                          37

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 92
taggccttgt ttgcctccc                                                                                                  19

<210> SEQ ID NO 93
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (559)..(559)
<223> OTHER INFORMATION: Ser, Thr, His or Asn
<220> FEATURE:
<221> NAME/KEY: MOD_RES
<222> LOCATION: (604)..(611)
<223> OTHER INFORMATION: Any amino acid
<220> FEATURE:
<221> NAME/KEY: MISC_FEATURE
<222> LOCATION: (604)..(611)
<223> OTHER INFORMATION: This region may encompass 2-8 residues, wherein
      some positions may be absent
<220> FEATURE:
<221> NAME/KEY: MOD_RES
<222> LOCATION: (613)..(614)
<223> OTHER INFORMATION: Any amino acid
<220> FEATURE:
<221> NAME/KEY: MISC_FEATURE
<222> LOCATION: (613)..(614)
<223> OTHER INFORMATION: This region may encompass 0-2 residues, wherein
      some positions may be absent

<400> SEQUENCE: 93

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

```
Ala Thr Gly Gln Gly Thr Ser Gly Thr Leu Gln Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
                260                 265                 270

Ser Val Ala Val Lys Gly Glu Gln Phe Leu Ile Asn His Lys Pro Phe
                275                 280                 285

Tyr Phe Thr Gly Phe Gly Arg His Glu Asp Ala Asp Leu Arg Gly Lys
                290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
                340                 345                 350

Ala Ala Val Gly Phe Asn Leu Ser Leu Gly Ile Gly Phe Glu Ala Gly
                355                 360                 365

Asn Lys Pro Lys Glu Leu Tyr Ser Glu Ala Val Asn Gly Glu Thr
                370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
                420                 425                 430

Arg Lys Leu Asp Pro Thr Arg Pro Ile Thr Cys Val Asn Val Met Phe
                435                 440                 445

Cys Asp Ala His Thr Asp Thr Ile Ser Asp Leu Phe Asp Val Leu Cys
                450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
                500                 505                 510

Leu His Ser Met Tyr Thr Asp Met Trp Ser Glu Glu Tyr Gln Cys Ala
                515                 520                 525

Trp Leu Asp Met Tyr His Arg Val Phe Asp Arg Val Ser Ala Val Val
                530                 535                 540

Gly Glu Gln Val Trp Asn Phe Ala Asp Phe Ala Thr Ser Gln Xaa Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
                580                 585                 590

Phe Gly Glu Lys Pro Gln Gln Gly Gly Lys Gln Xaa Xaa Xaa Xaa
                595                 600                 605

Xaa Xaa Xaa Cys Xaa Xaa
        610

<210> SEQ ID NO 94
<211> LENGTH: 608
```

```
<212> TYPE: PRT
<213> ORGANISM: Unknown
<220> FEATURE:
<223> OTHER INFORMATION: Description of Unknown: BGUS polypeptide

<400> SEQUENCE: 94

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380
```

```
Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
            405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
            450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
            485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
            530                 535                 540

Gly Glu Gln Val Trp Asn Phe Ala Asp Phe Ala Thr Ser Gln Ser Ile
545                 550                 555                 560

Leu Arg Val Gly Gly Asn Lys Lys Gly Ile Phe Thr Arg Asp Arg Lys
            565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln Gly Leu Cys Gly Arg
            595                 600                 605

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(8)
<223> OTHER INFORMATION: Any amino acid
<220> FEATURE:
<221> NAME/KEY: MISC_FEATURE
<222> LOCATION: (1)..(8)
<223> OTHER INFORMATION: This region may encompass 2-8 residues, wherein
      some positions may be absent
<220> FEATURE:
<221> NAME/KEY: MOD_RES
<222> LOCATION: (10)..(11)
<223> OTHER INFORMATION: Any amino acid
<220> FEATURE:
<221> NAME/KEY: MISC_FEATURE
<222> LOCATION: (10)..(11)
<223> OTHER INFORMATION: This region may encompass 0-2 residues, wherein
      some positions may be absent

<400> SEQUENCE: 95

Xaa Xaa Xaa Xaa Xaa Xaa Xaa Xaa Cys Xaa Xaa
1               5                   10
```

```
<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Leu Cys Gly Arg
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Any amino acid

<400> SEQUENCE: 97

Gly Leu Gly Cys Xaa Xaa
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Any amino acid

<400> SEQUENCE: 98

Gly Leu Gly Gly Cys Xaa Xaa
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Any amino acid

<400> SEQUENCE: 99

Gly Leu Gly Gly Gly Cys Xaa Xaa
1               5

<210> SEQ ID NO 100
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Any amino acid

<400> SEQUENCE: 100

Gly Leu Gly Gly Gly Gly Cys Xaa Xaa
1               5

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: Any amino acid

<400> SEQUENCE: 101

Gly Leu Gly Gly Gly Gly Gly Cys Xaa Xaa
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(11)
<223> OTHER INFORMATION: Any amino acid

<400> SEQUENCE: 102

Gly Leu Gly Gly Gly Gly Gly Gly Cys Xaa Xaa
1               5                   10

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Leu Cys Gly
1

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Ser Gly Arg
1               5
```

MUTANT β-GLUCURONIDASE ENZYMES WITH ENHANCED ENZYMATIC ACTIVITY

RELATED APPLICATIONS

This application claims priority to and the benefit of U.S. provisional patent application No. 62/056,800, filed on Sep. 29, 2014, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 10, 2015, is named IMJ_001_Sequence.txt and is 194,531 bytes in size.

BACKGROUND OF THE INVENTION

In mammals, glucuronidation is one of the principle means of detoxifying or inactivating compounds using the UDP glucuronyl transferase system. Compounds are conjugated by the glucoronyl transferase system to form glucuronides, which are then secreted in urine or into the lower intestine in bile. Furthermore, microorganisms in the gut, such as *Escherichia coli*, have evolved to utilize the excreted β-glucuronides as a carbon source. The β-glucuronidase (BGUS) enzyme catalyzes the hydrolysis of a wide variety of β-glucuronides. Thus, BGUS enzyme activity been reported in those organisms that utilize glucuronidation as a detoxification pathway, as well as in some of their endogenous microbe populations. All vertebrates and many mollusks, as well as certain bacteria, exhibit BGUS enzyme activity, whereas insects and plants that utilize a different detoxification pathway typically do not exhibit BGUS enzyme activity.

Given the key role of glucuronidation in detoxification of compounds, the BGUS enzyme has been used for detection of drugs in bodily samples, such as to detect the presence of illicit drugs in bodily samples of criminal suspects. For example, a bodily sample can be tested for the presence of a suspected drug by detecting the hydrolysis of the glucuronide form of the drug by BGUS.

Commercially available preparations of BGUS enzyme, for use for example in drug testing, include crude extract forms of the *E. coli*, snail and abalone versions of the enzyme. While these preparations are effective in hydrolyzing glucuronides, they typically include other proteins in addition to the BGUS, which may interfere with enzyme activity. Moreover, importantly, their level of enzyme activity is such that they typically require at least several hours (e.g., three hours or more) to analyze a sample. Including sample preparation time and analysis time, this means that evaluation of a drug sample typically can take at least two days using currently commercially available BGUS preparations.

Accordingly, there is a need for BGUS enzymes with enhanced activity that are more efficient for use in drug testing.

SUMMARY OF THE INVENTION

The invention provides mutant forms of BGUS enzymes that exhibit enhanced enzymatic activity as compared to wild type enzyme. Moreover, mutant forms of BGUS described herein exhibit higher thermal stability than the wild type enzyme. The enzymes of the invention advantageously allow for accurate analysis of bodily samples for the presence of drugs in 30 minutes or less, as compared to the several hours needed using the current commercially available enzyme preparations, thereby allowing for completion of analyses within a shorter time frame than previously possible. Furthermore, the mutant enzymes of the invention are produced recombinantly and thus can be prepared in a highly purified form without contaminating non-BGUS proteins and with a higher temperature stability.

In particular, it has been discovered that the single substitution of amino acid residue G559 in the *E. coli* BGUS wild type sequence (shown in SEQ ID NO: 18) with an amino acid having a side chain with a non-aromatic hydroxyl group, such as a serine (G559S) or threonine (G559T), or with histidine (G559H) or asparagine (G559N), leads to significantly increased enzymatic activity as compared to the wild type enzyme. Moreover, addition of a cysteine residue at the C-terminal end of the enzyme has been found to enhance the thermostability of the enzyme. For example, the following sequence can be added at the C-terminal end of the enzyme: $Xaa_{2-8}$-Cys-$Xaa_{0-2}$, wherein Xaa=any amino acid. Still further, a loop region at amino acid residues F365-K370 of the *E. coli* BGUS wild type sequence (shown in SEQ ID NO: 18) has been found to be important for imparting efficient hydrolysis of codeine glucuronide substrates.

Accordingly, in one aspect, the invention pertains to a packaged formulation comprising a container comprising a preparation of a β-glucuronidase enzyme, wherein:
 (i) the β-glucuronidase enzyme comprises a mutation consisting of a substitution of an amino acid corresponding to G559 in SEQ ID NO: 18 with an amino acid comprising a side chain comprising a non-aromatic hydroxyl group or histidine or asparagine; and
 (ii) the preparation of β-glucuronidase enzyme has an enzymatic activity of at least 5,000 Units/ml or 5,000 Units/mg.

Preferably, the β-glucuronidase enzyme has an enzymatic activity of at least 10,000 Units/ml or 10,000 Units/mg, more preferably at least 25,000 Units/ml or 25,000 Units/mg and even more preferably at least 50,000 Units/ml or 50,000 units/mg.

In one embodiment, the β-glucuronidase enzyme comprises a mutation consisting of a substitution of an amino acid corresponding to G559 in SEQ ID NO: 18 with serine. Preferably, the enzyme having the G559S substitution has an amino acid sequence as shown in SEQ ID NO: 19. In another embodiment, the β-glucuronidase enzyme comprises a mutation consisting of a substitution of an amino acid corresponding to G559 in SEQ ID NO: 18 with threonine. Preferably, the enzyme having the G559T substitution has an amino acid sequence as shown in SEQ ID NO: 20. In another embodiment, the β-glucuronidase enzyme comprises a mutation consisting of a substitution of an amino acid corresponding to G559 in SEQ ID NO: 18 with histidine. In another embodiment, the β-glucuronidase enzyme comprises a mutation consisting of a substitution of an amino acid corresponding to G559 in SEQ ID NO: 18 with asparagine.

The enzyme preparation in the packaged formulation can be, for example, an aqueous solution or a lyophilized preparation. In one embodiment, the β-glucuronidase enzyme is in an aqueous solution with an enzymatic activity of at least 50,000 Units/ml. In another embodiment, the β-glucuronidase enzyme is in a lyophilized preparation with an enzymatic activity of at least 50,000 Units/mg. In yet another embodiment, the β-glucuronidase enzyme is in a lyophilized preparation that when reconstituted as an aqueous solution has an enzymatic activity of at least 50,000 Units/ml.

In one embodiment, the preparation is stable at least six months at 2-8° C. In another embodiment, the preparation lacks detectable sulfatase activity.

Preferably, the β-glucuronidase enzyme is from a bacteria, more preferably from *Escherichia coli*, even more preferably from *Escherichia coli* K12 strain. In another embodiment, the β-glucuronidase enzyme is from a mollusk, such as a snail (preferably *Helix pomatia* or *Helix aspersa*) or an abalone (preferably *Haliotis rufescens*). In yet another embodiment, the β-glucuronidase enzyme is from a human.

In another aspect, the invention provides a method of hydrolyzing a substrate comprising a glucuronide linkage, the method comprising contacting the substrate with a β-glucuronidase enzyme under conditions such that hydrolysis of the glucuronide linkage occurs, wherein the β-glucuronidase enzyme comprises a mutation consisting of a substitution of an amino acid corresponding to G559 in SEQ ID NO: 18 with an amino acid comprising a side chain comprising a non-aromatic hydroxyl group or histidine or asparagine.

In one embodiment, the method uses a β-glucuronidase enzyme comprising a mutation consisting of a substitution of an amino acid corresponding to G559 in SEQ ID NO: 18 with serine. Preferably, the enzyme having the G559S mutation comprises an amino acid sequence as shown in SEQ ID NO: 19. In another embodiment, the method uses a β-glucuronidase enzyme comprising a mutation consisting of a substitution of an amino acid corresponding to G559 in SEQ ID NO: 18 with threonine. Preferably, the enzyme having the G559T mutation comprises an amino acid sequence as shown in SEQ ID NO: 20. In another embodiment, the method uses a β-glucuronidase enzyme comprising a mutation consisting of a substitution of an amino acid corresponding to G559 in SEQ ID NO: 18 with histidine. In another embodiment, the method uses a β-glucuronidase enzyme comprising a mutation consisting of a substitution of an amino acid corresponding to G559 in SEQ ID NO: 18 with asparagine.

In one embodiment, the substrate used in the method is an opiate glucuronide. Non-limiting examples of opiate glucuronide substrates include morphine-3β-D-glucuronide, morphine-6β-D-glucuronide, codeine-6β-D-glucuronide, hydromorphone-3β-D-glucuronide, oxymorphone-3β-D-glucuronide, and combinations thereof. In another embodiment, the substrate used in the method is a benzodiazepine glucuronide. Non-limiting examples of benzodiazepine glucuronide substrates include oxazepam-glucuronide, lorazepam-glucuronide, temazepam-glucuronide, alprazolam, alpha-hydroxy-alprazolam glucuronide, nordiazepam, 7-amino-clonozepam, and combinations thereof. Additional or alternative glucuronide substrates include the glucuronides of buprenorphine, norbuprenorphine, 11-nor-A9-tetrahydrocannabinol-9-carboxylic acid, testosterone, androsterone, tapentadol, cyclobenzaprine, and amitripyline.

The method of the invention for hydrolyzing a substrate with a glucuronide linkage can be used to test for the presence of drugs in bodily samples, wherein the substrate is present within the sample. Non-limiting examples of bodily samples include samples of blood, urine, tissue or meconium obtained from a subject.

In another aspect, the invention provides "combination" mutated BGUS enzymes having two or more modifications chosen from: (i) a substitution of an amino acid corresponding to G559 in SEQ ID NO: 18 with an amino acid comprising a side chain comprising a non-aromatic hydroxyl group or histidine or asparagine; (ii) an addition of a cysteine residue appended at the carboxy terminus of the enzyme (e.g., addition at the C-terminal end of the enzyme of the sequence: $Xaa_{2-8}$-Cys-$Xaa_{0-2}$, wherein Xaa=any amino acid; and/or (iii) a modification of a region comprising amino acids corresponding to F365 through K370 in SEQ ID NO: 18. In a preferred embodiment, a combination mutant that comprises a substitution at position 559 and that has a cysteine residue appended at or near the C-terminal end has the amino acid sequence shown in SEQ ID NO: 93, wherein position 559 is substituted with Ser (S), Thr (T), His (H) or Asn (N) and wherein the C-terminal end has the following sequence: $Xaa_{2-8}$-Cys-$Xaa_{0-2}$, wherein Xaa=any amino acid.

In the combination mutants having addition of a cysteine residue appended at the carboxy terminus of the enzyme, in a preferred embodiment the tripeptide Gly-Leu-Cys (GLC) is appended to the C-terminus. In another preferred embodiment, the pentapeptide Gly-Leu-Cys-Gly-Arg (GLCGR) (SEQ ID NO: 95) is added. In the combination mutants having a modification of the region comprising amino acids corresponding to F365 through K370 in SEQ ID NO: 18, in one embodiment this modification is a deletion of the region. In another embodiment, the modification is an insertion of the region, for example into a BGUS sequence from a species that does not naturally contain this region.

Packed formulations, as described above, that include a combination mutant of the invention are also provided. Methods of using the combination mutants of the invention (having two or more of the above described modifications) for hydrolysis of glucuronide substrates are also provided in which the mutated β-glucuronidase enzyme is contacted with the glucuronide substrate under conditions such that hydrolysis of the glucuronide linkage occurs.

Other features and aspects of the invention are described in further detail herein.

BRIEF DESCRIPTION OF THE DRAWINGS

FIGS. 1A and 1B show an alignment of the amino acid sequences of the K1S (SEQ ID NO: 19), K1T (SEQ ID NO: 20), K3 (SEQ ID NO: 21), K3Δ1 (SEQ ID NO: 22), K3Δ2 (SEQ ID NO: 23) and K3Δ2S (SEQ ID NO: 24) mutants as compared to the wild type *E. coli* K12 sequence (SEQ ID NO: 18). The F385 through 5396 modification region, G559S or G559T modifications and C-terminal GLC modification in the mutants are highlighted in bold and underlined.

FIG. 2 is an alignment of the amino acid sequences of the *E. coli* K3 mutant (K3) (SEQ ID NO: 25), the abalone (Ab) wild type BGUS (SEQ ID NO: 26), the human (Hu) wild type BGUS (SEQ ID NO: 27), the *Lactobacillus brevis* (L. br.) wild type BGUS (SEQ ID NO: 28) and the *Staphylococcus* sp. RLH1 (S. rlh) wild type BGUS (SEQ ID NO: 29) across amino acid residues 332-416 (*E. coli* numbering), including across the modification region F365 through S376 (*E. coli* numbering). Identical amino acid residues across the five sequences are highlighted in grey. The conserved glutamic acid residue (E) at position 413 (*E. coli* numbering) within the catalytic site is highlighted in bold, indicating the accuracy of the alignment. The modification region F365 through S376 (*E. coli* numbering) is highlighted in bold and underlined.

FIG. 3 is an alignment of the amino acid sequences of the *E. coli* K3 mutant (K3)(SEQ ID NO:30), the abalone (Ab)

wild type BGUS (SEQ ID NO:31), the human (Hu) wild type BGUS (SEQ ID NO:32), the *Lactobacillus brevis* (L. br.) wild type BGUS (SEQ ID NO: 33) and the *Staphylococcus* sp. RLH1 (S. rlh) wild type BGUS (SEQ ID NO: 34) across amino acid residues 452-606 (*E. coli* numbering), including across the G559S modification (*E. coli* numbering) and the C-terminal GLC modification. Identical amino acid residues across the three sequences are highlighted in grey. The conserved tyrosine residue (Y) at position 468 and the conserved glutamic acid residue (E) at position 504 (*E. coli* numbering) within the catalytic site are highlighted in bold, indicating the accuracy of the alignment. The G559S mutation position (*E. coli* numbering) and C-terminal GLC modifications are highlighted in bold and underlined.

Figure 4:
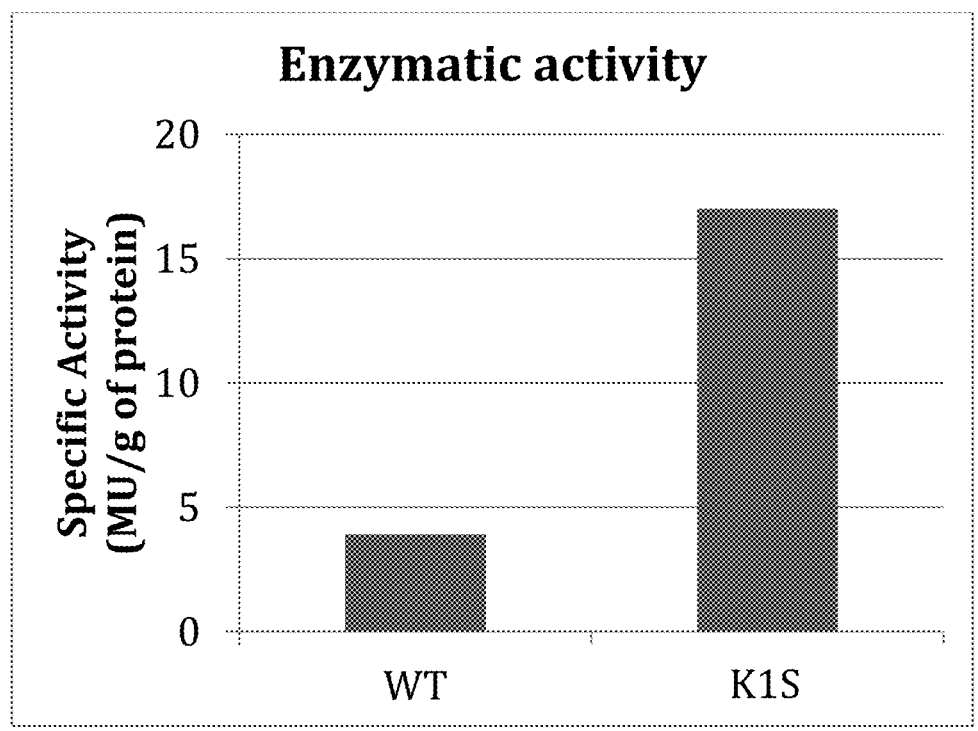

FIG. 4 is a bar graph showing the specific enzyme activity (in MU/g of protein) of the K1S mutant, as compared to the wild type *E. coli* 12 BGUS enzyme, using phenolphthalein-glucuronide as the substrate. Both samples are purified and normalized to protein concentration.

Figure 5:
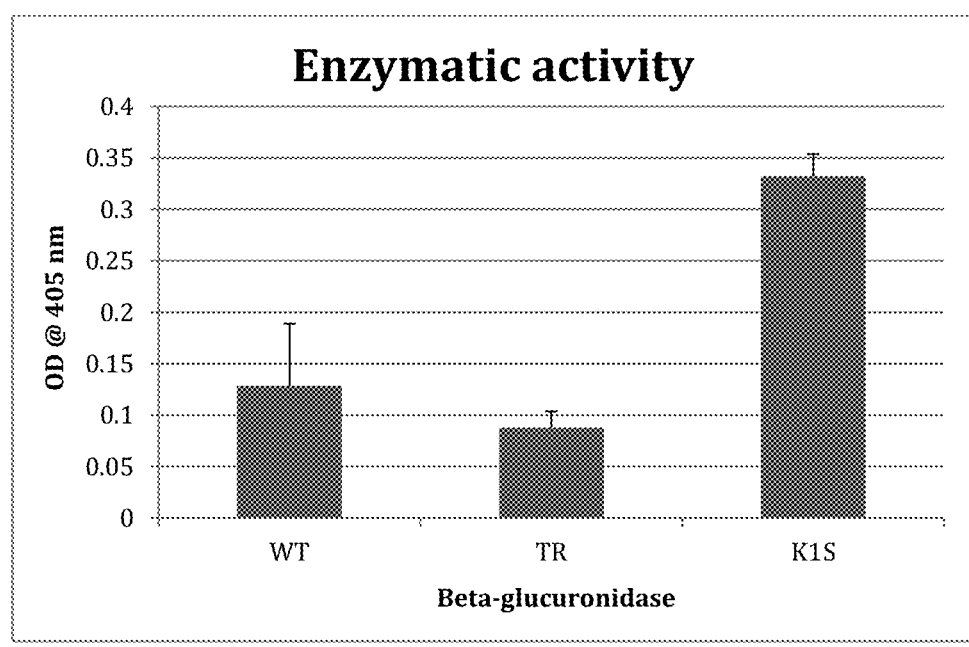

FIG. 5 is a bar graph showing the specific enzyme activity (as measured by OD at 405 nm) of the K1S mutant, as compared to the wild type *E. coli* 12 BGUS enzyme and a thermo-resistant mutant (TR), using 4-nitrophenol glucuronide as the substrate. All three samples are purified and normalized to protein concentration.

Figure 6:
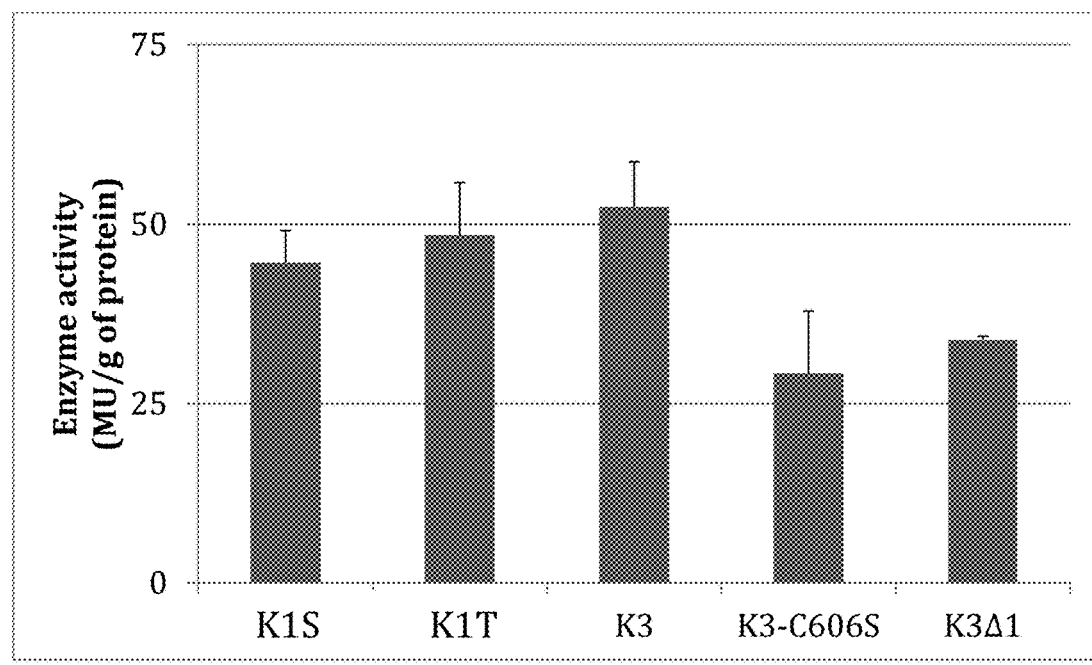

FIG. 6 is a bar graph showing the specific enzyme activity (in MU/g of protein) of the K1T, K3, K3-C606S and K3Δ1 mutants, as compared to the K1S mutant, using phenolphthalein-glucuronide as the substrate. The results were normalized to total protein concentration.

Figure 7A:
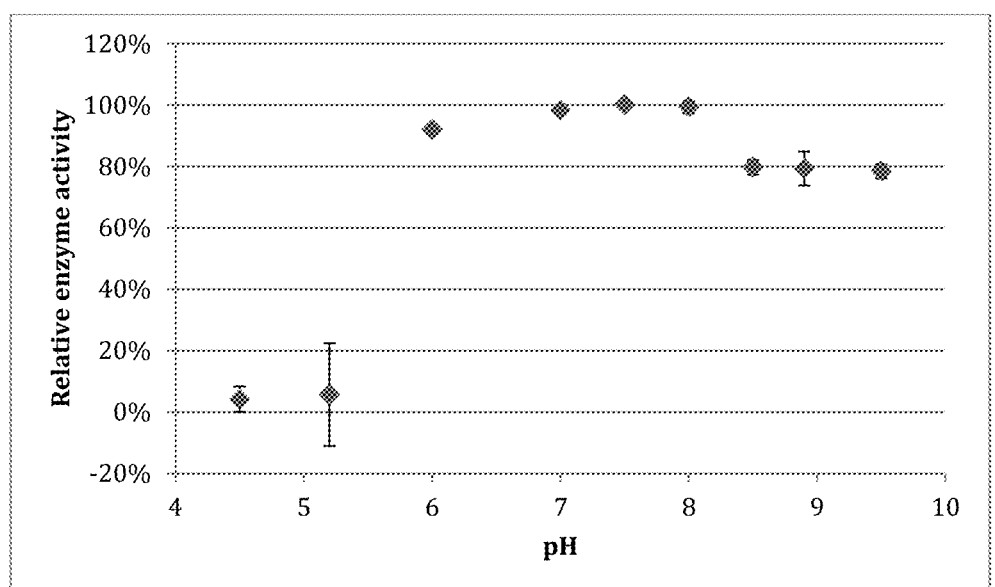

FIG. 7A is a graph showing enzyme activity across various pH levels for the BGUS mutant K3.

Figure 7B:
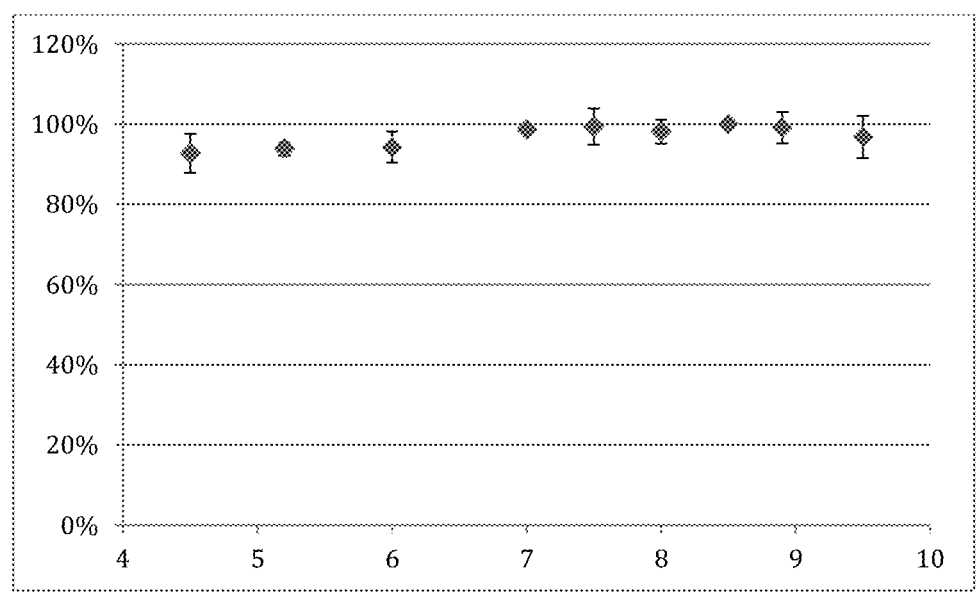

FIG. 7B is a graph showing enzyme activity after overnight storage at different pH levels, following by return of the pH to neutral levels and testing of enzymatic activity for the BGUS mutant K3.

Figure 8:
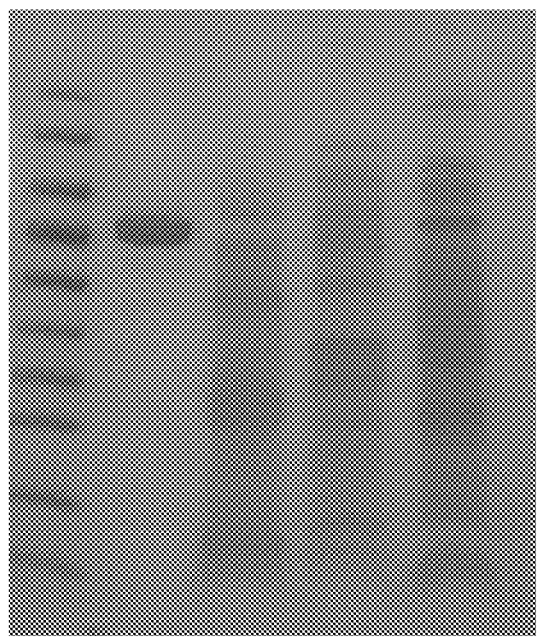

FIG. 8 is a photograph of an SDS-PAGE gel showing the purity of the recombinant K3 enzyme (lane 2) as compared to commercially available abalone (lane 3), snail (lane 4) and *E. coli* (lane 5) extracts. Molecular weight markers are shown in lane 1.

FIG. 9A is an alignment of the wild type abalone BGUS (Wt-Ab) amino acid sequence (SEQ ID NO: 26) with representative loop region insertion mutants Ab1 (SEQ ID NO: 35) and Ab2 (SEQ ID NO: 36) across the loop region F385 through Y395 (*E. coli* numbering).

FIG. 9B is an alignment of the wild type human BGUS (Wt-Ab) amino acid sequence (SEQ ID NO: 27) with representative loop region insertion mutants Hu1 (SEQ ID NO: 37) and Hu2 (SEQ ID NO: 38) across the loop region F365 through Y375 (*E. coli* numbering).

Figure 10:
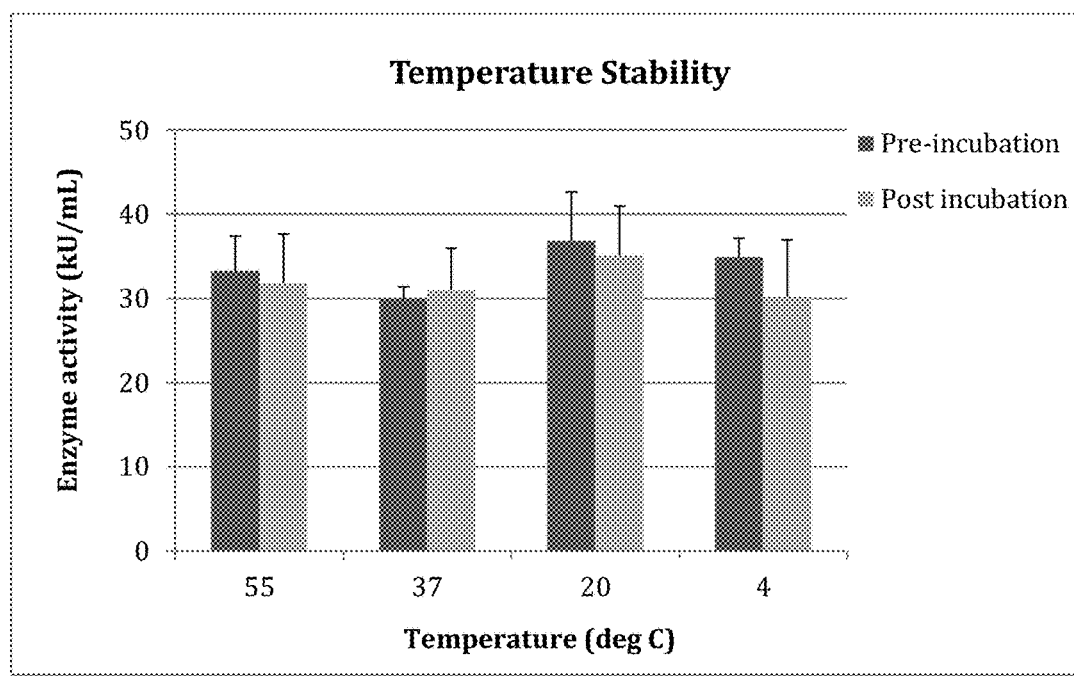

FIG. 10 is a graph showing enzyme activity at four different temperatures for the BGUS mutant K3.

Figure 11:
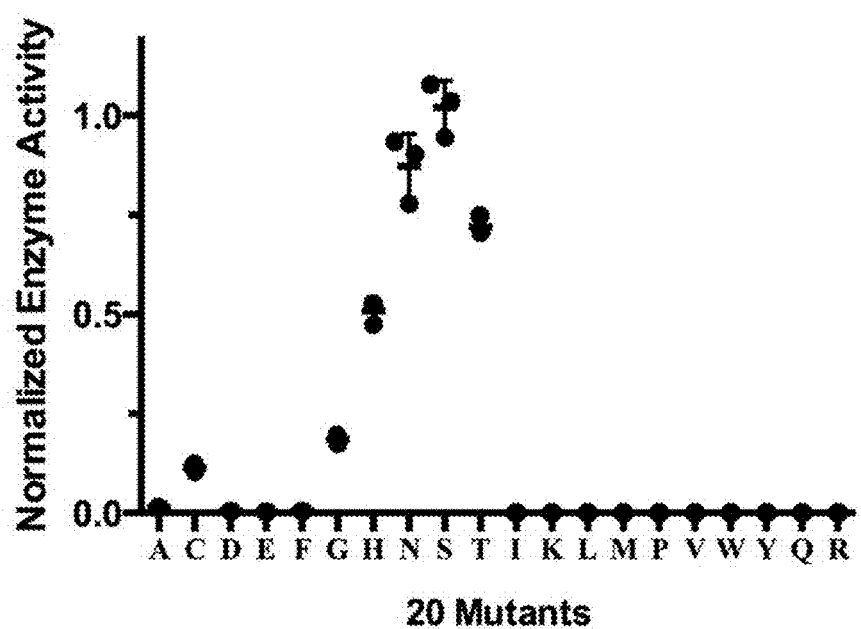

FIG. 11 is a graph showing enzyme activity for BGUS mutants having the indicated amino acid substitution at position 559, demonstrating enhanced enzyme activity for substitutions with histidine (H), asparagine (N), serine (S) and threonine (T).

Figure 12:
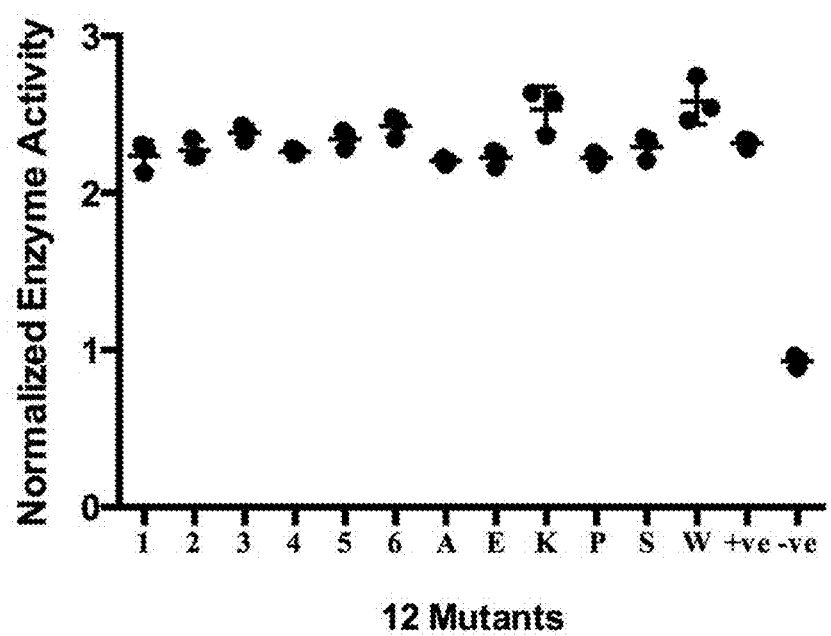

FIG. 12 is a graph showing enzyme activity for BGUS mutants having insertions or substitutions near the carboxy terminus, demonstrating that such mutations do not affect the overall enzyme activity or the thermostability. Purified enzymes were heat treated for one hour prior to measuring their enzymatic activity.

DETAILED DESCRIPTION OF THE INVENTION

The invention pertains to mutated β-glucuronidase enzymes having enhanced enzymatic activity as compared to the wild type enzyme, as well as packaged formulations thereof and methods of using the enzymes for hydrolysis of glucuronide linkages. Various aspects of the invention are described in further detail in the following subsections.

I. Mutated β-Glucuronidase Enzymes

A. Position 559 Substitutions

As used herein, the term β-glucuronidase enzyme", also referred to as β-glucuronidase" or "BGUS", refers to an enzyme that hydrolyzes β-glucuronide linkages. A "wild type" BGUS enzyme refers to the naturally occurring form of the enzyme. A "mutated" BGUS enzyme refers to a modified form of the enzyme in which one or more modifications, such as amino acid substitutions, deletions and/or insertions, have been made such that the amino acid sequence of the mutated BGUS enzyme differs from the wild type amino acid sequence. The nucleotide sequence encoding wild type *E. coli* K12 strain BGUS is shown in SEQ ID NO: 1 (NCBI Reference Sequence: NC_000913.2). The amino acid sequence of wild type *E. coli* K12 strain BGUS is shown in SEQ ID NO: 18 and in FIGS. 1A and 1B. Cloning of the wild type *E. coli* K12 strain BGUS is described in detail in Example 1.

It has now been discovered that a single amino acid substitution of an amino acid corresponding to G559 in SEQ ID NO: 18 (wild type *E. coli* BGUS) with an amino acid comprising a side chain comprising a non-aromatic hydroxyl group, or with histidine or asparagine, creates a mutated BGUS enzyme that has significantly enhanced (e.g., at least 3-fold greater) enzymatic activity as compared to the wild type enzyme. As used herein, a "side chain" of an amino acid refers to the "R" group in the standard generic formula for amino acids: $H_2NCHRCOOH$. A "non-aromatic hydroxyl group" refers to a side chain structure that contains an —OH group, but that lacks a ring structure. In one embodiment, the amino acid comprising a side chain comprising a non-aromatic hydroxyl group is serine (i.e., the mutation in the enzyme consists of a G559S substitution). In another embodiment, the amino acid comprising a side chain comprising a non-aromatic hydroxyl group is threonine (i.e., the mutation in the enzyme consists of a G559T substitution). In yet other embodiments, the amino acid comprising a side chain comprising a non-aromatic hydroxyl group can be a non-naturally occurring amino acid. Non-limiting examples of non-natural amino acids comprising a side chain comprising a non-aromatic hydroxyl group include L-iso-serine (Sigma Aldrich Product #06054), L-allo-threonine (Sigma Aldrich Product #210269), homoserine (Swiss Side Chain ID# HSER), 3-3-dihydoxyalanine (Swiss Side Chain ID# DDZ) and 2-amino-5-hydroxypentanoic acid (Swiss Side Chain ID# AA4).

The preparation of mutant BGUS enzymes having either a single G559S substitution (referred to herein as K1 S) or a single G559T substitution (referred to herein as K1T) is described in detail in Example 2. The full-length amino acid sequence of the K1S mutant is shown in SEQ ID: 19. The full-length amino acid sequence of the K1T mutant is shown in SEQ ID NO: 20. The alignments of the K1S and K1T mutant amino acid sequences as compared to wild-type (SEQ ID NO: 18) are shown in FIGS. 1A and 1B.

The enzymatic activity of the K1S enzyme as compared to wild type is described in detail in Example 4 (first experiment) and shown in FIGS. 4 and 5. This data demonstrates that the single G559S mutation imparts at least a 3-fold, or greater, enhancement in enzymatic activity of the mutant as compared to the wild type enzyme. The enzymatic activity of the K1T enzyme as compared to the K1S is described in detail in Example 4 (third experiment) and shown in FIG. 6. This data demonstrates that the single G559T mutation has a comparable, or even slightly greater enzymatic activity, than the single G559S mutation.

Xiong, A-S. et al. (2007) *Prot. Eng. Design Select.* 20:319-325 has reported the preparation of a mutated BGUS enzyme containing six amino acid substitutions: Q493R, T509A, M532T, N550S, G559S and N566S. This mutant enzyme is reported to have improved thermostability as compared to the wild type enzyme. However, the significantly improved enzymatic activity of the single amino acid substitution, G559S, as reported herein, is not disclosed in or suggested by Xiong et al. A comparison of the enzymatic activity of the K1S mutant (consisting of the G559S substitution) to the thermoresistant six amino acid mutant of Xiong et al. (referred to herein as "TR" and in Xiong et al. as GUS-TR3337) is described in detail in Example 4 (second experiment) and shown in FIG. 5. This data demonstrates that the K1S mutant has significantly enhanced (e.g., 3-fold greater, or more) enzymatic activity as compared to the prior art "TR" mutant enzyme.

Experiments described in Example 7 further demonstrate that substitution of the wild-type G559 position with either histidine (H) or asparagine (N) also leads to enhanced enzymatic activity. The full-length amino acid sequence of a G559H point mutant is shown in SEQ ID: 61. Accordingly, in another aspect, the invention provides a mutated β-glucuronidase enzyme comprising a substitution of an amino acid corresponding to G559 in SEQ ID NO: 18 with histidine. The full-length amino acid sequence of a G559N point mutant is shown in SEQ ID NO: 64. Accordingly, in another aspect, the invention provides a mutated β-glucuronidase enzyme comprising a substitution of an amino acid corresponding to G559 in SEQ ID NO: 18 with asparagine.

The term "substitution of an amino acid corresponding to G559 in SEQ ID NO: 18", as used herein, references the numbering of the wild type *E. coli* strain 12 BGUS enzyme as shown in SEQ ID NO: 18. That is, the wild type sequence shown in SEQ ID NO: 18 has a glycine (G) at position 559 and this amino acid residue, or an amino acid residue corresponding to this residue in another BGUS sequence, is the one that is substituted.

The sequences of BGUS enzymes from numerous species are known in the art. For example, the amino acid sequence of wild type human (*Homo sapiens*) BGUS (isoform 1 precursor) is shown in SEQ ID NO: 39 (NCBI Reference Sequence NP_000172.2). The amino acid sequence of wild type mouse (*Mus musculus*) BGUS (precursor) is shown in SEQ ID NO: 40 (NCBI Reference Sequence NP_034498.1). The amino acid sequence of wild type *Lactobacillus brevis* BGUS is shown in SEQ ID NO: 41 (Genbank Accession No. ACU21612.1). The amino acid sequence of wild type *Staphylococcus* sp. RLH1 BGUS is shown in SEQ ID NO: 42 (Genbank Accession No. AAK29422.1). Furthermore, the sequences of a number of microbial BGUS enzymes are disclosed in U.S. Pat. No. 6,391,547 and EP Patent EP 1175495B, the entire contents of which, including the sequence listing, are incorporated herein by reference.

To identify "an amino acid corresponding to G559 in SEQ ID NO: 18" in a BGUS enzyme sequence other than *E. coli* K12 strain, one of skill in the art can align the BGUS enzyme sequence to SEQ ID NO: 18 using standard computer programs for identifying protein homologies to determine the "best fit" alignment to thereby identify an amino acid residue in the non-*E. coli* K12 sequence that corresponds to G559 in SEQ ID NO: 18. For example, FIG. 3 shows a representative alignment of the *E. coli* K12 (K3 mutant), human, abalone, *Lactobacillus brevis* and *Staphylococcus* sp. RLH1 sequences across the region spanning G559 in SEQ ID NO: 18, with the amino acid position corresponding to G559 in the five sequences indicated. Using such an approach, one of skill in the art can easily make a single amino acid substitution at the position corresponding to G559 in BGUS sequences other than *E. coli* K12.

Accordingly, in one embodiment of the invention, the mutated BGUS enzyme that comprises a mutation consisting of a substitution of an amino acid corresponding to G559 in SEQ ID NO: 18 is from a bacteria, preferably *E. coli*, more preferably *E. coli* strain K12. In another embodiment, the mutated BGUS enzyme is from a mollusk, such as a snail (preferably *Helix pomatia*) or abalone (preferably *Haliotus rufenscens*). In still another embodiment, the mutated BGUS enzyme is from a mammal, preferably a human.

B. Carboxy Terminal Cysteine Residue

It has now been discovered that appending a cysteine residue at or near the carboxy terminal end of the BGUS enzyme enhances the thermostability of the enzyme. Accordingly, in another aspect, the invention provides a mutant BGUS enzyme comprising an addition of a cysteine residue appended at or near the carboxy terminus of the enzyme. As used herein, "the carboxy terminus" (used interchangeably with "C-terminus", "carboxy terminal end" or "C-terminal end") of the BGUS enzyme refers to the end of the protein that terminates in a carboxyl group, according to the standard nomenclature for proteins well established in the art. As used herein, "near the C-terminal end" refers to within a few (i.e., 2-4) amino acids of the C-terminal end.

The cysteine appended to the C-terminus can be contained within a larger peptide. In a preferred embodiment, the cysteine appended to the C-terminus is contained within the following sequence: $Xaa_{2-8}$-Cys-$Xaa_{0-2}$, wherein Xaa=any amino acid (SEQ ID NO: 95). For example, in a preferred embodiment, the cysteine appended to the C-terminal end is part of a tripeptide. A preferred tripeptide for addition onto the C-terminal end has the sequence Gly-Leu-Cys (GLC). Similar tripeptides with conservative substitutions as compared to the GLC tripeptide also can be used. Alternatively, the cysteine appended to the C-terminal end can be part of, for example, a pentapeptide. A preferred pentapeptide for addition to the C-terminal end has the sequence Gly-Leu-Cys-Gly-Arg (GLCGR) (SEQ ID NO: 96). Other exemplary mutant BGUS enzymes having a cysteine appended at or near (within 2 residues of) the C-terminal end have the amino acid sequences shown in SEQ ID NOs: 21, 62, 63, 65, 66-78, 93 and 94.

The preparation of mutant BGUS enzymes having a cysteine appended at the C-terminus, in the form of the tripeptide GLC is described in detail in Example 2. A representative example is a mutant referred to herein as K3, which contains the G559S mutation that is present in the K1 S mutant and also contains the GLC tripeptide at its C-terminus. The full-length amino acid sequence of the K3 mutant is shown in SEQ ID NO: 21. The alignment of the K3 mutant amino acid sequence as compared to wild-type (SEQ ID NO: 18) is shown in FIGS. 1A and 1B.

The enzymatic activity of the K3 mutant as compared to the K1S mutant (which differ only in the addition of GLC at the C-terminus of K3) is described in detail in Example 4 (third experiment) and shown in FIG. 6. This data demonstrates that the K3 enzyme has enzymatic activity that is equal to or even slightly greater than the K1S mutant, which itself has at least 3-fold greater activity than wild type. Furthermore, the thermostability of the K3 mutant as compared to the K1S and K1 T enzymes is described in detail in Examples 5 and 8 and shown in Table 3. This data demonstrates that appending the cysteine at the C-terminal end of the BGUS enzyme enhances its thermostability.

Further experiments described in Example 8 demonstrate that mutations near the cysteine at or near the carboxy terminus do not affect the overall enzyme activity or thermal stability; rather, that it is only the cysteine residue that is critical for enhanced thermal stability of the enzyme. Various mutant enzymes were made having the cysteine appended to the C-terminus contained within the following sequence: $Xaa_{2-8}$-Cys-$Xaa_{0-2}$, wherein Xaa=any amino acid (SEQ ID NO: 95). A representative full length amino acid sequence is shown in SEQ ID NO: 93. The results of the analysis showed that the various mutations and insertions around the appended cysteine residue did not affect the enzymatic activity or thermal stability. Thus, it is possible to insert amino acids upstream or downstream of the cysteine residue or make amino acid substitutions at positions adjacent to the cysteine residue without affecting overall enzyme activity or thermal stability.

As discussed above, the sequences of BGUS enzymes from numerous species are known in the art. Accordingly, a cysteine residue (preferably in the form of a GLC tripeptide or a GLCGR pentapeptide) can be appended to the C-terminus of BGUS sequences from *E. coli* as well as from other species. For example, FIG. 3 shows a representative alignment of the *E. coli* K12 (K3 mutant), human, abalone, *Lactobacillus brevis* and *Staphylococcus* sp. RLH1 sequences with the C-terminal appended cysteine in the K3 mutant indicated. Thus, in one embodiment of the invention, the mutated BGUS enzyme that comprises a cysteine appended to the C-terminus is from a bacteria, preferably *E. coli*, more preferably *E. coli* strain K12. In another embodiment, the mutated BGUS enzyme is from a mollusk, such as a snail (preferably *Helix pomatia*) or abalone (preferably *Haliotus rufenscens*). In still another embodiment, the mutated BGUS enzyme is from a mammal, preferably a human.

C. Modification of Loop Region F365 Through K370

It has now been discovered that a loop region spanning amino acid residues F365 through K370 in SEQ ID NO: 18 (wild type *E. coli* BGUS) is important for effective hydrolysis of codeine glucuronide substrates. The preparation of mutant BGUS enzymes having this region deleted (referred to herein as K3Δ1, K3Δ2 and K3Δ2S) is described in detail in Example 2. The full-length amino acid sequences of the K3Δ1, K3Δ2 and K3Δ2S mutants are shown in SEQ ID NOs: 22, 23 and 24, respectively. The alignments of the K3Δ1, K3Δ2 and K3Δ2S mutant amino acid sequences as compared to wild-type (SEQ ID NO: 18) are shown in FIGS. 1A and 1B.

The enzymatic activity of the K3Δ1 mutant as compared to the K1S and K3 enzymes, as well as the commercially available snail (*Helix pomatia*) BGUS extract, against two different substrates is described in detail in Example 6 and Table 1. This data demonstrate that deletion of the F365 through K370 region does not significantly affect the enzymatic activity against phenolphthalein-glucuronide as a substrate but it does significantly affect the enzymatic activity against codeine-6-glucuronide as a substrate. In particular, deletion of this loop region reduces the activity of the *E. coli* BGUS for the codeine glucuronide substrate nearly as low as that of the snail BGUS, which lacks this loop region in its wild type form. Thus, this data indicates that this loop region is important for imparting to the BGUS enzyme the ability to efficiently hydrolyze codeine glucuronides.

Accordingly, in another aspect, the invention provides a BGUS mutant that comprises a modification of a region comprising amino acids corresponding to F365 through K370 in SEQ ID NO: 18. In one embodiment, the modification is a deletion of this region. For example, a BGUS enzyme that contains this region in its wild type form can be mutated to delete this region to thereby reduce the enzymatic activity of the enzyme against codeine glucuronide substrates. Alternatively, in another embodiment, the modification is an insertion of this region. For example, a BGUS enzyme that lacks this region in its wild type form can be mutated to insert this region to thereby impart or enhance enzymatic activity of the enzyme against codeine glucuronide substrates.

The term "modification of a region comprising amino acids corresponding to F365 through K370 in SEQ ID NO: 18", as used herein, references the numbering of the wild type *E. coli* K12 strain BGUS enzyme as shown in SEQ ID NO: 18. That is, the wild type sequence shown in SEQ ID NO: 18 has the following residues: F365, E366, A367, G368, N369 and K370, and it is these amino acid residues, or amino acid residues corresponding to these residues in another BGUS sequence, that are to be modified.

As described above, the sequences of BGUS enzymes from numerous species are known in the art. To identify "a region comprising amino acids corresponding to F365 through K370 in SEQ ID NO: 18" in a BGUS enzyme sequence other than *E. coli* K12 strain, one of skill in the art can align the BGUS enzyme sequence to SEQ ID NO: 18 using standard computer programs for identifying protein homologies to determine the "best fit" alignment to thereby identify an amino acid residue in the non-*E. coli* K12 sequence that corresponds to F365 through K370 in SEQ ID NO: 18. For example, FIG. 2 shows a representative alignment of the *E. coli* K12 (K3 mutant), human, abalone, *Lactobacillus brevis* and *Stapylococcus* sp. RLH1 sequences across the region spanning F365 through K370 in SEQ ID NO: 18, with the amino acid position corresponding to this region in the five sequences indicated. Using such an approach, one of skill in the art can easily make a modification, such as an insertion into the human or abalone sequence that lacks this loop region, at the region corresponding to F365 through K370 in BGUS sequences other than *E. coli* K12. For example, FIG. 9A shows two representative insertions mutations (referred to as Ab1 and Ab2) of an amino acid sequence comprising the F365 through K370 sequence of SEQ ID NO: 18 into the wild type abalone sequence at the appropriate insertion region. Similarly, FIG. 9B shows two representative insertions mutations (referred to as Hu1 and Hu2) of an amino acid sequence comprising the F365 through K370 sequence of SEQ ID NO: 18 into the wild type human sequence at the appropriate insertion region.

Accordingly, in one embodiment of the invention, the mutated BGUS enzyme that comprises a modification of a region comprising amino acids corresponding to F365 through K370 in SEQ ID NO: 18 is from a bacteria, preferably *E. coli*, more preferably *E. coli* strain K12. In another embodiment, the mutated BGUS enzyme is from a mollusk, such as a snail (preferably *Helix pomatia*) or abalone (preferably *Haliotus rufenscens*). In still another embodiment, the mutated BGUS enzyme is from a mammal, preferably a human.

D. Combination Mutants

In another aspect, the invention pertains to mutant BGUS enzymes that contain two or more of the above described modifications, referred to herein as combination mutants.

Accordingly, in one embodiment, the invention provides a mutated β-glucuronidase enzyme comprising:

(i) a substitution of an amino acid corresponding to G559 in SEQ ID NO: 18 with an amino acid comprising a side chain comprising a non-aromatic hydroxyl group or histidine or asparagine; and (ii) an addition of a cysteine residue appended at or near the carboxy terminus of the enzyme (e.g., wherein the carboxy terminus has the sequence: $Xaa_{2-8}$-Cys-$Xaa_{0-2}$, wherein Xaa=any amino acid).

In another embodiment, the invention provides a mutated β-glucuronidase enzyme comprising:

(i) a substitution of an amino acid corresponding to G559 in SEQ ID NO: 18 with an amino acid comprising a side chain comprising a non-aromatic hydroxyl group or histidine or asparagine; and (ii) a modification of a region comprising amino acids corresponding to F365 through K370 in SEQ ID NO: 18.

In yet another embodiment, the invention provides a mutated β-glucuronidase enzyme comprising:

(i) a substitution of an amino acid corresponding to G559 in SEQ ID NO: 18 with an amino acid comprising a side chain comprising a non-aromatic hydroxyl group or histidine or asparagine;

(ii) an addition of a cysteine residue appended at or near the carboxy terminus of the enzyme (e.g., wherein the carboxy terminus has the sequence: $Xaa_{2-8}$-Cys-$Xaa_{0-2}$, wherein Xaa=any amino acid); and (iii) a modification of a region comprising amino acids corresponding to F365 through K370 in SEQ ID NO: 18.

In still another embodiment, the invention provides a mutated β-glucuronidase enzyme comprising:

(i) an addition of a cysteine residue appended at or near the carboxy terminus of the enzyme (e.g., wherein the carboxy terminus has the sequence: $Xaa_{2-8}$-Cys-$Xaa_{0-2}$, wherein Xaa=any amino acid); and (ii) a modification of a region comprising amino acids corresponding to F365 through K370 in SEQ ID NO: 18.

In these combination mutants having a G559 substitution, in one embodiment, the amino acid corresponding to G559 in SEQ ID NO: 18 is substituted with serine. In another embodiment, the amino acid corresponding to G559 in SEQ ID NO: 18 is substituted with threonine. In yet other embodiments, the amino acid corresponding to G559 in SEQ ID NO: 18 is substituted with a non-natural amino acid as described above in subsection IA.

In the combination mutants having a cysteine residue appended at the carboxy terminus, preferably a tripeptide Glycine-Leucine-Cysteine (GLC) or a pentapeptide Gly-Leu-Cys-Gly-Arg (GLCGR) is appended at the carboxy terminus.

A preferred combination mutant has a G559S substitution and a GLC tripeptide appended at the C-terminus. Preferably, this combination mutant has an amino acid sequence as shown in SEQ ID NO: 21. Another combination mutant has a G559H substitution and a GLC tripeptide appended at the C-terminus, such as the mutant having the amino acid sequence shown in SEQ ID NO: 62. Another combination mutant has a G559H substitution and a GLCGR pentapeptide appended at the C-terminus, such as the mutant having the amino acid sequence shown in SEQ ID NO: 63. Another combination mutant has a G559N substitution and a GLC tripeptide appended at the C-terminus, such as the mutant having the amino acid sequence shown in SEQ ID NO: 65. Another combination mutant has a G559N substitution and a GLCGR pentapeptide appended at the C-terminus, such as the mutant having the amino acid sequence shown in SEQ ID NO: 66. In a preferred embodiment, a combination mutant that comprises a substitution at position 559 and that has a cysteine residue appended at or near the C-terminal end has the amino acid sequence shown in SEQ ID NO: 93, wherein position 559 is substituted with Ser (S), Thr (T), His (H) or Asn (N) and wherein the C-terminal end has the following sequence: $Xaa_{2-8}$-Cys-$Xaa_{0-2}$, wherein Xaa=any amino acid.

In the combination mutants having a modification of the region comprising amino acids corresponding to F365 through K370 in SEQ ID NO: 18, in one embodiment this modification is a deletion of the region. Examples of mutant BGUS enzymes having a deletion of this region include those having the amino acid sequence set forth in SEQ ID NOs: 22, 23 and 24. In another embodiment, the modification is an insertion of the region, for example into a BGUS sequence from a species that does not naturally contain this region.

In one embodiment, a combination mutant as described above is from a bacteria, preferably from *Escherichia coli*, more preferably from *Escherichia coli* K12 strain. In another embodiment, the combination mutant is from a mollusk, such as a snail (preferably *Helix pomatia*) or an abalone (preferably *Haliotus rufenscens*). In yet another embodiment, the combination mutant is from a human.

II. Preparation of Mutant Enzymes

The BGUS enzymes of the invention can be prepared using standard recombinant DNA techniques. A preferred method for mutation is to perform overlap extension PCR using primers that incorporate the desired mutation(s), as described in detail in Example 2. Other methods known in the art for protein mutagenesis, however, are also suitable. Once a nucleic acid fragment encoding the desired mutant BGUS enzyme has been obtained, the fragment can be inserted into a suitable expression vector, transformed into a suitable host cell and the mutant protein expressed recombinantly by culturing of the host cell. Representative non-limiting examples of suitable expression vectors and host cells are described in Example 2, although the skilled artisan will appreciate that any of a variety of expression systems known in the art can be used.

Following recombinant expression of the mutant BGUS enzyme, the protein can be purified using standard protein purification techniques For example, standard affinity chromatography methods, such as immunoaffinity chromatography using an anti-BGUS antibody or metal ion affinity chromatography using nickel, cobalt or copper resin, can be used. As described in detail in Example 6 and FIG. 9, recombinant mutant enzyme of the invention exhibits a significantly higher degree of purity than commercially available extracts from abalone, snail or humans. Thus, the recombinant mutant enzymes of the invention advantageously lack contaminating proteins found in commercially available crude extract preparations, which contaminating proteins could interfere with enzyme activity or efficiency.

III. Packaged Formulations

In another aspect, the invention pertains to packaged formulations that comprise a mutant BGUS enzyme of the invention. These packaged formulations comprise a container comprising a preparation of the mutant BGUS enzyme. Non-limiting examples of suitable containers include bottles, tubes, vials, ampules and the like. Preferably, the container is glass or plastic, although other suitable materials are known in the art. The preparation of the mutant BGUS enzyme can be in liquid or solid form. Thus, in one embodiment, the enzyme preparation is an aqueous solution. In another embodiment, the enzyme preparation is a lyophilized preparation. Lyophilized preparations can be packaged with instructions for reconstituting the enzyme into a liquid solution (e.g., an aqueous solution).

Preferably, the preparation of β-glucuronidase enzyme in the packaged formulation has an enzymatic activity of at least 5,000 Units/ml or 5,000 Units/mg, more preferably at least 10,000 Units/ml or 10,000 Units/mg, even more preferably at least 25,000 Units/ml or 25,000 Units/mg and even more preferably 50,000 Units/ml or 50,000 Units/mg. In one embodiment, the β-glucuronidase enzyme in the preparation is in an aqueous solution with an enzymatic activity of at least 5,000 Units/ml, or at least 10,000 Units/ml or at least 25,000 Units/ml or at least 50,000 Units/ml. In another embodiment, the β-glucuronidase enzyme in the preparation is in lyophilized form with an enzymatic activity of at least 5,000 Units/mg, or at least 10,000 Units/mg or at least 25,000 Units/mg or at least 50,000 Units/mg. In yet another embodiment, the β-glucuronidase enzyme in the preparation is in lyophilized form that when reconstituted as an aqueous solution has an enzymatic activity of at least 5,000 Units/ml, or at least 10,000 Units/ml or at least 25,000 Units/ml or at least 50,000 Units/ml.

The specific activity of the enzyme in the preparation, in Units/ml or Units/mg, can be determined using a standardized glucuronide linkage hydrolysis assay using phenolphthalein-glucuronide as the substrate. The standardization of the specific activity of BGUS has been well established in the art. Thus, 1 Unit of BGUS activity is defined as an amount of enzyme that liberates 1 µg of phenolphthalein from phenolphthalein-glucuronide in 1 hour. An exemplary standardized assay that can be used to determine the specific activity (in Units/ml or Units/mg) of an enzyme preparation (e.g., an aqueous solution or lyophilized preparation) is described in further detail in Example 3. The skilled artisan will appreciate that other protocols for the enzyme assay are also suitable (e.g., such as those described by Sigma Aldrich Chemical Co.). The calculation of Units/ml or Units/mg based on the results of the enzymatic assay also is described in detail in Example 3.

In a preferred embodiment, the preparation containing the mutant BGUS enzyme is substantially free of other non-BGUS proteins. As used herein, "substantially free" refers to less than 5%, preferably less than 3%, even more preferably less than 1% of contamination non-BGUS proteins. In another preferred embodiment, the preparation containing the mutant BGUS enzyme lacks detectable sulfatase activity. In yet another preferred embodiment, the preparation containing the mutant BGUS enzyme is stable at least one month, more preferably at least three months, and even more preferably at least six months at 2-8° C. As used herein, "stable" refers to the mutant BGUS enzyme in the preparation maintaining at least 90%, more preferably at least 95%, even more preferably at least 98% of its enzymatic activity over the indicated time at the indicated temperature.

IV. Methods of Use

The mutant BGUS enzymes of the invention exhibit enhanced ability to hydrolyze glucuronide linkages as compared to the wild type enzyme. Accordingly, the mutant enzymes can be used in methods for hydrolysis of gluruonide substrates. These methods are particularly useful for analyzing bodily samples for the presence of drugs through detection of the glucuronide detoxification products of the drugs. Thus, in another aspect the invention pertains to a method of hydrolyzing a substrate comprising a glucuronide linkage, the method comprising contacting the substrate with a mutant β-glucuronidase enzyme of the invention under conditions such that hydrolysis of the glucuronide linkage occurs. Any of the mutant enzymes of the invention, including those having a single modification and those having more than one modification (i.e., combination mutants) can be used in the method.

In one embodiment, the substrate is an opiate glucuronide. Non-limiting examples of suitable opiate glucuronide substrates include morphine-3β-D-glucuronide, morphine-6β-D-glucuronide, codeine-6β-D-glucuronide, hydromorphone-3β-D-glucuronide, oxymorphone-3β-D-glucuronide, and combinations thereof. In another embodiment, the substrate is a benzodiazepine glucuronide. Non-limiting examples of suitable benzodiazepine glucuronide substrates include the glucuronides of oxazepam, lorazepam, temazepam, and alpha-hydroxy-alprazolam. Other suitable substrates include the glucuronides of buprenorphine, norbuprenorphine, 11-nor-Δ9-tetrahydrocannabinol-9-carboxylic acid, testosterone, androsterone, tapentadol, cyclobenzaprine, amitripyline and combinations thereof.

The methods of the invention can be used on a variety of different bodily samples. Non-limiting examples of suitable bodily samples include blood, urine, tissue or meconium obtained from a subject. Such samples can be obtained, stored and prepared for analysis using standard methods well established in the art.

Following hydrolysis by the enzyme, the cleavage products in the sample can be analyzed by standard methodologies, such as high performance liquid chromatography (HPLC), gas chromatography (GC) and/or mass spectrometry (MS). Such approaches for analysis of bodily samples for the presence of drugs are well established in the art. For example, a completely automated workflow for the hydrolysis and analysis of urine samples by LC-MS/MS, which can be applied using the mutant enzymes of the invention for hydrolysis, is described in Cabrices, O. G. et al., GERSTEL AppNote AN/2014/4-7.

In addition to its use in drug testing, a mutated BGUS enzyme of the invention can be used in essentially any other methodology for which the wild type BGUS enzyme can be used. For example, U.S. Pat. No. 5,599,670 describes a gene fusion system in which DNA encoding a BGUS enzyme is fused to DNA encoding a gene of interest to create a reporter gene system that can be used for a wide variety of genetic engineering purposes. Accordingly, the mutated BGUS enzymes of the invention can be used in this gene fusion system to enhance the enzymatic activity of the BGUS portion of the fusion protein.

The present invention is further illustrated by the following examples, which should not be construed as further limiting. The contents of Sequence Listing, figures and all references, patents and published patent applications cited throughout this application are expressly incorporated herein by reference.

EXAMPLES

Example 1: Cloning of *E. coli* β-Glucuronidase (BGUS) Gene

In this example, the wild type *E. coli* BGUS sequence was cloned by polymerase chain reaction (PCR) based on the published *E. coli* K12 BGUS sequence derived from the *E. coli* genome (NCBI Reference Sequence NC_000913.2), shown in SEQ ID NO: 1. The forward primer used for PCR had the following sequence: GAGAGACATATGT-TACGTCCTGTAGAAACCCC (SEQ ID NO: 2). The reverse primer for PCR had the following sequence: GAGA-GAAAGCTTTCATTGTTTGCCTCCCTGCT (SEQ ID NO: 3). The forward primer contains an NdeI restriction site and the reverse primer contains a HindIII restriction site.

To isolate a sample of *E. coli* DH5α strain genomic DNA, 5 ml of LB culture were grown overnight and 1 ml of cells was pelleted in a 1.5 ml tube. The cells were resuspended in 50 µl of water and were heated at 95° C. for 5 minutes to lyse the cells. The debris was pelleted and 10 µl of supernatant was used as a template in the PCR reaction.

For the PCR reaction, the primers were diluted to 10 µM and 5 µl of each primer was used in a 50 µl PCR reaction (final primer concentration was 1 µM). The 50 µl reaction mixture contained the following: 10× ThermoPol Buffer (5 µl), 10 mM dNTP (1 µl), BGUS forward primer (5 µl), BGUS reverse primer (5 µl), *E. coli* DNA (10 µl), NEB Taq enzyme (1 µl), water (23 µl). The PCR program used for DNA amplification was as follows: 95° C./5 minutes, 40 cycles of 95° C./30 seconds, 50° C./30 seconds, 72° C./2.5 minutes, followed by 72° C./5 minutes, 4° C./00.

After amplification, the PCR product was digested with NdeI and HindIII for cloning into a bacterial expression vector. The reaction mixture contained the following: PCR product (16 µl), NdeI (20 U/µl) (1 µl), HindIII (20 U/µl) (1 µl), 10×NEB Reaction Buffer 2 (2 µl). The restriction enzyme digestion reaction was carried out at 37° C. for 60 minutes.

The bacterial vector was prepared by digestion with NdeI and HindIII in a reaction mixture that contained the following: Vector (0.1 µg/µl) (10 µl), NdeI (20 U/µl) (1 µl), HindIII (20 U/µl) (1 µl), 10×NEB Reaction Buffer 2 (2 µl), water (6 µl). The restriction enzyme digestion reaction was carried out at 37° C. for 60 minutes. Then 2 µl of 10× Shrimp Alkaline Phosphatase (SAP) buffer and 1 µl of SAP enzyme was added to the restriction enzyme digestion for the vector and incubated at 37° C. for 30 minutes. All fragments were isolated on a 1% low melting point (LMP) agarose gel in 1× Tris-Acetate-EDTA running buffer.

The agarose fragments containing the vector and the insert DNA were melted at 68° C. for 10 minutes. A ligation reaction was prepared that contained the following: Vector/NdeI/HindIII/SAP (3 µl), BGUS ORF/NdeI/HindIII (7 µl), 10×NEB T4 DNA Ligase Buffer (5 µl), T4 DNA Ligase (400 U/µl)(1 µl), water (34 µl). The ligation reaction mixture was incubated at room temperature overnight.

Following the overnight ligation reaction, the T4 DNA ligase was heat inactivated by heating the reaction at 68° C. for 10 minutes. For transformation into competent cells, an aliquot of competent DH5a cells was thawed on ice and 150 µl of the competent cells as added to the ligation reaction and mixed by gentle pipetting. The cells were then incubated on ice for 30 minutes, followed by heat shock at 42° C. for 3 minutes. The cells were then placed back on ice for 2 minutes and then transferred to 1 ml of LB medium in a 14 ml culture tube. The cell culture was incubated at 37° C. for 60 minutes at 250 rpm. Aliquots of the cells were added to LB-Kanamycin plates and grown overnight at 37° C. Colonies were picked for plasmid extraction and analysis by DNA sequencing using standard techniques to identify a plasmid that contained the cloned *E. coli* wild type BGUS gene.

Example 2: Mutagenesis of *E. coli* β-Glucuronidase (BGUS) Gene

Overlap extension PCR was used to create mutations in the *E. coli* K12 BGUS ORF using the plasmid encoding the wild type enzyme as the template. Four primers were used to create the K1S mutant (having a G559S single amino acid substitution), as follows:

| | |
|---|---|
| BGUS Forward: | CTGCTGTCGGCTTTAACCTC (SEQ ID NO: 4) |
| G559S Forward: | GACCTCGCAAAGCATATTGCG (SEQ ID NO: 5) |
| G559S Reverse: | CGCAATATGCTTTGCGAGGTC (SEQ ID NO: 6) |
| Vector Reverse: | CTAGTTATTGCTCAGCGGT (SEQ ID NO: 7) |

Two parallel PCR reactions were set up that were designed to produce the 5' and 3' parts of the desired mutated DNA fragments. Reaction 1 contained the following: 10× Pfu Buffer (5 µl), 10 mM dNTP (1 µl), 10 µM BGUS forward primer (1 µl), 10 µM G559 reverse primer (1 µl), wild-type plasmid template (0.1 µg/µl) (1 µl), Pfu enzyme (1 µl), water (40 µl). Reaction 2 contained the following: 10× Pfu Buffer (5 µl), 10 mM dNTP (1 µl), 10 µM G559S forward primer (1 µl), 10 µM Vector reverse primer (1 µl), wild type plasmid template (0.1 µg/µl) (1 µl), Pfu enzyme (1 µl), water (40 µl). The PCR program used for DNA amplification was as follows: 95° C./5 minutes, 40 cycles of 95° C./30 seconds, 50° C./30 seconds, 72° C./60 seconds, followed by 72° C./5 minutes, 4° C./∞.

The DNA fragments were purified using an Omega Cycle Pure Kit and the two purified fragments were mixed together to form the final (mutated) product in a PCR reaction that contained the following: 10× Pfu Buffer (5 µl), 10 mM dNTP (1 µl), 10 µM BGUS forward primer (1 µl), 10 µM Vector reverse primer (1 µl), Fragment 1 (10 µl), Fragment 2 (10 µl), Pfu enzyme (1 µl), water (31 µl). The PCR program used for DNA amplification was as follows: 95° C./5 minutes, 40 cycles of 95° C./30 seconds, 50° C./30 seconds, 72° C./90 seconds, followed by 72° C./5 minutes, 4° C./00.

The final DNA fragment was purified using an Omega Cycle Pure Kit. The fragment was digested with BstB1 and HindIII restriction enzymes in pUC19 bacterial vector. The recipient bacterial plasmid was digested with BstB1 and HindIII, followed by treatment with SAP. All fragments were isolated on an LMP gel and an in gel ligation reaction was performed using standard techniques. Plasmid DNA was isolated for sequencing to identify the mutant clone. For large-scale expression of the mutant enzyme, the coding sequence of the mutant enzyme was cloned into the bacterial expression vector pSF-TAC (commercially available from Sigma Aldrich) or pD441-NH (commercially available from DNA2.0), both of which vectors contain an IPTG-inducible TAC or T5 promoter and a kanamycin resistance gene.

The protocol used to produce additional mutants was very similar to that described above for preparing the K1S mutant, except that each mutant had a specific pair of mutagenic primers for use in the overlap extension PCR. To prepare the K1T, K3, K3Δ1, K3Δ2 and K3Δ2S mutants, the following primers were used in overlap extension PCR reactions as described above:

| Mutant | Forward Primer | Reverse Primer |
|---|---|---|
| K1T | GCGACCTCGCAAACCATATTGCGC (SEQ ID NO: 8) | GCGCAATATGGTTTGCGAGGTCGC (SEQ ID NO: 9) |

-continued

| Mutant | Forward Primer | Reverse Primer |
|---|---|---|
| K3 | CAAACAAGGCCTATGCTAGAA AGGAGAAGCTTG (SEQ ID NO: 10) | CAAGCTTCTCCTTTCTAGCATA GGCCTTGTTTG (SEQ ID NO: 11) |
| K3Δ1 | TCTTTAGGCATTGGTCCGAAA GAACTGTAC (SEQ ID NO: 12) | GTACAGTTCTTTCGGACCAATG CCTAAAGA (SEQ ID NO: 13) |
| K3Δ2 | TCTTTAGGCATTGGTGAAGAG GCAGTCAAC (SEQ ID NO: 14) | GTTGACTGCCTCTTCACCAATG CCTAAAGA (SEQ ID NO: 15) |
| K3Δ2S | CCGCAGTTCTTCAACGGGGAA ACTCAG (SEQ ID NO: 16) | GAAGAACTGCGGACCAATGCCT AAAGAG (SEQ ID NO: 17) |

For the K1T mutant, the wild type BGUS sequence was used as the PCR template, similar to as described above for the K1S mutant. The resultant K1T mutant contains a G559T single amino acid substitution.

For the K3 mutant, the K1S mutant sequence was used as the PCR template. The K3 mutant contains a G559S single amino acid substitution and also contains a "GLC" tripeptide added onto the C-terminal end of the protein.

For the K3Δ1 mutant, the K3 mutant sequence was used as the PCR template. The K3Δ1 mutant contains a G559S single amino acid substitution, a "GLC" tripeptide added onto the C-terminal end of the protein and a deletion of amino acid residues F365 through K370.

For the K3Δ2 mutant, the K3 mutant sequence was used as the PCR template. The K3Δ2 mutant contains a G559S single amino acid substitution, a "GLC" tripeptide added onto the C-terminal end of the protein and a deletion of amino acid residues F365 through S376.

For the K3Δ2S mutants, the K3 mutant sequence was used as the PCR template. The K3Δ2S mutant contains a G559S single amino acid substitution, a "GLC" tripeptide added onto the C-terminal end of the protein, a deletion of amino acid residues F365 through S376 and the following additional substitutions: E377P, E378Q, A379F and V380F.

Following PCR amplification and plasmid ligation as described above, the plasmid DNA was isolated for sequencing to identify the mutant clones. An alignment of the amino acid sequences of the K1S, K1T, K3, K3Δ1, K3Δ2 and K3Δ2S mutants compared to the wild type sequence is shown in FIGS. 1A and 1B.

An alignment of the amino acid sequences of the *E. coli* K3 mutant, the abalone wild type BGUS, the human wild type BGUS, the *Lactobacillus brevis* wild type BGUS and the *Staphylococcus* sp. RLH1 wild type BGUS across amino acid residues 332-416 (*E. coli* numbering), including across the modification region F365 through S376 (*E. coli* numbering), is shown in FIG. 2. Identical amino acid residues across the five sequences are highlighted in grey. The conserved glutamic acid residue (E) at position 413 (*E. coli* numbering) within the catalytic site is highlighted in bold, indicating the accuracy of the alignment. This conserved residue within the catalytic domain is described further in *J. Biol. Chem.* (1996) vol. 273(51), pp. 34507-34602 and *Proc. Natl. Acad. Sci. USA* (1995) vol. 92(15), pp. 7090-7094. The modification region F365 through S376 (*E. coli* numbering) is highlighted in bold and underlined.

An alignment of the amino acid sequences of the *E. coli* K3 mutant, the abalone wild type BGUS, the human wild type BGUS, the *Lactobacillus brevis* wild type BGUS and the *Staphylococcus* sp. RLH1 wild type BGUS across amino acid residues 452-606 (*E. coli* numbering), including across the G559S modification (*E. coli* numbering) and the C-terminal GLC modification, is shown in FIG. 3. Identical amino acid residues across the five sequences are highlighted in grey. The conserved tyrosine residue (Y) at position 468 and glutamic acid residue (E) at position 504 (*E. coli* numbering) within the catalytic site is highlighted in bold, indicating the accuracy of the alignment. These conserved residues within the catalytic domain are described further in *J. Biol. Chem.* (1996) vol. 273(51), pp. 34507-34602 and *Proc. Natl. Acad. Sci. USA* (1995) vol. 92(15), pp. 7090-7094. The G559S (*E. coli* numbering) and C-terminal GLC modifications are highlighted in bold and underlined.

Example 3: β-Glucuronidase Enzymatic Activity Assay

In this example, a standard enzyme activity assay for BGUS is described. The standard reporting format for this assay is in Units/ml for liquid formulations or in Units/mg for lyophilized formulations.

An activity assay buffer, 20 mM potassium phosphate buffer, pH 6.8, was prepared. The substrate solution used was 1 mM phenolphthaleine-glucuronide (PT-gluc) in water, prepared fresh. 400 µl of activity buffer was pipetted into a clean 1.5 ml microfuge tube. 4 µl of enzyme solution was added to the buffer to achieve a 1:100 dilution of the enzyme. Then, 30 µl of the diluted enzyme solution was pipetted in each well of a 96-well plate, with each enzyme solution performed in triplicate. 30 µl of diluted control enzyme solution was pipetted into control wells in triplicate. 30 µl of the PT-gluc substrate solution was pipetted into the wells with the enzyme solution. The plates were incubated for 30 minutes at 25° C. 180 µl of glycine was added to stop the reaction and develop color in each well. The absorbance at 540 nm was measured by standard methods.

1 Unit of BGUS activity is defined as an amount of enzyme that liberates 1 µg of phenolphthalein from phenolphthalein-glucuronide in 1 hour. Thus, to determine Units/ml of enzyme, first a standard curve was prepared by plotting background-subtracted absorbance at 540 nm for the phenolphthalein (PT) standards. Assuming a linear plot for the standard curve, the formula for determining the concentration of PT liberated by the enzyme is as follows:

[conc. PT in µg]=[(corrected absorbance at 540 nm)−(y intercept value)]/slope

The specific activity of the enzyme was determined by correcting for time and dilution factors, divided by the volume of enzyme used. Thus, to calculate the specific activity in Units/ml using the assay protocol above, the following formula was used:

Units/mL=(µg of PT released)×2×100/0.03

Example 4: Enzymatic Activity of β-Glucuronidase Mutants

In this example, the enzymatic assay of the BGUS mutants was examined in a series of experiments comparing their activity to wild type *E. coli* BGUS, as well as to another mutant previously described in the art or to a commercially available *Helix pomatia* (snail) BGUS enzyme extract. Different glucuronide substrates were examined, as described further below, using the enzymatic activity assay described in Example 3

In a first experiment, the specific activity of the K1S mutant, as compared to the wild type *E. coli* enzyme, was tested using the enzymatic activity assay described in Example 3 that uses phenolphthalein-glucuronide as the substrate. The results are shown in FIG. 4. The results demonstrate that the K1S mutant exhibits significantly increased specific enzyme activity (over 3-fold greater activity) compared to the wild type enzyme.

In a second experiment, the specific activity of the K1S mutant was compared to the wild type *E. coli* BGUS enzyme and to a thermo-resistant mutant that was reported in Xiong, A-S. et al. (2007) *Prot. Eng. Design Select.* 20:319-325. The thermoresistant mutant described in Xiong et al. (referred to in FIG. 5 as "TR" and referred to in Xiong et al. as GUS-TR3337) contains the G559S substitution but also contains five other single residue substitutions: Q439R, T509A, M532T, N550S and N566S. The enzyme reaction used approximately 500 ng of purified enzyme incubated with 750 µM concentration of 4-nitrophenol glucuronide as the substrate, followed by measurement of absorbance at 405 nm. The results are shown in FIG. 5. The results demonstrate that the K1S mutant exhibits significantly increased specific enzyme activity (over 3-fold greater activity) compared to both the wild type enzyme and the previously-reported TR (GUS-TR3337) mutant.

In a third experiment, the specific activity of the K1T, K3, K3-C606S and K3Δ1 mutants, as compared to the K1S mutant, was tested. The results are shown in FIG. 6. The results demonstrate that the K1T and K3 mutants exhibit specific enzyme activity that is equal to or greater than that of the K1S mutant, whereas the K3-C606S and K3Δ1 mutants exhibit specific activity that is lower than that of the K1S mutant, although still higher than the wild type enzyme.

The K3-C606S mutant differs from the K3 mutant in that the C-terminal cysteine in K3 has been substituted with a serine. Thus, the results with K3-C606S as compared to K3 demonstrate the contribution of the C-terminal cysteine to the enzymatic activity. The K3Δ1 mutant differs from the K3 mutant in that residues F365 through K370 have been deleted. Thus, the results with K3Δ1 as compared to K3 demonstrate the contribution of the F365-K370 loop region to the enzymatic activity.

In a fourth experiment, the role of the F365-K370 loop region was further examined by comparing hydrolysis of two different substrates, phenolphthalein-glucuronide and codeine-6-glucuronide, by the K1S, K3 and K3Δ1 mutants as compared to commercially available wild type *Helix pomatia* BGUS enzyme. The specific activities of the enzymes (in kU/ml) was determined using the phenolphthalein-glucuronide hydrolysis assay described above. For the codeine-6-glucuronide hydrolysis, the reaction mixtures contained 200 µl of drug-free urine sample, 40 µl enzyme, 50 µl rapid hydrolysis buffer and 10 µl codeine-$D_6$ (10 ppm) in acetonitrile. The reactions were incubated at 55° C. for 60 minutes. The results are shown below in Table 1:

TABLE 1

| | Specific enzyme activity (kU/ml) | codeine (ppb) |
|---|---|---|
| No enzyme | NA | NF |
| K1S | 73 | 935.0 |
| K3 | 83 | 881.8 |
| K3Δ1 | 78 | 345.1 |
| *Helix pomatia* without incubation | 114 | NF |
| *Helix pomatia* with 30 min. incubation | 114 | 129.1 |

NF = not found,
NA = not applicable,
ppb = parts per billion

The results showed that for the phenolphthalein-glucuronide substrate, the BGUS mutants and the commercially available snail extract had similar specific activities, with the snail extract exhibiting slightly higher activity than the *E. coli* BGUS mutants.

The hydrolysis of codeine-6-glucuronide, however, differed among the enzymes tested. Both the K1S and K3 mutants exhibited efficient hydrolysis of codeine-6-glucuronide, recovering 935.0 and 881.8 ppb codeine, respectively, from 1000 ppb of codeine-6-glucuronide substrate. In contrast, the K3Δ1 mutant, which differs from K3 in that K3Δ1 has a deletion of the loop region F365-K370, only recovered 345.1 ppb codeine from 1000 ppb codeine-6-glucuronide substrate. This result demonstrates that deletion of this loop region depresses the hydrolysis of the codeine glucuronides. In comparison, the *Helix pomatia* (snail) enzyme had a very low hydrolysis of codeine-6-glucuronide (129.1 ppb recovered from 1000 ppb substrate), despite having a higher specific activity than the *E. coli* mutants for the phenolphthalein-glucuronide substrate. This result is consistent with the F365-K370 loop region being important for hydrolysis of codeine glucuronides, since the *Helix pomatia* amino acid sequence lacks a region corresponding to the F365-K370 loop region of *E. coli*. Thus, based on these studies, one can mimic the level of snail BGUS activity for codeine glucuronides by replacing of this loop region in BGUS enzymes that contain the loop (e.g., *E. coli*). Moreover, one can improve the level of BGUS activity for codeine glucuronides by inserting this loop region into BGUS enzymes that lack the loop (e.g., snail, abalone or human versions of BGUS).

Example 5: Thermostability of β-Glucuronidase Mutants

To examine the heat stability of the mutants, the enzymes were either unheated, or heated for 30 or 60 minutes at 65° C., and the percent of original enzyme activity left after heating was measured. In a first series of experiments, the thermostability of the K1 S, K3, K3-C606S and K1T enzymes were compared. The results demonstrate that the K3 mutant, which has a C-terminal cysteine residue modification, exhibits a higher thermostability that the K1S and K1T mutants, which lacks this C-terminal cysteine. The mutation of the cysteine residue at the carboxy terminus of the K3 mutant to serine, to form the K3-C606S variant, eliminates this heat stability, thereby demonstrating the contribution of the C-terminal cysteine to the thermostability. Wild type enzyme had similar heat stability as K1 S.

The thermostability of the K3 mutant was further examined at four different temperatures using a 2 hour incubation period. Enzyme mixtures, containing buffer and analytes, were incubated at either 4° C., 20° C., 37° C. or 55° C. Enzyme activity was measured both pre- and post-incubation. The results are shown in FIG. 10, expressed as kU/mL, comparing the pre- and post-incubation enzymatic activity at the four different temperatures. The results demonstrate the stability of the purified, recombinant K3 mutant enzyme at the four different temperatures, showing no loss of enzyme activity over time at any of the temperatures tested.

A further analysis of the effect of C-terminal mutations on the thermostability of the BGUS enzyme is described in Example 8 below.

Example 6: Further Characterization of β-Glucuronidase K3 Mutant

In this example, the effects of pH on the activity of the BGUS K3 mutant, as well as the purity of the protein, were further characterized.

Effect of pH

The relative enzyme activity was measured at various pH levels to examine the effect of pH on the enzyme activity. The results are shown in FIGS. 7A and 7B for the K3 mutant. For the results shown in FIG. 7A, the enzyme activity dropped significantly when the buffer solution pH was below 6. The optimal pH range for enzyme activity was within pH 7-8. For the results shown in FIG. 7B, the enzyme was stored overnight at different pH levels and then enzyme activity was tested by bringing the pH back to neutral levels. Thus comparing the results in FIGS. 7A and 7B, the results showed that although the pH level affects the enzymatic activity, it does not affect the stability of the enzyme in the short term during storage when the pH is returned to neutral levels for testing enzyme activity.

Purity

The recombinant K3 enzyme was purified by standard affinity purification and the resultant purified protein was examined by SDS-PAGE as compared to commercially available preparations of BGUS protein from different species. The results are shown in FIG. 8, in which lane 1 shows the molecular weight markers, lane 2 shows the K3 mutant, lane 3 shows a commercially available abalone BGUS preparation, lane 4 shows a commercially available snail BGUS preparation and lane 5 shows a commercially available E. coli BGUS preparation. The results show that each of the commercially available BGUS preparations contained extraneous proteins that may interfere with downstream analytical processing of test samples, whereas the purified recombinant K3 preparation did not contain these extraneous proteins.

Example 7: Further Analysis of β-Glucuronidase Position 559 Mutants

In this example, the wild-type glycine at position 559 of BGUS was substituted with each of the 19 other natural amino acids to determine the effect of the substitutions on enzyme activity. Each 559 position mutant also included the "GLC" addition at the C-terminal end (as in the K3 enzyme) to enhance thermostability.

In addition to the G559S and G559T mutations described above, the 17 other point mutations at position 559 were prepared using the following forward primers in overlap extension PCR reactions as described above. All reactions used the following as the reverse primer: GCAAAATCG-GCGAAATTC (SEQ ID NO: 43).

| Mutant | Forward Primer |
|---|---|
| G559A | GACCTCGCAAGCAATATTGCGCGTTG (SEQ ID NO: 44) |
| G559C | GACCTCGCAATGTATATTGCGCGTTG (SEQ ID NO: 45) |
| G559D | GACCTCGCAAGATATATTGCGCGTTG (SEQ ID NO: 46) |
| G559E | GACCTCGCAAGAAATATTGCGCGTTG (SEQ ID NO: 47) |
| G559F | GACCTCGCAATTCATATTGCGCGTTG (SEQ ID NO: 48) |
| G559H | GACCTCGCAACATATATTGCGCGTTG (SEQ ID NO: 49) |
| G559I | GACCTCGCAAATCATATTGCGCGTTG (SEQ ID NO: 50) |
| G559K | GACCTCGCAAAAAATATTGCGCGTTG (SEQ ID NO: 51) |
| G559L | GACCTCGCAACTGATATTGCGCGTTG (SEQ ID NO: 52) |
| G559M | GACCTCGCAAATGATATTGCGCGTTG (SEQ ID NO: 53) |
| G559N | GACCTCGCAAAACATATTGCGCGTTG (SEQ ID NO: 54) |
| G559P | GACCTCGCAACCGATATTGCGCGTTG (SEQ ID NO: 55) |
| G559Q | GACCTCGCAACAGATATTGCGCGTTG (SEQ ID NO: 56) |
| G559R | GACCTCGCAACGTATATTGCGCGTTG (SEQ ID NO: 57) |
| G559V | GACCTCGCAAGTGATATTGCGCGTTG (SEQ ID NO: 58) |
| G559W | GACCTCGCAATGGATATTGCGCGTTG (SEQ ID NO: 59) |
| G559Y | GACCTCGCAATACATATTGCGCGTTG (SEQ ID NO: 60) |

Enzyme activity was tested as described in the previous examples. The results for the 19 different position 559 point mutations, as compared to the wild type glycine (G), are shown in FIG. 11. The results demonstrate that substitution at position 559 with either serine (S), threonine (T), histidine (H) or asparagine (N) (as compared to the wild-type glycine (G)) resulted in enhanced enzyme activity.

Example 8: Further Analysis of β-Glucuronidase C-Terminal Mutants

In this example, the C-terminal end of the BGUS enzyme was mutated with various substitutions and/or insertions to determine the effect on overall enzyme activity and thermostability. The mutations made at the C-terminal end are shown below in Table 2. Each mutant also included the G559S mutation. The entire amino acid sequence of each mutant is shown in the Sequence Listing at the indicated SEQ ID NOs. Additionally, the forward and reverse primers used to prepare the mutants in overlap extension PCR reactions are shown in the Sequence Listing at the indicated SEQ ID NOs.

TABLE 2

| Mutation Type | Mutant Portion of BGUS | Mutant SEQ ID NO: | Forward Primer SEQ | Reverse Primer SEQ |
|---|---|---|---|---|
| Serine (S) | SSCXX | 67 | 79 | 85 |
| Glutamic Acid (E) | EECXX | 68 | 80 | 85 |
| Lysine (K) | KKCXX | 69 | 81 | 85 |
| Alanine (A) | AACXX | 70 | 82 | 85 |
| Tryptophan (W) | WWCXX | 71 | 83 | 85 |
| Proline (P) | PPCXX | 72 | 84 | 85 |
| 1 | GLGCXX | 73 | 86 | 92 |
| 2 | GLGGCXX | 74 | 87 | 92 |
| 3 | GLGGGCXX | 75 | 88 | 92 |
| 4 | GLGGGGCXX | 76 | 89 | 92 |
| 5 | GLGGGGGCXX | 77 | 90 | 92 |
| 6 | GLGGGGGGCXX | 78 | 91 | 92 |

Enzyme activity was tested as described in the previous examples. Purified enzymes were heat treated for one hour prior to measuring their enzymatic activity. The results are shown in FIG. 12. All substitution and insertion mutations tested showed similar enzymatic activity as that of the positive control, thereby demonstrating that the mutations near the carboxy terminus do not affect the overall enzyme activity. Furthermore, the heat pre-treatment did not affect the enzymatic activity, thereby demonstrating that the substitutions and insertions around the cysteine residue did not affect the thermostability. Thus, these results indicate that the length and type of amino acid variation prior to the cysteine residue near the carboxy terminus is not critical for maintaining enzymatic activity and thermostability.

The thermostability of C-terminal mutations was further examined by incubating various mutants at 65° C. for 30 or 60 minutes. The results are shown below in Table 3:

TABLE 3

| | Percent Activity after Incubation at 65° C. | |
|---|---|---|
| Mutant | 30 Minutes | 60 Minutes |
| K1T | 0 | 0 |
| K1S | 0.53 | ND |
| K1S + G | 0 | ND |
| K1S + GL | 0.55 | ND |
| K1S + GLC (K3) | 19.0 | ND |
| K1S + GLCG | 22.0 | ND |
| K1S + GLCGR | 27.6 | 6.0 |
| K1S + GLSGR | 0 | 0 |

ND = not determined

First, the results in Table 3 confirm the previously reported results that adding the "GLC" tripeptide to the C-terminus (shown in the table as K1S+GLC (K3)) significantly increases the thermostability as compared to enzymes that lack this tripeptide (K1S or K1 T) or that only include a "G" (K1 S+G) or "GL" (K1 S+GL) addition to the C-terminus. Furthermore, adding one residue (K1 S+GLCG) or two residues (K1S+GLCGR) on the C-terminal side of the added cysteine residue maintains this enhanced thermostability. The mutant with two residues added beyond the cysteine residue (K1S+GLCGR) exhibited the greatest thermostability of all mutants tested. Finally, substitution of the cysteine with a serine (K1S+GLSGR) abolished the enhanced thermal stability, thereby demonstrating that the cysteine residue is critical for the enhanced thermal stability.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | DESCRIPTION |
|---|---|
| 1 | E. coli K12 BGUS wild type nucleic acid sequence<br>ATGTTACGTCCTGTAGAAACCCCAACCCGTGAAATCAAAAAACT<br>CGACGGCCTGTGGGCATTCAGTCTGGATCGCGAAAACTGTGGAA<br>TTGATCAGCGTTGGTGGGAAAGCGCGTTACAAGAAAGCCGGGCA<br>ATTGCTGTGCCAGGCAGTTTTAACGATCAGTTCGCCGATGCAGA<br>TATTCGTAATTATGCGGGCAACGTCTGGTATCAGCGCGAAGTCT<br>TTATACCGAAAGGTTGGGCAGGCCAGCGTATCGTGCTGCGTTTC<br>GATGCGGTCACTCATTACGGCAAAGTGTGGGTCAATAATCAGGA<br>AGTGATGGAGCATCAGGGCGGCTATACGCCATTTGAAGCCGATG<br>TCACGCCGTATGTTATTGCCGGGAAAAGTGTACGTATCACCGTT<br>TGTGTGAACAACGAACTGAACTGGCAGACTATCCCGCCGGGAAT<br>GGTGATTACCGACGAAAACGGCAAGAAAAAGCAGTCTTACTTCC<br>ATGATTTCTTTAACTATGCCGGGATCCATCGCAGCGTAATGCTC<br>TACACCACGCCGAACACCTGGGTGGACGATATCACCGTGGTGAC<br>GCATGTCGCGCAAGACTGTAACCACGCGTCTGTTGACTGGCAGG<br>TGGTGGCCAATGGTGATGTCAGCGTTGAACTGCGTGATGCGGAT<br>CAACAGGTGGTTGCAACTGGACAAGGCACTAGCGGGACTTTGCA<br>AGTGGTGAATCCGCACCTCTGGCAACCGGGTGAAGGTTATCTCT |

SUMMARY OF SEQUENCE LISTING

| SEQ ID NO: | DESCRIPTION |
|---|---|
| | ATGAACTGTGCGTCACAGCCAAAAGCCAGACAGAGTGTGATATC TACCCGCTTCGCGTCGGCATCCGGTCAGTGGCAGTGAAGGGCGA ACAGTTCCTGATTAACCACAAACCGTTCTACTTTACTGGCTTTG GTCGTCATGAAGATGCGGACTTGCGTGGCAAAGGATTCGATAAC GTGCTGATGGTGCACGACCACGCATTAATGGACTGGATTGGGGC CAACTCCTACCGTACCTCGCATTACCCTTACGCTGAAGAGATGC TCGACTGGGCAGATGAACATGGCATCGTGGTGATTGATGAAACT GCTGCTGTCGGCTTTAACCTCTCTTTAGGCATTGGTTTCGAAGC GGGCAACAAGCCGAAAGAACTGTACAGCGAAGAGGCAGTCAACG GGGAAACTCAGCAAGCGCACTTACAGGCGATTAAAGAGCTGATA GCGCGTGACAAAAACCACCCAAGCGTGGTGATGTGGAGTATTGC CAACGAACCGGATACCCGTCCGCAAGGTGCACGGGAATATTTCG CGCCACTGGCGGAAGCAACGCGTAAACTCGACCCGACGCGTCCG ATCACCTGCGTCAATGTAATGTTCTGCGACGCTCACACCGATAC CATCAGCGATCTCTTTGATGTGCTGTGCCTGAACCGTTATTACG GATGGTATGTCCAAAGCGGCGATTTGGAAACGGCAGAGAAGGTA CTGGAAAAAGAACTTCTGGCCTGGCAGGAGAAACTGCATCAGCC GATTATCATCACCGAATACGGCGTGGATACGTTAGCCGGGCTGC ACTCAATGTACACCGACATGTGGAGTGAAGAGTATCAGTGTGCA TGGCTGGATATGTATCACCGCGTCTTTGATCGCGTCAGCGCCGT CGTCGGTGAACAGGTATGGAATTTCGCCGATTTTGCGACCTCGC AAGGCATATTGCGCGTTGGCGGTAACAAGAAAGGGATCTTCACT CGCGACCGCAAACCGAAGTCGGCGGCTTTTCTGCTGCAAAAACG CTGGACTGGCATGAACTTCGGTGAAAAACCGCAGCAGGGAGGCA AACAATGA |
| 2 | GAGAGACATATGTTACGTCCTGTAGAAACCCC |
| 3 | GAGAGAAAGCTTTCATTGTTTGCCTCCCTGCT |
| 4 | CTGCTGTCGGCTTTAACCTC |
| 5 | GACCTCGCAAAGCATATTGCG |
| 6 | CGCAATATGCTTTGCGAGGTC |
| 7 | CTAGTTATTGCTCAGCGGT |
| 8 | GCGACCTCGCAAACCATATTGCGC |
| 9 | GCGCAATATGGTTTGCGAGGTCGC |
| 10 | CAAACAAGGCCTATGCTAGAAAGGAGAAGCTTG |
| 11 | CAAGCTTCTCCTTTCTAGCATAGGCCTTGTTTG |
| 12 | TCTTTAGGCATTGGTCCGAAAGAACTGTAC |
| 13 | GTACAGTTCTTTCGGACCAATGCCTAAAGA |
| 14 | TCTTTAGGCATTGGTGAAGAGGCAGTCAAC |
| 15 | GTTGACTGCCTCTTCACCAATGCCTAAAGA |
| 16 | CCGCAGTTCTTCAACGGGGAAACTCAG |
| 17 | GAAGAACTGCGGACCAATGCCTAAAGAG |
| 18 | Wild type *E. coli* K12 BGUS full length amino acid sequence (FIG. 1) |
| 19 | K1S mutant full length amino acid sequence (FIG. 1) |
| 20 | K1T mutant full length amino acid sequence (FIG. 1) |
| 21 | K3 mutant full length amino acid sequence (FIG. 1) |
| 22 | K3Δ1 mutant full length amino acid sequence (FIG. 1) |
| 23 | K3Δ2 mutant full length amino acid sequence (FIG. 1) |
| 24 | K3Δ2S mutant full length amino acid sequence (FIG. 1) |
| 25 | *E. coli* K3 mutant partial amino acid sequence, residues 332-416 (FIG. 2) |
| 26 | Abalone BGUS partial wild-type amino acid sequence (FIG. 2) |
| 27 | Human BGUS partial wild-type amino acid seqeuence (FIG. 2) |
| 28 | *Lactobacillus brevis* BGUS partial wild-type amino acid sequence (FIG. 2) |
| 29 | *Staphylococcus sp.* RLH1 partial wild-type amino acid sequence (FIG. 2) |
| 30 | *E. coli* K3 mutant partial amino acid sequence, residues 452-606 (FIG. 3) |
| 31 | Abalone BGUS partial wild-type amino acid sequence (FIG. 3) |
| 32 | Human BGUS partial wild-type amino acid seqeuence (FIG. 3) |
| 33 | *Lactobacillus brevis* BGUS partial wild-type amino acid sequence (FIG. 3) |
| 34 | *Staphylococcus sp.* RLH1 partial wild-type amino acid sequence (FIG. 3) |
| 35 | Abalone BGUS partial mutant amino acid sequence Ab1 (FIG. 9) |
| 36 | Abalone BGUS partial mutant amino acid sequence Ab 2 (FIG. 9) |
| 37 | Human BGUS partial mutant amino acid sequence Hu1 (FIG. 9) |
| 38 | Human BGUS partial mutant amino acid sequence Hu 2 (FIG. 9) |
| 39 | Human BGUS wild type amino acid sequence margsavawaalgpllwgcalglqggmlypqespsreckeldgl wsfradfsdnrrrgfeeqwyrrplwesgptvdmpvpssfnditq dwrlrhfvgwvvwyerevilperwtqdlrtrvvlrigsahsyaiv wvngvdtlehegggylpfeadisnlvqvgplpsrlritiainntl tpttlppgtiqyltdtskypkgyfvqntyfdffnyaglqrsvll yttpttyidditvttsveqdsglvnyqisvkgsnlfklevrlld aenkvvangtgtqgqlkvpgvslwpylmherpaylyslevqlt aqtslgpvsdfytlpvgirtvavtksqflingkpfyfhgvnkhe dadirgkgfdwpllvkdfnllrwlganafrtshypyaeevmqmc drygivvidecpgvglalpqffnnvslhhhmqvmeevvrrrdknh pavvmwsvanepashlesagyylkmviahtksldpsrpvtfvsn snyaadkgapyvdviclnsyyswyhdyghleliqlqlatqfenw ykkyqkpiiqseygaetiagfhqdpplmfteeyqkslleqyhlg ldkrrkyvvgeliwnfadfmteqsptrvlgnkkgiftrqrqpk saafllrerywkianetryphsvaksqclenslft |
| 40 | Mouse BGUS wild type amino acid sequence mslkwsacwvalgqllcscalalkggmlfpkespsrelkaldgl whfradlsnnrlqgfeqqwyrqplresgpvldmpvpssfnditq eaaalrdfigwvwyereaailprrwtqdtdmrvvlrinsahyyavv wvngihvvehegghlpfeadisklvqsgplttcritiainntlt phtlppgtivyktdtsmypkgyfvqdtsfdffnyaglhrsvvly ttpttyidditvitnveqdiglvtywisvqgsehfqlevqllde ggkvvahgtgnqgqlqvpsanlwpylmhehpaymyslevkvtt |

SUMMARY OF SEQUENCE LISTING

| SEQ ID NO: | DESCRIPTION |
|---|---|
| | tesvtdyytlpigirtvavtkskflingkpfyfqgvnkhedsdi vrgkgfdwpllvkdfnllrwlgansfrtshypyseevlqlcdry givvidecpgvgivlpqsfgneslrhhlevmeelvrrdknhpav vmwsvanepssalkpaayyfktlithtkaldltrpvtfvsnaky dadlgapyvdvicvnsyfswyhdyghleviqpqlnsqfenwykt hqkpiiqseygadaipgihedpprmfseeyqkavlenyhsvldq krkeyvgeliwnfadfmtnqsplrvignkkgiftrqrqpktsaf ilrerywrianetgghgsgprtqcfgsrptftf |
| 41 | Lactobacillus brevis BGUS wild type amino acid sequence<br>mlypmetasrvvldlsgvwrfmidkeqipvdvtrplpatlsmav pasfndqtaskeirehvgyvwyercfelpqllrgerlvlrfgsa theawvylnghlithhkggftpfeveinddlvtgenrltvklsn mldyttlpvghyketqnetgqrvrqldenfdffnyaglqrpvki ystphsyirditltpkvnltnhsavvngeietvgdveqvvvtil dednqvvgttsgktlaielnsvhlwqpgkaylyrakvelyqagq vidtyietfgirqiavkagkflingqpfyfkgfgkhedayihgr glsepqnvldlslmkqmgansfrtshypyseemmrlcdregivv idevpavglmlsftfdvsalekddfeddtweklrtaeahrqait emidrdknhasvvmwsisneaanfskgayeyfkplfdlarkldp qqrpctststsimmttlktdrclaladvialnryygwymgngdlka aetatreellayqakfpdkpimyteygadtiaglhsnydepfse efqedyyrmcsrvfdevtnfvgeqlwnfadfqtkfgiqrgqgnk kgiftrarepkmvvryltqrwrnipdfnykk |
| 42 | Staphylococcus sp. RLH1 BGUS wild type amino acid sequence<br>mlypintetrgvfdlngvwnfkldygkgleekwyeskltdtism avpssyndigvtkeirnhigyvwyereftvpaylkdqrivlrfg sathkaivyvngelvvehkggflpfeaeeinnslrdgmnrvtvav dnilddstlpvglyserheeglgkvirnkpnfdffnyaglhrpv kiyttpftyvedisvvtdfngptgvtvtytvdfqgskaetvkvsvv deegkvvastegslsgnveipnvilweplntylyqikvelvndgl tidvyeepfgvrtvevndgkflinnkpfyfkgfgkhedtpingr gfneasnvmdfnilkwigansfrtahypyseelmrladregllvv idetpavgvhlnfmattglgegservstwekirtfehhqdvlre lvsrdknhpsvvmwsianeaateeegayeyfkplveltkeldpq krpvtivlfvmatpetdkvaelidvialnryngwyfdggdleaa kvhlrqefhawnkrcpgkpimiteygadtvagfhdidpvmftee yqveyyqanhvvfdefenfvgeqawnfadfatsqgvmrvqgnkk gvftrdrkpklaahvfrerwtnipdfgykn |
| 43 | GCAAAATCGGCGAAATTC |
| 44 | GACCTCGCAAGCATATTGCGCGTTG |
| 45 | GACCTCGCAATGTATATTGCGCGTTG |
| 46 | GACCTCGCAAGATATTGCGCGTTG |
| 47 | GACCTCGCAAGAAATATTGCGCGTTG |
| 48 | GACCTCGCAATTCATATTGCGCGTTG |
| 49 | GACCTCGCAACATATATTGCGCGTTG |
| 50 | GACCTCGCAAATCATATTGCGCGTTG |
| 51 | GACCTCGCAAAAAATATTGCGCGTTG |
| 52 | GACCTCGCAACTGATATTGCGCGTTG |
| 53 | GACCTCGCAAATGATATTGCGCGTTG |
| 54 | GACCTCGCAAAACATATTGCGCGTTG |
| 55 | GACCTCGCAACCGATATTGCGCGTTG |
| 56 | GACCTCGCAACAGATATTGCGCGTTG |
| 57 | GACCTCGCAACGTATATTGCGCGTTG |
| 58 | GACCTCGCAAGTGATATTGCGCGTTG |
| 59 | GACCTCGCAATGGATATTGCGCGTTG |
| 60 | GACCTCGCAATACATATTGCGCGTTG |
| 61 | E. coli K12 BGUS G559H mutant amino acid sequence<br>mlrpvetptreikkldglwafsldrencgidqrwwesalqesra iavpgsfndqfadadirnyagnvwygrevfipkgwagqrivlrf davthygkvwvnnqevmehqggytpfeadvtpyviagksvritv cvnnelnwqtippgmvitdengkkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgegflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqhilrvggnkkgift rdrkpksaafllqkrwtgmnfgekpqqggkq |
| 62 | E. coli K12 BGUS G559H + GLC C-terminal mutant amino acid sequence<br>mlrpvetptreikkldglwafsldrencgidqrwwesalqesra iavpgsfndqfadadirnyagnvwygrevfipkgwagqrivlrf davthygkvwvnnqevmehqggytpfeadvtpyviagksvritv cvnnelnwqtippgmvitdengkkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgegflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqhilrvggnkkgift rdrkpksaafllqkrwtgmnfgekpqqggkqglc |
| 63 | E. coli K12 BGUS G559H + GLCGR C-terminal mutant amino acid sequence<br>mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgegflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqhilrvggnkkgift rdrkpksaafllqkrwtgmnfgekpqqggkqglcgr |
| 64 | E. coli K12 BGUS G559N mutant amino acid sequence<br>mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgegflinhkpfyftgfgrhedadlrgkgfdn vlmvhdhalmdwigansyrtshypyaeemldwadehgivvidet aavgfnlslgigfeagnkpkelyseeavngetqqahlqaikeli |

SUMMARY OF SEQUENCE LISTING

| SEQ ID NO: | DESCRIPTION |
|---|---|
| | ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqnilrvggnkkgift<br>rdrkpksaafllqkrwtgmnfgekpqqggkq |
| 65 | *E. coli* K12 BGUS G559N + GLC C-terminal mutant amino acid sequence<br>mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvritv<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqnilrvggnkkgift<br>rdrkpksaafllqkrwtgmnfgekpqqggkqglc |
| 66 | *E. coli* K12 BGUS G559N + GLCGR C-terminal mutant amino acid sequence<br>mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvrity<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrysavvgeqvwnfadfatsqnilrvggnkkgift<br>rdrkpksaafllqkrwtgmnfgekpqqggkqglcgr |
| 67 | mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvrity<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyahtdtisdlfaplaea<br>trkldptrpitcvnvmfcdfdvlclnryygwyvqsgdletaekv<br>lekellawqeklhqpiiiteygvdtlaglhsmytdmwseeyqca<br>wldmyhrvfdrysavvgeqvwnfadfatsqsilrvggnkkgift<br>rdrkpksaafllqkrwtgmnfgekpqqggkqsscxx |
| 68 | mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvritv<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqsilrvggnkkgift<br>rdrkpksaafllqkrwtgmnfgekpqqggkqeecxx |
| 69 | mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvritv<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqsilrvggnkkgift<br>rdrkpksaafllqkrwtgmnfgekpqqggkqkkcxx |
| 70 | mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvritv<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqsilrvggnkkgift<br>rdrkpksaafllqkrwtgmnfgekpqqggkqaacxx |
| 71 | mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvritv<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqsilrvggnkkgift<br>rdrkpksaafllqkrwtgmnfgekpqqggkqwwcxx |
| 72 | mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvritv<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqsilrvggnkkgift<br>rdrkpksaafllqkrwtgmnfgekpqqggkqppcxx |
| 73 | mlrpvetptreikkldglwafsldrencgidqrwwesalqesra<br>iavpgsfndqfadadirnyagnvwyqrevfipkgwagqrivlrf<br>davthygkvwvnnqevmehqggytpfeadvtpyviagksvritv<br>cvnnelnwqtippgmvitdengkkkqsyfhdffnyagihrsvml<br>yttpntwvdditvvthvaqdcnhasvdwqvvangdvsvelrdad<br>qqvvatgqgtsgtlqvvnphlwqpgegylyelcvtaksqtecdi<br>yplrvgirsvavkgeqflinhkpfyftgfgrhedadlrgkgfdn<br>vlmvhdhalmdwigansyrtshypyaeemldwadehgivvidet<br>aavgfnlslgigfeagnkpkelyseeavngetqqahlqaikeli<br>ardknhpsvvmwsianepdtrpqgareyfaplaeatrkldptrp<br>itcvnvmfcdahtdtisdlfdvlclnryygwyvqsgdletaekv<br>lekellawqeklhqpiiiteygvdtlaglhsmytdmwseeyqca<br>wldmyhrvfdrvsavvgeqvwnfadfatsqsilrvggnkkgift<br>rdrkpksaafllqkrwtgmnfgekpqqggkqglcxx |
| 74 | mlrpvetptreikkldglwafsldrencgidqrwwesalqesra<br>iavpgsfndqfadadirnyagnvwyqrevfipkgwagqrivlrf |

SUMMARY OF SEQUENCE LISTING

| SEQ ID NO: | DESCRIPTION |
|---|---|
| | davthygkvwvnnqevmehqggytpfeadvtpyviagksvritv cvnnelnwqtippgmvitdengkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgeqflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqsilrvggnkkgift rdrkpksaafllqkrwtgmnfgekpqqggkqglggcxx |
| 75 | mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgegflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqsilrvggnkkgift rdrkpksaafllqkrwtgmnfgekpqqggkqglggcxx |
| 76 | mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgeqflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqsilrvggnkkgift rdrkpksaafllqkrwtgmnfgekpqqggkqglgggcxx |
| 77 | mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgeqflinhkpfyftgfgrhedadlrgkgfdn vlmvhdhalmdwigansyrtshypyaeemldwadehgivvidet aavgfnlslgigfeagnkpkelyseeavngetqqahlqaike- liardknhpsvvmwsianepdtrpqgareyfaplaeatrkldp- trpitcvnvmfcdahtdtisdlfdvlclnryygwyvqsgdle- taekvlekellawqeklhqpiiiteygvdtlaglhsmytdmws- eeyqcawldmyhrvfdrvsavvgeqvwnfadfatsq silrvggnkkgiftrdrkpksaafllqkrwtgmnfgekpqqggkq glggggcxx |
| 78 | mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgeqflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqsilrvggnkkgift rdrkpksaafllqkrwtgmnfgekpqqggkqglggggcxx |
| 79 | AGCAGCTGCGGCCGGTAGAAAGGAG |
| 80 | GAAGAATGCGGCCGGTAGAAAGGAG |
| 81 | AAAAAATGCGGCCGGTAGAAAGGAG |
| 82 | GCGGCGTGCGGCCGGTAGAAAGGAG |
| 83 | TGGTGGTGCGGCCGGTAGAAAGGAG |
| 84 | CCGCCGTGCGGCCGGTAGAAAGGAG |
| 85 | TTGTTTGCCTCCCTGCTG |
| 86 | GGCTGCGGCCGGTAGAAAGGAG |
| 87 | GGCGGCTGCGGCCGGTAGAAAGGAG |
| 88 | GGCGGCGCTGCGGCCGGTAGAAAGGAG |
| 89 | GGCGGCGGCTGCGGCCGGTAGAAAGGAG |
| 90 | GGCGGCGGCGGCTGCGGCCGGTAGAAAGGAG |
| 91 | GGCGGCGGCGGCGGCTGCGGCCGGTAGAAAGGAG |
| 92 | TAGGCCTTGTTTGCCTCCC |
| 93 | mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgeqflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqzilrvggnkkgift rdrkpksaafllqkrwtgmnfgekpqqggkqx$_{2-8}$cx$_{0-2}$, wherein z = s, t, h or n, and x = any a.a. |
| 94 | mlrpvetptreikkldglwafsldrencgidqrwwesalqesra iavpgsfndqfadadirnyagnvwyqrevfipkgwagqrivlrf davthygkvwvnnqevmehqggytpfeadvtpyviagksvritv cvnnelnwqtippgmvitdengkkqsyfhdffnyagihrsvml yttpntwvdditvvthvaqdcnhasvdwqvvangdvsvelrdad qqvvatgqgtsgtlqvvnphlwqpgegylyelcvtaksqtecdi yplrvgirsvavkgeqflinhkpfyftgfgrhedadlrgkgfdn vlmvhdhalmdwigansyrtshypyaeemldwadehgivvidet aavgfnlslgigfeagnkpkelyseeavngetqqahlqaikeli ardknhpsvvmwsianepdtrpqgareyfaplaeatrkldptrp itcvnvmfcdahtdtisdlfdvlclnryygwyvqsgdletaekv lekellawqeklhqpiiiteygvdtlaglhsmytdmwseeyqca wldmyhrvfdrvsavvgeqvwnfadfatsqsilrvggnkkgift rdrkpksaafllqkrwtgmnfgekpqqggkqglcgr |
| 95 | Xaa$_{2-8}$-Cys-Xaa$_{0-2}$, wherein Xaa = any amino acid |
| 96 | glcgr |

The invention claimed is:

1. A packaged formulation comprising a container comprising a preparation of a β-glucuronidase enzyme, wherein:
   (i) the β-glucuronidase enzyme consists of a mutation, as compared to a wild-type version of the β-glucuronidase enzyme, consisting of a substitution of an amino acid corresponding to G559 in SEQ ID NO: 18 with an amino acid comprising a side chain comprising a non-aromatic hydroxyl group or histidine or asparagine, as compared to the sequence of the wild-type β-glucuronidase enzyme, with all other amino acid residues of the β-glucuronidase enzyme being wild-type; and
   (ii) the preparation of β-glucuronidase enzyme has an enzymatic activity of at least 5,000 Units/ml or 5,000 Units/mg.

2. The packaged formulation of claim 1, wherein the β-glucuronidase enzyme consists of a mutation consisting of a substitution of an amino acid corresponding to G559 in SEQ ID NO: 18 with serine.

3. The packaged formulation of claim 1, wherein the β-glucuronidase enzyme consists of a mutation consisting of a substitution of an amino acid corresponding to G559 in SEQ ID NO: 18 with threonine.

4. The packaged formulation of claim 1, wherein the β-glucuronidase enzyme comprises the amino acid sequence as shown in SEQ ID NO: 19.

5. The packaged formulation of claim 1, wherein the β-glucuronidase enzyme comprises the amino acid sequence as shown in SEQ ID NO: 20.

6. The packaged formulation of claim 1, wherein the β-glucuronidase enzyme is in an aqueous solution with an enzymatic activity of at least 50,000 Units/ml.

7. The packaged formulation of claim 1, wherein the β-glucuronidase enzyme is in a lyophilized preparation with an enzymatic activity of at least 50,000 Units/mg.

8. The packaged formulation of claim 1, wherein the preparation is stable at least six months at 2-8° C.

9. The packaged formulation of claim 1, wherein the preparation lacks detectable sulfatase activity.

10. The packaged formulation of claim 1, wherein the β-glucuronidase enzyme is a mutant version of a β-glucuronidase enzyme from a bacteria.

11. The packaged formulation of claim 10, wherein the β-glucuronidase enzyme is a mutant version of a β-glucuronidase enzyme from *Escherichia coli*.

12. The packaged formulation of claim 1, wherein the β-glucuronidase enzyme is a mutant version of a β-glucuronidase enzyme from a mollusk.

13. The packaged formulation of claim 12, wherein the β-glucuronidase enzyme is a mutant version of a β-glucuronidase enzyme from a snail or abalone.

14. The packaged formulation of claim 1, wherein the β-glucuronidase enzyme is a mutant version of a β-glucuronidase enzyme from a human.

15. A mutated β-glucuronidase enzyme consisting of two mutations as compared to a wild-type version of the β-glucuronidase enzyme, wherein the two mutations consist of:
   (i) a substitution of an amino acid corresponding to G559 in SEQ ID NO: 18 with an amino acid comprising a side chain comprising a non-aromatic hydroxyl group or histidine or asparagine, as compared to the wild-type version of the β-glucuronidase enzyme; and
   (ii) an addition of a cysteine residue appended at or near the carboxy terminus of the enzyme, wherein the carboxy terminus has the sequence: $Xaa_{2-8}$-Cys-$Xaa_{0-2}$, wherein Xaa=any amino acid.

16. A mutated β-glucuronidase enzyme comprising:
   (i) a substitution of an amino acid corresponding to G559 in SEQ ID NO: 18 with an amino acid comprising a side chain comprising a non-aromatic hydroxyl group or histidine or asparagine; and
   (ii) a modification comprising an insertion of a region comprising amino acids corresponding to F365 through K370 in SEQ ID NO: 18.

17. A mutated β-glucuronidase enzyme comprising:
   (i) a substitution of an amino acid corresponding to G559 in SEQ ID NO: 18 with an amino acid comprising a side chain comprising a non-aromatic hydroxyl group or histidine or asparagine;
   (ii) an addition of a cysteine residue appended at or near the carboxy terminus of the enzyme; and
   (iii) a modification comprising an insertion of a region comprising amino acids corresponding to F365 through K370 in SEQ ID NO: 18.

18. A mutated β-glucuronidase enzyme comprising:
   (i) an addition of a cysteine residue appended at or near the carboxy terminus of the enzyme, wherein the carboxy terminus has the sequence: $Xaa_{2-8}$-Cys-$Xaa_{0-2}$, wherein Xaa=any amino acid; and
   (ii) a modification comprising an insertion of a region comprising amino acids corresponding to F365 through K370 in SEQ ID NO: 18, wherein the mutated β-glucuronidase enzyme is not SEQ ID NO: 18.

19. The mutated β-glucuronidase enzyme of claim 15, wherein the cysteine residue appended at the carboxy terminus comprises a tripeptide Glycine-Leucine-Cysteine, wherein the carboxy terminus has the sequence: $Xaa_{2-8}$-Cys-$Xaa_{0-2}$, wherein Xaa=any amino acid.

20. A packaged formulation comprising a container comprising a preparation of the mutated β-glucuronidase enzyme of claim 15, wherein the preparation has an enzymatic activity of at least 5,000 Units/ml or 5,000 Units/mg.

21. A mutated β-glucuronidase enzyme comprising a substitution of an amino acid corresponding to G559 in SEQ ID NO: 18 with histidine.

22. A mutated version of a wild-type β-glucuronidase enzyme, the mutated version having a mutation consisting of a substitution of an amino acid corresponding to G559 in SEQ ID NO: 18 with asparagine, as compared to the sequence of the wild-type β-glucuronidase enzyme, with all other amino acid residues of the mutated version being wild-type.

23. A mutated β-glucuronidase enzyme comprising the amino acid sequence shown in SEQ ID NO: 93.

24. The mutated β-glucuronidase enzyme of claim 17, wherein the cysteine residue appended at the carboxy terminus comprises a tripeptide Glycine-Leucine-Cysteine, wherein the carboxy terminus has the sequence: $Xaa_{2-8}$-Cys-$Xaa_{0-2}$, wherein Xaa=any amino acid.

25. The mutated β-glucuronidase enzyme of claim 18, wherein the cysteine residue appended at the carboxy terminus comprises a tripeptide Glycine-Leucine-Cysteine, wherein the carboxy terminus has the sequence: $Xaa_{2-8}$-Cys-$Xaa_{0-2}$, wherein Xaa=any amino acid.

26. A packaged formulation comprising a container comprising a preparation of the mutated β-glucuronidase enzyme of claim 16, wherein the preparation has an enzymatic activity of at least 5,000 Units/ml or 5,000 Units/mg.

27. A packaged formulation comprising a container comprising a preparation of the mutated β-glucuronidase enzyme of claim 17, wherein the preparation has an enzymatic activity of at least 5,000 Units/ml or 5,000 Units/mg.

28. A packaged formulation comprising a container comprising a preparation of the mutated β-glucuronidase enzyme of claim 18, wherein the preparation has an enzymatic activity of at least 5,000 Units/ml or 5,000 Units/mg.

29. A mutated β-glucuronidase enzyme comprising the amino acid sequence shown in SEQ ID NO: 21.

30. A mutated β-glucuronidase enzyme comprising the amino acid sequence shown in SEQ ID NO: 22.

31. A mutated β-glucuronidase enzyme comprising the amino acid sequence shown in SEQ ID NO: 23.

32. A mutated β-glucuronidase enzyme comprising the amino acid sequence shown in SEQ ID NO: 24.

33. A mutated β-glucuronidase enzyme comprising the amino acid sequence shown in SEQ ID NO: 94.

34. The packaged formulation of claim 1, wherein the β-glucuronidase enzyme consists of a mutation consisting of a substitution of an amino acid corresponding to G559 in SEQ ID NO: 18 with histidine.

35. The packaged formulation of claim 1, wherein the β-glucuronidase enzyme consists of a mutation consisting of a substitution of an amino acid corresponding to G559 in SEQ ID NO: 18 with asparagine.

* * * * *